United States Patent
Wu et al.

(10) Patent No.: US 10,988,753 B2
(45) Date of Patent: Apr. 27, 2021

(54) ASPARTASE VARIANTS, METHOD OF PREPARING THE SAME AND USE THEREOF

(71) Applicant: QINHUANGDAO HUAHENG BIOENGINEERING CO., LTD., Qinhuangdao (CN)

(72) Inventors: Bian Wu, Qinhuangdao (CN); Yang Liu, Qinhuangdao (CN); Ruifeng Li, Qinhuangdao (CN); Dongzhu Zhang, Qinhuangdao (CN); Zhicheng Liu, Qinhuangdao (CN); Hui Zhang, Qinhuangdao (CN)

(73) Assignee: QINHUANGDAO HUAHENG BIOENGINEERING CO., LTD., Qinhuangdao (CN)

( * ) Notice: Subject to any disclaimer, the term of this patent is extended or adjusted under 35 U.S.C. 154(b) by 0 days.

(21) Appl. No.: 16/632,838

(22) PCT Filed: Jul. 24, 2018

(86) PCT No.: PCT/CN2018/096737
§ 371 (c)(1),
(2) Date: Jan. 21, 2020

(87) PCT Pub. No.: WO2019/024706
PCT Pub. Date: Feb. 7, 2019

(65) Prior Publication Data
US 2020/0157522 A1    May 21, 2020

(30) Foreign Application Priority Data
Aug. 4, 2017 (CN) .......................... 201710659654.9

(51) Int. Cl.
*C12N 9/88* (2006.01)
*C12P 13/06* (2006.01)

(52) U.S. Cl.
CPC ................ *C12N 9/88* (2013.01); *C12P 13/06* (2013.01); *C12Y 403/01001* (2013.01)

(58) Field of Classification Search
CPC .... C12N 9/88; C12Y 403/01001; C12P 13/06
See application file for complete search history.

(56) References Cited

PUBLICATIONS

Vogel et al., "Converting Aspartase into a β-Amino Acid Lyase by Cluster Screening", Chemcatchem., vol. 6, Dec. 31, 2014, pp. 965-968.
International search report dated Sep. 29, 2018 from corresponding application No. PCT/CN2018/096737.

*Primary Examiner* — Ganapathirama Raghu
(74) *Attorney, Agent, or Firm* — Hauptman Ham, LLP

(57) ABSTRACT

The present invention discloses an aspartase variant, method of preparing the same and use thereof. Compared with sequence 2 in the sequence listing, the amino acid sequence of the aspartase variant provided in the present invention has more than 96% identity, and there are mutations in T187I and N326C at positions 187 and 326, respectively, and has improved catalytic activity for the ammoniation of acrylic acid, compared with the aspartase shown in sequence 2. The experiment proves that the aspartase variant provided in the present invention does have improved catalytic activity for the ammoniation of acrylic acid compared with the wild type parent aspartase, and has better thermal stability and pH spectrum. The reaction can greatly increase the conversion ratio of acrylic acid.

9 Claims, No Drawings
Specification includes a Sequence Listing.

SEQUENCE LISTING

<160> NUMBER OF SEQ ID NOS: 2

<210> SEQ ID NO 1
<211> LENGTH: 1404
<212> TYPE: DNA
<213> ORGANISM: Bacillus sp.

<400> SEQUENCE: 1

```
atgaataccg atgttcgtat tgagaaagac tttttaggag aaaaggagat tccgaaagac      60
gcttattatg gcgtacaaac aattcgggca acggaaaatt ttccaattac aggttatcgt     120
attcatccag aattaattaa atcactaggg attgtaaaaa aatcagccgc attagcaaac     180
atggaagttg gcttactcga taaagaagtt gggcaatata tcgtaaaagc tgctgacgaa     240
gtgattgaag gaaaatggaa tgatcaattt attgttgacc caattcaagg cggggcagga     300
acttccatta tatgaatgc aaatgaagtg attgctaacc gcgcattaga attaatggga     360
gaggaaaaag gaaactattc aaaaattagt ccaaactccc atgtaaatat gtctcaatca     420
acaaacgatg ctttccctac tgcaacgcat attgctgtgt taagtttatt aaatcaatta     480
attgaaacta caaaatacat gcaacaagaa ttcatgaaaa aagcagatga attcgctggc     540
```

```
gttattaaaa tgggaagaac gcacttgcaa gacgctgttc ctattttatt aggacaagag    600
tttgaagcat atgctcgtgt aattgcccgc gatattgaac gtattgccaa tacgagaaac    660
aatttatacg acatcaacat gggtgcaaca gcagtcggca ctggcttaaa tgcagatcct    720
gaatatataa gcatcgtaac agaacattta gcaaaattca gcggacatcc attaagaagt    780
gcacaacatt tagtggacgc aactcaaaat acagactgct atacagaagt ttcttctgca    840
ttaaaagttt gcatgatcaa catgtctaaa attgccaatg atttacgctt aatggcatct    900
ggaccacgcg caggcttatc agaaatcgtt cttcctgctc gacaacctgg atcttctatc    960
atgcctggta aagtgaatcc tgttatgcca gaagtgatga accaagtggc attccaagtg   1020
ttcggtaatg atttaacaat tacatctgct tctgaagcag gccaatttga attaaatgtg   1080
atggaacctg tgttattctt caatttaatt caatcgattt cgattatgac taatgtctttt   1140 aaatccttta cagaaaactg cttaaaaggt attaaggcaa atgaagaacg catgaaagaa   1200
tatgttgaga aaagcattgg aatcattact gcaattaacc cacatgtagg ctatgaaaca   1260
gctgcaaaat tagcacgtga agcatatctt acaggggaat ccatccgtga actttgcatt   1320
aagtatggcg tattaacaga agaacagtta aatgaaatct taaatccata tgaaatgaca   1380
catccgggaa ttgctggaag aaaa                                           1404
```

<210> SEQ ID NO 2
<211> LENGTH: 468
<212> TYPE: PRT
<213> ORGANISM: Bacillus sp.

<400> SEQUENCE: 2

```
Met Asn Thr Asp Val Arg Ile Glu Lys Asp Phe Leu Gly Glu Lys Glu
1               5                   10                  15

Ile Pro Lys Asp Ala Tyr Tyr Gly Val Gln Thr Ile Arg Ala Thr Glu
            20                  25                  30

Asn Phe Pro Ile Thr Gly Tyr Arg Ile His Pro Glu Leu Ile Lys Ser
        35                  40                  45

Leu Gly Ile Val Lys Lys Ser Ala Ala Leu Ala Asn Met Glu Val Gly
    50                  55                  60

Leu Leu Asp Lys Glu Val Gly Gln Tyr Ile Val Lys Ala Ala Asp Glu
65                  70                  75                  80

Val Ile Glu Gly Lys Trp Asn Asp Gln Phe Ile Val Asp Pro Ile Gln
                85                  90                  95

Gly Gly Ala Gly Thr Ser Ile Asn Met Asn Ala Asn Glu Val Ile Ala
            100                 105                 110

Asn Arg Ala Leu Glu Leu Met Gly Glu Glu Lys Gly Asn Tyr Ser Lys
        115                 120                 125

Ile Ser Pro Asn Ser His Val Asn Met Ser Gln Ser Thr Asn Asp Ala
    130                 135                 140

Phe Pro Thr Ala Thr His Ile Ala Val Leu Ser Leu Leu Asn Gln Leu
145                 150                 155                 160

Ile Glu Thr Thr Lys Tyr Met Gln Gln Glu Phe Met Lys Lys Ala Asp
                165                 170                 175

Glu Phe Ala Gly Val Ile Lys Met Gly Arg Thr His Leu Gln Asp Ala
            180                 185                 190

Val Pro Ile Leu Leu Gly Gln Glu Phe Glu Ala Tyr Ala Arg Val Ile
        195                 200                 205

Ala Arg Asp Ile Glu Arg Ile Ala Asn Thr Arg Asn Asn Leu Tyr Asp
    210                 215                 220
```

```
Ile Asn Met Gly Ala Thr Ala Val Gly Thr Gly Leu Asn Ala Asp Pro
225                 230                 235                 240

Glu Tyr Ile Ser Ile Val Thr Glu His Leu Ala Lys Phe Ser Gly His
            245                 250                 255

Pro Leu Arg Ser Ala Gln His Leu Val Asp Ala Thr Gln Asn Thr Asp
            260                 265                 270

Cys Tyr Thr Glu Val Ser Ser Ala Leu Lys Val Cys Met Ile Asn Met
        275                 280                 285

Ser Lys Ile Ala Asn Asp Leu Arg Leu Met Ala Ser Gly Pro Arg Ala
    290                 295                 300

Gly Leu Ser Glu Ile Val Leu Pro Ala Arg Gln Pro Gly Ser Ser Ile
305                 310                 315                 320

Met Pro Gly Lys Val Asn Pro Val Met Pro Glu Val Met Asn Gln Val
                325                 330                 335

Ala Phe Gln Val Phe Gly Asn Asp Leu Thr Ile Thr Ser Ala Ser Glu
            340                 345                 350

Ala Gly Gln Phe Glu Leu Asn Val Met Glu Pro Val Leu Phe Phe Asn
            355                 360                 365

Leu Ile Gln Ser Ile Ser Ile Met Thr Asn Val Phe Lys Ser Phe Thr
    370                 375                 380

Glu Asn Cys Leu Lys Gly Ile Lys Ala Asn Glu Glu Arg Met Lys Glu
385                 390                 395                 400

Tyr Val Glu Lys Ser Ile Gly Ile Ile Thr Ala Ile Asn Pro His Val
            405                 410                 415

Gly Tyr Glu Thr Ala Ala Lys Leu Ala Arg Glu Ala Tyr Leu Thr Gly
            420                 425                 430

Glu Ser Ile Arg Glu Leu Cys Ile Lys Tyr Gly Val Leu Thr Glu Glu
        435                 440                 445

Gln Leu Asn Glu Ile Leu Asn Pro Tyr Glu Met Thr His Pro Gly Ile
    450                 455                 460

Ala Gly Arg Lys
465
```

US 10,988,753 B2

1

ASPARTASE VARIANTS, METHOD OF PREPARING THE SAME AND USE THEREOF

RELATED APPLICATIONS

The present application is a National Phase of International Application Number PCT/CN2018/096,737, filed Jul. 24, 2018, which claims priority to Chinese Application Number CN201710659654.9, filed Aug. 4, 2017.

INCORPORATION BY REFERENCE

The sequence listing provided in the file entitled SEQUENCE_LISTING.txt, which is an ASCII text file that was created on Jan. 21, 2020, and which comprises 6,202 bytes, is hereby incorporated by reference in its entirety.

TECHNICAL FIELD

The present invention relates to the field of biotechnology, specifically, to an aspartase variant, a method of preparing the same and use thereof.

BACKGROUND OF THE INVENTION

Aspartase (E.C.4.3.1.1), which is also known as aspartate ammonia-lyase, is widely present in bacteria, yeasts and plants. The aspartase derived from *E. coli* consists of 4 same subunits, wherein each subunit consists of 207 amino acid residues, and the molecular weight of each subunit is 52.2 KDa. Activated aspartases are all in the form of tetramer, and its monomer is inactive. The depolymerization of a tetramer into dimers is reversible, and the activity of the dimer structure is 45% of that of the tetramer.

Aspartase is a kind of allosteric enzyme, with an optimum pH of 8.0, and a temperature of 37° C. When pH>7.5, the activity of this enzyme mainly depends on divalent metal ions and aspartic acid; and when pH<7.5, a deamination reaction can be catalyzed without divalent metal ions. A main function of an aspartase in the body is to decompose L-aspartic acid as a carbon source. Taking *E. coli* as an example, if glucose is included in medium, the expression of aspartase is inhibited. In this case, even if L-aspartic acid is used as the only carbon source in the medium, the expression of aspartase may not be promoted. In addition to the regulation in the genetic level, aspartases have regulatory functions. When the enzyme is expressed in a lower level, it is difficult to form a tetramer, and the activity is decreased. The enzyme may be activated by aspartic acid, and when the concentration of aspartic acid is lower, the activity of the enzyme is lower accordingly.

Aspartase is a member of the fumarase superfamily. This family includes aspartases, fumarases, and argininosuccinases derived from different biological species. All members in the aspartase-fumarase family do not need a coenzyme or a prosthetic group to carry out a catalytic reaction. They may be enzymes of this family derived from a four-subunit enzyme recognizing fumaric acid and without regulatory function. All members in this family remain a common function of opening a fumaric acid double bond. Fumarase may catalyze fumaric acid to open double bonds with water, arginine succinic acid lyase may catalyze fumaric acid to open double bonds with arginine, and aspartase may catalyze fumaric acid to open double bonds with $NH^{4+}$. Since this specific function of aspartase, it is widely used for catalyzing the ammoniation of fumaric acid to produce L-aspartic acid, and this reaction is a reversible one.

In recent thirty years, catalyze sites and reaction mechanism for producing L-aspartic acid by catalyzing the ammoniation of fumaric acid by aspartases have been researched deeply by researcher. The reaction mechanism of aspartase for substrate is more and more clear. It also lays a theoretical foundation for the directional modification of aspartase. Based on the fact that aspartase may remove amino groups from a substrate to form an alpha, beta double bond, it is attempted that its catalyze mechanism might be changed to synthesize other species of alpha amino acid with a higher optical purity. However, since the specificity of aspartase for a substrate is high, the process on researching substrates on which the aspartase can be acted is relatively slow. Asano et al., (Biomol. Eng (2005) 22:95-101) find when mutagenesis is carried out on the site of Lys327 of aspartase, the aspartase may catalyze beta-asparagines deamination, but its enzyme activity is very low. If broadened substrates are intended, it might be needed to modify the SS-loop substrate binding domain, which might be a great challenge to the modification of aspartases.

One unsaturated double bond directly binding to carboxy group is also present in acrylic acid, similarly with the structure of fumaric acid. The manner of opening double bond in acrylic acid with adding $NH4^+$ to produce beta-alanine, has been considered as one simplest process for synthesizing beta-alanine. However, the production of beta-alanine is mainly by employing traditional chemical synthesis through the ammoniation of acrylonitrile. There are several defects in this method, such as more by-products, higher energy consumption, a greater environmental contamination. In this light, a great number of researches on synthesizing beta-alanine through ammoniation of acrylic acid are carried out by researchers worldwide. However, no industrialized enzymatic synthesis process has been reported so far. According to literature research, Lou Jian (Study on the production of β-alanine by biotransformation, 2006) has screened a strain of *Sarcina lutea* containing β-alanine synthetase. Even after mutagenesis and optimization of conditions, its acrylic acid conversion ratio is still only 1.25%, which is far from meeting the needs of industrialization.

Wildtype aspartase has a high substrate specificity for fumaric acid, and its enzyme activity to produce β-alanine through the catalysis of the ammoniation of acrylic acid is only about 0.01 U/mg.

SUMMARY OF THE INVENTION

The object of the present invention is to modify the wild type of aspartase, so as to improve its catalyze activity of the ammoniation of acrylic acid to produce beta-alanine.

The present invention firstly provides the following aspartase variants, the amino acid sequence of which is more than 96% identical to sequence 2 (derived from a wild type aspartase from *Bacillus*) in the sequence listing, and both mutations of T187I and N326C are present at positions 187 and 326 in sequence 2. Further, it has an improved catalytic activity for the ammoniation of acrylic acid compared with the aspartase shown in sequence 2.

Wherein, the wild type aspartase shown in sequence 2 is a protein mature body. The term "protein mature body" means a protein present in its final form after the translation and any post-translational modification (such as, N-terminal processing, C-terminal truncation, glycosylation, phosphorylation, and the like). In other words, the protein mature body refers to the remaining portion of a precursor protein after cleavage of the signal peptide portion and, if any, the prepeptide portion. The signal peptide portion can be predicted by procedures known in the art, such as SignalP. The amino acid residues 1 to 468 of sequence 2 are the expected mature portion. Generally, the first amino acid of the mature portion of an enzyme can be determined by N-terminal sequencing of the purified enzyme.

The technical term "identity" herein means that the correlation between two amino acid sequences or two nucleotide sequences is described by the parameter "identity". In the present invention, the degree of sequence identity between two amino acid sequences can be determined by the Needleman-Wunsch algorithm (Needleman and Wunsch, 1970, J. Mol. Biol. 48: 443-453) in the Needle program (preferably, version 3.0.0 or later) in the EMBOSS package (EMBOSS: The European Molecular Biology Open Software Suite, et al., 2000, Trends Genet. 16: 276-277). The optional parameters that can be used are a gap penalty of 10, a gap extension penalty of 0.5, and the EBLOSUM62 (EMBOSS version of BLOSUM62) substitution matrix. The Needle output labeled "longest identity" (obtained with the nobrief option) is used as the percentage identity and it is calculated as follows:

(identical residues*100)/(aligned lengths−the total number of gaps in the alignment)

In the present invention, said "identity greater than 96%" can be understood as the sequences identity of 96%, 97%, 98% or 99%. It can also may be understood as the sequences identity of 98.0%, 98.2%, 98.4%, 98.6%, 98.8%, 99.0%, 99.1%, 99.2%, 99.3% or 99.4%, but lower than 100%.

"Improved catalytic activity of the ammoniation of acrylic acid" herein means a variant showing higher catalytic activity of the ammoniation of acrylic acid than the parent (the wild type aspartase shown in sequence 2), in substrates at an elevated temperature, with increased concentration or elevated pH, after storing a period of time under conditions of industrial use or transport of those variants. The aspartase variant of the present invention may have improved catalytic activity for the ammoniation of acrylic acid compared with the parent aspartase, wherein the improved catalytic activity for the ammoniation of acrylic acid is determined as an increased relative activity. In one aspect, when comparing by the assay used to determine transamination activity in the examples, the enzyme activity of the variant with improved catalytic activity for the ammoniation of acrylic acid is at least 1.5 times, such as at least 2.0 times, at least 5 times, at least 10 times, at least 15 times, at least 20 times, at least 25 times, at least 30 times, at least 35 times, at least 45 times, or at least 55 times of that of the parent enzyme.

Further, compared with sequence 2 in the sequence listing, there are further mutations at the following positions in the amino acid sequence of the aspartase variants: positions 20, 75, 89, 156, 164, 204, 226, 258, 285, 321, 324, 381, 389, 406, 426 and/or 456, and 2, 3, 4, 5, 6, 7, 8 or 9 mutations are preferable.

Furthermore, compared with sequence 2 in the sequence listing, there are further mutations at the following positions in the amino acid sequence of the aspartase variants: D20V, V75E, Q89H, L156F, T164I, Y204C, N226I, L258I, M285L, M321I, K324I, K381R, K389I, I406L, R426C and/or P456L, and 2, 3, 4, 5, 6, 7, 8 or 9 mutations are preferable.

More specifically, compared with sequence 2 in the sequence listing, the amino acid sequence of the aspartase variants has or just has the combined mutations shown in any one of 1) to 385) as follows:
1) V75E/Q89H/T187I/L258I/N326C/K381R/K389I;
2) D20V/Q89H/L156F/T164I/T187I/Y204C/L258I/M285L/N326C/K381R/R426C;
3) Q89H/L156F/T164I/T187I/L258I/N326C/K389I/I406L/R426C;
4) L156F/T164I/T187I/L258I/K324I/N326C/K389I;
5) D20V/L156F/T164I/T187I/Y204C/N226I/M321I/K324I/N326C/K389I/R426C;
6) L156F/T187I/Y204C/K324I/N326C/K389I/I406L;
7) T187I/N226I/M285L/M321I/K32K324I/N326C/K381R/K389I/I406L/P456L;
8) D20V/Q89H/L156F/T187I/M285L/N326C/K381R/K389I;
9) D20V/Q89H/T164I/T187I/Y204C/N226I/K324I/N326C;
10) L156F/T164I/T187I/L258I/N326C/I406L/R426C;
11) V75E/T187I/N226I/L258I/K324I/N326C/K381R/I406L;
12) V75E/T187I/L258I/M285L/N326C/I406L;
13) L156F/T187I/N226I/L258I/N326C/I406L;
14) D20V/L156F/T164I/T187I/N226I/M285L/M321I/K324I/N326C/I406L/R426C;
15) V75E/T187I/N226I/M321I/K324I/N326C/P456L;
16) V75E/Q89H/L156F/T187I/N326C/K381R/R426C;
17) T187I/N226I/M321I/N326C/K389I/I406L;
18) V75E/L156F/T187I/M285L/M321I/K324I/N326C/K381R/P456L;
19) Q89H/L156F/T164I/T187I/Y204C/N226I/M285L/K324I/N326C/K381R;
20) T187I/N226I/M321I/N326C/I406L/R426C;
21) V75E/L156F/T187I/N226I/L258I/M285L/N326C;
22) V75E/Q89H/L156F/T164I/T187I/N226I/N326C/K389I/I406L;
23) Q89H/T164I/T187I/Y204C/N226I/K324I/N326C/K381R/R426C;
24) D20V/Q89H/L156F/T187I/Y204C/M285L/K324I/N326C/K381R/K389I;
25) D20V/T164I/T187I/N226I/L258I/M285L/K324I/N326C;
26) V75E/Q89H/T187I/Y204C/L258I/M321I/N326C/K381R/K389I/I406L/R426C;
27) V75E/Q89H/T164I/T187I/Y204C/N226I/M285L/M321I/N326C/K389I/R426C;
28) D20V/V75E/T187I/N226I/L258I/M285L/N326C/R426C;
29) D20V/Q89H/L156F/T187I/N226I/N326C/K381R/K389I;
30) D20V/V75E/L156F/T187I/N226I/M321I/K324I/N326C/R426C/P456L;
31) V75E/Q89H/T164I/T187I/M321I/N326C/K381R/K389I/R426C;
32) D20V/V75E/T164I/T187I/Y204C/M285L/M321I/N326C/K381R/R426C;
33) V75E/T164I/T187I/M321I/N326C/K381R/I406L;
34) V75E/L156F/T187I/Y204C/M321I/N326C/K389I/R426C;
35) T187I/M285L/N326C/I406L/R426C/P456L;
36) D20V/Q89H/T164I/T187I/M285L/N326C/K381R;
37) Q89H/T187I/Y204C/L258I/M321I/K324I/N326C/K381R/R426C;
38) V75E/Q89H/T187I/Y204C/L258I/M285L/M321I/N326C/I406L/R426C;
39) D20V/T187I/Y204C/L258I/N326C/K381R;
40) T187I/N226I/N326C/I406L/P456L;
41) D20V/L156F/T187I/L258I/M321I/K324I/N326C;
42) V75E/Q89H/L156F/T187I/M321I/N326C/R426C;

43) T187I/Y204C/N226I/M285L/M321I/N326C/K381R/K389I/I406L/P456L;
44) Q89H/T187I/N226I/M285L/M321I/K324I/N326C/K389I;
45) V75E/L156F/T164I/T187I/Y204C/N226I/L258I/N326C/I406L;
46) V75E/Q89H/L156F/T164I/T187I/Y204C/M285L/N326C/K381R/K389I/R426C;
47) D20V/V75E/L156F/T187I/N326C/K381R/R426C;
48) V75E/T187I/L258I/N326C/K381R;
49) D20V/V75E/T164I/T187I/M285L/M321I/N326C/K381R/R426C;
50) T187I/N226I/L258I/N326C/I406L;
51) V75E/T164I/T187I/M321I/N326C/I406L;
52) T187I/L258I/M285L/M321I/N326C;
53) D20V/Q89H/T187I/Y204C/L258I/M285L/N326C/K389I;
54) D20V/T187I/L258I/K324I/N326C/R426C;
55) T187I/Y204C/M285L/N326C/K381R;
56) T187I/Y204C/L258I/M285L/M321I/K324I/N326C/K381R/K389I/I406L;
57) Q89H/T187I/L258I/M285L/K324I/N326C/I406L;
58) D20V/V75E/T187I/N226I/L258I/K324I/N326C/K381R/K389I/P456L;
59) D20V/T164I/T187I/N226I/L258I/N326C/K389I;
60) T187I/Y204C/N326C/I406L/P456L;
61) D20V/T164I/T187I/L258I/M285L/K324I/N326C/I406L;
62) Q89H/T187I/M285L/N326C/K381R;
63) V75E/T187I/L258I/K324I/N326C/K389I/R426C/P456L;
64) D20V/Q89H/L156F/T187I/N226I/M32I/N326C/K381R/I406L;
65) V75E/T164I/T187I/N226I/M285L/K324I/N326C/K381R;
66) V75E/L156F/T164I/T187I/L258I/M285L/M321I/N326C/K381R/K389I/R426C;
67) V75E/T164I/T187I/L258I/M285L/M321I/N326C/K381R/K389I/I406L/R426C;
68) D20V/V75E/Q89H/T187I/L258I/M285L/M321I/N326C/K389I;
69) T187I/N326C/K381R/K389I/P456L;
70) T164I/T187I/N226I/M285L/N326C/R426C;
71) D20V/V75E/Q89H/L156F/T187I/L258I/M285L/K324I/N326C;
72) D20V/V75E/Q89H/T164I/T187I/Y204C/L258I/M285L/K324I/N326C;
73) L156F/T164I/T187I/K324I/N326C/R426C;
74) D20V/V75E/L156F/T164I/T187I/L258I/M321I/K324I/N326C/K381R/I406L;
75) D20V/T187I/N226I/L258I/N326C/I406L;
76) V75E/Q89H/L156F/T187I/M321I/K324I/N326C;
77) L156F/T164I/T187I/K324I/N326C/K381R;
78) L156F/T164I/T187I/L258I/K324I/N326C;
79) D20V/V75E/Q89H/L156F/T187I/Y204C/L258I/M321I/N326C/K389I/I406L;
80) T187I/M285L/N326C/I406L/R426C;
81) T187I/N226I/N326C/K381R/P456L;
82) D20V/T164I/T187I/Y204C/M285L/K324I/N326C/K389I/R426C;
83) V75E/T187I/N326C/K381R/I406L;
84) T187I/Y204C/N326C/K381R/K389I;
85) T187I/N226I/L258I/M285L/M321I/N326C;
86) D20V/L156F/T187I/M285L/M321I/K324I/N326C/K389I;
87) D20V/L156F/T187I/Y204C/N326C/K389I/I406L/R426C;
88) T164I/T187I/K324I/N326C/K389I/R426C;
89) V75E/Q89H/T187I/M321I/K324I/N326C/I406L;
90) V75E/T187I/L258I/N326C/K389I;
91) D20V/V75E/L156F/T187I/N326C/K389I/I406L/R426C;
92) D20V/Q89H/T164I/T187I/N226I/N326C/K389I/I406L;
93) D20V/Q89H/L156F/T164I/T187I/L258I/M285L/N326C/K381R/R426C;
94) V75E/T164I/T187I/N226I/K324I/N326C/I406L;
95) D20V/T164I/T187I/L258I/M321I/N326C/K389I;
96) T187I/N226I/M285L/N326C/K381R/K389I;
97) T187I/N226I/L258I/M285L/M321I/K324I/N326C/K381R/K389I/P456L;
98) V75E/Q89H/L156F/T187I/M321I/N326C/I406L;
99) D20V/Q89H/L156F/T164I/T187I/N226I/M321I/N326C/K389I/I406L/R426C;
100) V75E/T187I/Y204C/M285L/M321I/N326C/K381R/I406L/P456L;
101) Q89H/T164I/T187I/M285L/M321I/N326C/K381R/K389I;
102) T187I/N226I/L258I/M285L/M321I/N326C/K381R/I406L/R426C/P456L;
103) L156F/T187I/Y204C/M321I/K324I/N326C;
104) D20V/L156F/T164I/T187I/M321I/K324I/N326C;
105) T187I/Y204C/L258I/K324I/N326C;
106) T164I/T187I/N226I/M285L/M32I/K324I/N326C/K381R/I406L/R426C;
107) D20V/T164I/T187I/Y204C/N226I/N326C/K389I/I406L;
108) L156F/T187I/Y204C/N226I/M285L/M321I/N326C/I406L/R426C/P456L;
109) V75E/Q89H/L156F/T187I/K324I/N326C/K389I/R426C/P456L;
110) L156F/T164I/T187I/K324I/N326C/K381R/I406L/R426C;
111) T164I/T187I/M321I/N326C/I406L;
112) D20V/Q89H/L156F/T164I/T187I/Y204C/M285L/K324I/N326C/K381R/R426C;
113) L156F/T187I/Y204C/N326C/R426C;
114) D20V/T164I/T187I/N226I/L258I/N326C/R426C;
115) T187I/Y204C/N226I/L258I/M285L/M321I/N326C/K389I/I406L/R426C;
116) D20V/T187I/N226I/N326C/K389I;
117) V75E/Q89H/L156F/T187I/L258I/M321I/N326C/I406L/R426C;
118) T187I/Y204C/N226I/M285L/N326C/R426C;
119) T187I/Y204C/M285L/N326C/K381R/R426C;
120) L156F/T187I/N226I/N326C/K381R;
121) D20V/Q89H/T187I/Y204C/M285L/N326C/R426C;
122) L156F/T187I/L258I/M285L/M32I/K324I/N326C/K381R/I406L/R426C;
123) T187I/Y204C/L258I/M285L/K324I/N326C;
124) D20V/T187I/Y204C/N226I/L258I/N326C/I406L/R426C;
125) D20V/L156F/T187I/N226I/M285L/N326C/K381R;
126) D20V/Q89H/L156F/T187I/M285L/K324I/N326C/K389I;
127) V75E/T187I/K324I/N326C/K389I;
128) Q89H/L156F/T164I/T187I/Y204C/N226I/L258I/M285L/N326C/K389I/R426C;
129) Q89H/T187I/N226I/L258I/M321I/N326C/K381R/K389I/P456L;
130) D20V/V75E/Q89H/T187I/Y204C/M32I/K324I/N326C/K381R;
131) Q89H/T164I/T187I/M285L/N326C;
132) T187I/L258I/N326C/K381R/R426C;
133) L156F/T164I/T187I/N326C/K389I;

134) L156F/T164I/T187I/N226I/N326C/R426C;
135) D20V/Q89H/T187I/Y204C/M285L/M321I/N326C/K381R/R426C;
136) V75E/Q89H/T187I/M321I/N326C/K381R/K389I/I406L/P456L;
137) D20V/T164I/T187I/M321I/N326C/K389I/P456L;
138) Q89H/T187I/L258I/N326C/P456L;
139) V75E/L156F/T164I/T187I/L258I/M285L/N326C/K381R/K389I/R426C;
140) T187I/N226I/M285L/K324I/N326C;
141) T187I/L258I/N326C/K381R/K389I/I406L;
142) D20V/T187I/L258I/K324I/N326C/I406L;
143) V75E/L156F/T164I/T187I/Y204C/L258I/N326C/K389I/I406L;
144) D20V/Q89H/L156F/T187I/K324I/N326C/K381R/R426C;
145) Q89H/T187I/N226I/M285L/M321I/K324I/N326C;
146) T164I/T187I/M285L/M321I/N326C/K381R;
147) Q89H/L156F/T187I/Y204C/N226I/M285L/M321I/N326C/K389I/R426C;
148) Q89H/L156F/T164I/T187I/L258I/N326C/K389I;
149) T164I/T187I/N226I/M321I/K324I/N326C/K381R;
150) D20V/Q89H/T164I/T187I/Y204C/N226I/M285L/N326C/K381R/K389I/I406L;
151) V75E/T164I/T187I/L258I/N326C/K389I;
152) T187I/N326C/K389I/I406L/R426C/P456L;
153) V75E/T187I/N326C/K381R/K389I/I406L/R426C;
154) T187I/L258I/M321I/N326C/I406L;
155) Q89H/L156F/T164I/T187I/Y204C/N226I/K324I/N326C/P456L;
156) T187I/N226I/L258I/M285L/M321I/K324I/N326C/I406L/R426C/P456L;
157) D20V/T187I/M285L/N326C/K381R;
158) V75E/T187I/Y204C/M321I/N326C;
159) T164I/T187I/Y204C/L258I/K324I/N326C/K389I;
160) V75E/L156F/T164I/T187I/Y204C/L258I/M285L/M321I/N326C/K389I/I406L;
161) V75E/T164I/T187I/L258I/M285L/M321I/K324I/N326C/I406L/R426C;
162) D20V/T187I/M285L/N326C/K389I/I406L/R426C;
163) T187I/M285L/M321I/N326C/R426C;
164) Q89H/L156F/T164I/T187I/N226I/L258I/M321I/K324I/N326C;
165) Q89H/T164I/T187I/Y204C/L258I/N326C;
166) T187I/M285L/M321I/N326C/I406L/R426C;
167) D20V/L156F/T187I/M285L/M321I/K32I/324I/N326C/R426C;
168) D20V/T187I/M285L/M321I/K324I/N326C/K389I;
169) T187I/M285L/N326C/K381R/I406L/R426C;
170) V75E/Q89H/L156F/T164I/T187I/Y204C/N226I/M285L/K324I/N326C;
171) V75E/L156F/T164I/T187I/Y204C/M285L/N326C;
172) D20V/T187I/M285L/M321I/K324I/N326C/R426C;
173) T187I/Y204C/K324I/N326C/I406L/R426C;
174) V75E/Q89H/L156F/T187I/Y204C/N326C;
175) Q89H/T164I/T187I/M285L/M321I/K324I/N326C/K381R/K389I/I406L/P456L;
176) T164I/T187I/L258I/M285L/M321I/N326C/K381R/K389I/I406L/P456L;
177) T187I/L258I/N326C/I406L/R426C;
178) V75E/T164I/T187I/L258I/N326C/K381R/R426C;
179) D20V/T187I/N226I/M285L/N326C/R426C;
180) V75E/Q89H/T164I/T187I/Y204C/L258I/N326C/I406L;
181) L156F/T187I/M321I/N326C/I406L;
182) V75E/Q89H/L156F/T164I/T187I/Y204C/L258I/M285L/M321I/N326C/K389I;
183) V75E/T164I/T187I/N226I/L258I/M285L/K324I/N326C/K389I;
184) V75E/T187I/M285L/K324I/N326C/R426C;
185) D20V/Q89H/T164I/T187I/N226I/L258I/M321I/K324I/N326C/K381R/P456L;
186) V75E/Q89H/T164I/T187I/Y204C/L258I/M321I/N326C;
187) Q89H/L156F/T164I/T187I/Y204C/N226I/L258I/M285L/N326C/K389I;
188) Q89H/L156F/T187I/Y204C/N226I/M321I/K324I/N326C/K381R/I406L;
189) L156F/T187I/M285L/N326C/R426C;
190) T187I/N226I/M285L/M321I/N326C/K381R/K389I/I406L/R426C/P456L;
191) Q89H/T187I/N326C/R426C/P456L;
192) Q89H/T187I/Y204C/K324I/N326C/K389I/I406L/R426C;
193) D20V/Q89H/T164I/T187I/N226I/M285L/M321I/N326C/K381R/P456L;
194) V75E/L156F/T187I/Y204C/L258I/M321I/K324I/N326C/K381R/I406L/R426C;
195) D20V/T187I/N226I/N326C/K381R;
196) D20V/L156F/T187I/M285L/K324I/N326C/K381R/K389I;
197) Q89H/L156F/T187I/Y204C/M285L/K324I/N326C/K381R;
198) V75E/L156F/T187I/N326C/K389I/R426C;
199) T187I/Y204C/N226I/N326C/K381R;
200) T187I/Y204C/L258I/M285L/M321I/K324I/N326C/K381R/I406L/R426C;
201) T187I/L258I/K324I/N326C/K389I/I406L;
202) T187I/M321I/K324I/N326C/K381R;
203) V75E/Q89H/T164I/T187I/Y204C/N326C/K389I;
204) V75E/Q89H/T187I/N226I/N326C/K389I;
205) T187I/Y204C/M285L/N326C/P456L;
206) L156F/T187I/Y204C/K324I/N326C/K381R/R426C;
207) Q89H/T164I/T187I/M321I/N326C/I406L;
208) T164I/T187I/L156F/K324I/N326C;
209) D20V/V75E/T187I/N226I/M321I/K324I/N326C;
210) T187I/K324I/N326C/I406L/R426C/P456L;
211) T164I/T187I/K324I/N326C/R426C;
212) T164I/T187I/L258I/M285L/M321I/K324I/N326C/K381R/K389I/P456L;
213) Q89H/T164I/T187I/Y204C/N226I/L258I/M321I/N326C/R426C;
214) Q89H/T187I/N226I/M321I/N326C;
215) Q89H/L156F/T187I/Y204C/N326C/K381R/I406L/R426C/P456L;
216) D20V/T187I/M321I/K324I/N326C/K381R/I406L/R426C;
217) T187I/N226I/L258I/N326C/I406L/P456L;
218) L156F/T187I/L258I/M321I/N326C;
219) T164I/T187I/Y204C/N226I/L258I/M321I/N326C/K381R/K389I/I406L/P456L;
220) D20V/L156F/T187I/N226I/N326C;
221) V75E/Q89H/L156F/T187I/N226I/M321I/K324I/N326C/R426C;
222) D20V/T187I/Y204C/N226I/K324I/N326C/K381R/R426C;
223) Q89H/T164I/T187I/Y204C/L258I/M321I/K324I/N326C/K389I/I406L/R426C;
224) D20V/L156F/T187I/M285L/N326C;
225) V75E/T187I/Y204C/N226I/K324I/N326C/K381R/I406L;
226) V75E/T187I/M321I/I406L/N326C/R426C;
227) Q89H/T187I/L258I/N326C/R426C;

228) V75E/Q89H/L156F/T164I/T187I/Y204C/M285L/M321I/N326C/K389I;
229) L156F/T187I/Y204C/N226I/M285L/K324I/N326C/K389I/R426C/P456L;
230) T187I/N226I/M285L/N326C/R426C;
231) V75E/Q89H/T164I/T187I/L258I/M285L/M321I/N326C/K389I/R426C;
232) D20V/T187I/L258I/M321I/N326C/R426C;
233) D20V/L156F/T187I/Y204C/N226I/L258I/K324I/N326C/K381R/R426C;
234) D20V/L156F/T187I/Y204C/K324I/N326C;
235) V75E/Q89H/T187I/N326C/K389I/R426C;
236) T164I/T187I/Y204C/L258I/M321I/K324I/N326C/K389I;
237) D20V/T164I/T187I/M285L/N326C;
238) T164I/T187I/Y204C/N226I/K324I/N326C/K389I/I406L;
239) T187I/L258I/M285L/M321I/K324I/N326C/K381R/I406L;
240) T187I/Y204C/N226I/L258I/M321I/N326C/I406L;
241) V75E/T187I/N226I/N326C/K381R;
242) V75E/T187I/Y204C/N326C/I406L;
243) V75E/T187I/Y204C/N226I/M285L/K324I/N326C/K381R/R426C;
244) Q89H/T187I/M285L/N326C/R426C;
245) Q89H/T187I/K324I/N326C/K389I;
246) Q89H/T164I/T187I/K324I/N326C/K389I;
247) L156F/T187I/Y204C/L258I/M285L/M321I/N326C/K381R/K389I;
248) T187I/K324I/N326C/K381R/K389I/I406L;
249) V75E/Q89H/T164I/T187I/Y204C/M285L/N326C/K389I/R426C;
250) V75E/T187I/Y204C/N226I/L258I/N326C/I406L;
251) T187I/Y204C/N226I/K324I/N326C/R426C;
252) V75E/Q89H/L156F/T164I/T187I/M285L/N326C/K381R/K389I/R426C;
253) D20V/L156F/T187I/M321I/N326C/I406L/R426C;
254) D20V/T187I/Y204C/N226I/M285L/K324I/N326C/R426C;
255) T164I/T187I/N226I/L258I/M285L/M321I/N326C/K381R/R426C;
256) V75E/Q89H/T187I/N226I/M285L/N326C/K381R/K389I;
257) D20V/T187I/N226I/M285L/K324I/N326C/K381R/R426C;
258) T187I/Y204C/M321I/N326C/K381R;
259) V75E/T164I/T187I/N226I/L258I/N326C/K389I;
260) D20V/L156F/T164I/T187I/L258I/N326C/K381R/K389I/I406L/R426C;
261) D20V/V75E/Q89H/L156F/T164I/T187I/L258I/N326C/K381R/K389I/I406L;
262) T187I/N226I/N326C/K381R/I406L/R426C;
263) Q89H/T187I/Y204C/N326C/I406L;
264) D20V/T164I/T187I/L258I/K324I/N326C/K381R/I406L;
265) V75E/T164I/T187I/M321I/K324I/N326C/K389I/R426C/P456L;
266) Q89H/T187I/Y204C/N226I/N326C/K389I;
267) L156F/T187I/M321I/N326C/K389I/R426C;
268) Q89H/L156F/T187I/N226I/L258I/M285L/N326C/K389I/I406L/R426C;
269) Q89H/L156F/T187I/Y204C/M285L/M321I/N326C/R426C/P456L;
270) Q89H/L156F/T187I/N226I/K324I/N326C/K389I/I406L/R426C;
271) T164I/T187I/N226I/N326C/K381R;
272) V75E/Q89H/T187I/Y204C/N226I/L258I/K324I/N326C/K381R;
273) Q89H/T187I/Y204C/M321I/K324I/N326C/K381R/I406L/R426C;
274) D20V/V75E/Q89H/T164I/T187I/M285L/M321I/K324I/N326C/K381R;
275) D20V/T187I/N326C/K381R/R426C;
276) T187I/K324I/N326C/K389I/R426C;
277) Q89H/T187I/L258I/M285L/N326C/K389I/I406L;
278) D20V/T187I/M321I/N326C/I406L;
279) V75E/Q89H/T187I/L258I/M321I/N326C/I406L/R426C;
280) T187I/N226I/L258I/M321I/N326C/R426C;
281) T164I/T187I/Y204C/N226I/L258I/M321I/K324I/N326C/K381R/R426C;
282) L156F/T164I/T187I/Y204C/N326C/K381R/R426C;
283) T187I/N226I/M285L/K324I/N326C/R426C;
284) D20V/T187I/Y204C/N226I/M321I/N326C/I406L/R426C;
285) Q89H/L156F/T187I/Y204C/N226I/L258I/M285L/M321I/K324I/N326C;
286) V75E/L156F/T164I/T187I/L258I/N326C;
287) D20V/V75E/T164I/T187I/Y204C/N326C;
288) D20V/T187I/Y204C/K324I/N326C;
289) L156F/T187I/Y204C/N326C/K381R/R426C;
290) V75E/Q89H/T164I/T187I/N326C;
291) D20V/T164I/T187I/N226I/K324I/N326C;
292) T187I/N226I/L258I/M285L/M321I/K324I/N326C;
293) T187I/N226I/L258I/N326C/P456L;
294) T164I/T187I/N226I/K324I/N326C/K389I/P456L;
295) D20V/T187I/Y204C/L258I/M285L/M321I/K324I/N326C/K389I/R426C;
296) V75E/L156F/T187I/Y204C/L258I/M321I/N326C/K381R/I406L/R426C;
297) T187I/Y204C/N226I/L258I/M321I/K324I/N326C/K381R/K389I/P456L;
298) T187I/N226I/M321I/K324I/N326C;
299) V75E/T164I/T187I/N226I/L258I/M285L/N326C/K389I/I406L;
300) V75E/T187I/M285L/M321I/K324I/N326C/R426C;
301) V75E/T187I/L258I/M285L/N326C/K389I;
302) T164I/T187I/M285L/N326C/K381R/R426C;
303) T164I/T187I/N326C/K381R/I406L;
304) T164I/T187I/M285L/N326C/K389I;
305) D20V/L156F/T164I/T187I/L258I/M321I/N326C/K381R/K389I/I406L/R426C;
306) D20V/L156F/T187I/M321I/K324I/N326C/K389I/R426C/P456L;
307) T187I/N226I/L258I/N326C/K381R/R426C;
308) T187I/N226I/M285L/N326C/K389I/R426C/P456L;
309) D20V/T164I/T187I/M321I/N326C/K381R/R426C;
310) T187I/M321I/N326C/K381R/K389I/R426C;
311) T164I/T187I/Y204C/N226I/L258I/M285L/K324I/N326C/K389I;
312) Q89H/T187I/Y204C/N226I/N326C/K389I/I406L/R426C;
313) V75E/L156F/T187I/N226I/K324I/N326C/I406L/R426C;
314) Q89H/L156F/T187I/Y204C/M285L/M321I/N326C/K389I/I406L;
315) Q89H/T187I/Y204C/N326C/P456L;
316) D20V/Q89H/L156F/T187I/L258I/M321I/N326C/K381R/P456L;
317) L156F/T187I/Y204C/M321I/N326C/K389I/R426C;
318) D20V/V75E/L156F/T187I/Y204C/M285L/N326C/K381R/K389I;
319) D20V/T187I/L258I/I406L/N326C/R426C;

320) D20V/V75E/L156F/T187I/M321I/K324I/N326C/R426C/P456L;
321) T164I/T187I/N226I/L258I/M285L/M321I/K324I/N326C/K381R/K389I/P456L;
322) V75E/L156F/T187I/M285L/M321I/N326C/I406L/R426C;
323) T164I/T187I/Y204C/N226I/L258I/M285L/M321I/K324I/N326C/I406L;
324) T187I/N326C/K381R/K389I/I406L/R426C;
325) T164I/T187I/N226I/N326C/R426C;
326) V75E/T164I/T187I/N226I/M321I/N326C/K389I;
327) T187I/Y204C/N326C/R426C/P456L;
328) V75E/Q89H/T187I/Y204C/K324I/N326C/I406L;
329) D20V/T187I/N226I/L258I/N326C/K389I/I406L;
330) D20V/T164I/T187I/M285L/M321I/K324I/N326C/I406L;
331) D20V/T187I/L258I/M321I/N326C/K381R/K389I/R426C;
332) V75E/L156F/T187I/L258I/K324I/N326C;
333) V75E/T164I/T187I/Y204C/L258I/M321I/N326C/K381R/K389I/I406L;
334) D20V/V75E/Q89H/T164I/T187I/N226I/M285L/M321I/N326C/K389I/I406L;
335) V75E/Q89H/L156F/T164I/T187I/N226I/M321I/N326C/I406L;
336) D20V/T187I/N226I/L258I/N326C/I406L/R426C;
337) L156F/T187I/Y204C/K389I/N326C/R426C;
338) T187I/Y204C/L258I/M321I/N326C/R426C;
339) D20V/T187I/N326C/K389I/R426C;
340) T187I/L258I/M285L/N326C/R426C;
341) D20V/T164I/T187I/M285L/M321I/N326C/K381R/K389I/I406L;
342) Q89H/L156F/T164I/T187I/Y204C/M285L/M321I/N326C/K389I/I406L;
343) T187I/L258I/M285L/M321I/N326C/K381R;
344) T187I/L258I/N326C/K381R/I406L/R426C;
345) D20V/T164I/T187I/M321I/N326C;
346) Q89H/L156F/T164I/T187I/M285L/N326C/K389I/I406L/R426C;
347) V75E/L156F/T164I/T187I/M321I/N326C;
348) D20V/T187I/Y204C/N226I/N326C/K381R/I406L/R426C;
349) D20V/Q89H/L156F/T187I/Y204C/N226I/M285L/K324I/N326C/K381R/K389I;
350) D20V/V75E/Q89H/L156F/T187I/Y204C/M285L/M321I/N326C/K389I;
351) D20V/T164I/T187I/N226I/L258I/N326C/K381R/K389I;
352) L156F/T164I/T187I/Y204C/N226I/L258I/M321I/K324I/N326C;
353) V75E/Q89H/T164I/T187I/N326C/K381R/K389I;
354) L156F/T187I/N226I/L258I/M285L/M321I/N326C/K381R/K389I/I406L;
355) Q89H/T164I/T187I/Y204C/L258I/N326C/K381R;
356) D20V/Q89H/T187I/L258I/N326C;
357) V75E/L156F/T187I/M285L/N326C/K389I;
358) Q89H/L156F/T187I/Y204C/N226I/L258I/N326C/K389I/I406L/R426C;
359) D20V/V75E/L156F/T164I/T187I/Y204C/M285L/N326C/K381R/K389I;
360) V75E/Q89H/L156F/T164I/T187I/N226I/N326C/I406L;
361) T187I/M285L/N326C/K381R/K389I/P456L;
362) V75E/Q89H/T164I/T187I/M321I/K324I/N326C/K381R/I406L;
363) Q89H/L156F/T187I/L258I/M321I/K324I/N326C;
364) T187I/L258I/M285L/N326C/K389I;
365) T187I/Y204C/N226I/L258I/N326C/R426C;
366) V75E/Q89H/T164I/T187I/Y204C/M285L/N326C/R426C;
367) T187I/Y204C/N226I/L258I/N326C;
368) D20V/L156F/T164I/T187I/N226I/L258I/M285L/N326C/I406L/R426C;
369) T187I/Y204C/L258I/N326C/K381R;
370) D20V/T187I/N326C/K381R/I406L;
371) D20V/V75E/T187I/N226I/K324I/N326C/K381R/K389I/P456L;
372) D20V/Q89H/T187I/L258I/M321I/K324I/N326C/K389I;
373) T164I/T187I/Y204C/M285L/N326C/R426C;
374) L156F/T187I/Y204C/N326C/K381R;
375) T187I/L258I/N326C/K389I/I406L/R426C;
376) L156F/T187I/M285L/N326C/K389I;
377) D20V/T164I/T187I/L258I/K324I/N326C;
378) V75E/L156F/T164I/T187I/Y204C/N226I/L258I/M285L/M321I/K324I/N326C;
379) V75E/T187I/M285L/K324I/N326C/K381R/R426C;
380) V75E/T187I/N226I/M285L/N326C;
381) Q89H/L156F/T187I/N326C/K381R;
382) D20V/T187I/K324I/N326C/I406L;
383) D20V/T187I/M321I/N326C/K389I;
384) V75E/L156F/T187I/N326C/R426C;
385) T187I/Y204C/N326C/I406L/R426C.

With respect to the present invention, the mature polypeptide included in sequence 2 is used to determine the corresponding amino acid residues in the variant aspartase. The amino acid sequence of the variant aspartase was aligned with the mature polypeptide disclosed in sequence 2. Then, based on this alignment, the numbering of any amino acid residue in the variant aspartase, corresponding to the mature polypeptide disclosed in sequence 2, can be determined by the Needleman-Wunsch algorithm (Needleman and Wunsch, 1970, J. Mol. Biol. 48: 443-453) performed in the EMBOSS package (EMBOSS: The European Molecular Biology Open Software Suite and the Needle program (preferred version 5.0.0 or later) of Rice et al., 2000, Trends Genet. 16: 276-277. The parameters used are a gap penalty of 10, a gap extension penalty of 0.5, and the EBLOSUM62 (EMBOSS version of BLOSUM62) substitution matrix.

Substitution: for amino acid substitution, the following nomenclature is used: original amino acid, position, substituted amino acid. Accordingly, the substitution of tryptophan with glycine at position 168 was named "Trp168Gly" or "W168G". For base substitution, the following nomenclature is used: original base, position, substituted base. Accordingly, the substitution of cytosine C with thymine T at position 60 is named C60T.

Deletion: for amino acid deletion, the following nomenclature is used: "Δ", original amino acid, position. Accordingly, the deletion of glycine at position 195 is named "ΔGly195" or "ΔG195".

Insertion: for amino acid insertions, the following nomenclature is used: original amino acid, position, original amino acid, inserted amino acid. Accordingly, the insertion of lysine after the glycine at position 195 is named "Gly195GlyLys" or "G195GK.

Multiple changes: variations containing multiple changes are separated by a slash ("/"), for example: "Arg170Tyr/Gly195Glu" or "R170Y/G195E" represents the substitution of tyrosine and glutamic acid at positions 170 and 195 with arginine and glycine, respectively; C560T/G561T represents the substitution of cytosine C and guanine G at positions 560 and 561 with thymine T and thymine T, respectively.

The nomenclature used for determining the amino acid position used herein is based on the amino acid sequence of aspartase derived from *Bacillus*, and its mature polypeptide sequence is shown as amino acid residues 1-468 of sequence 2 in the sequence listing. Accordingly, in the context herein, the numbered position is based on sequence 2, starting with M1 and ending with K468.

In order to facilitate the purification of the aspartase variant, a tag as shown in the following table may be attached to the amino terminus or carboxy terminus of the aspartase variant.

TABLE sequences of tags

| Tags | Residues | Sequences |
| --- | --- | --- |
| Poly-Arg | 5-6 (Generally 5) | RRRRR |
| Poly-His | 2-10 (Generally 6) | HHHHHH |
| FLAG | 8 | DYKDDDDK |
| Strep-tag II | 8 | WSHPQFEK |
| c-myc | 10 | EQKLISEEDL |

A nucleic acid molecule encoding the aspartase variant also falls into the protection scope of the present invention.

The nucleic acid molecule may be DNA, such as cDNA, genomic DNA, or recombinant DNA. The nucleic acid molecule may also be RNA, such as mRNA, hnRNA, or tRNA, and the like.

In the present invention, the nucleic acid molecule is a gene encoding the aspartase variant, and compared with sequence 1 in the sequence listing, the nucleotide sequence of the gene has or just has the combined mutations shown in any one of 1)-385) as follows:

1) T224A/C560T/G561T/T772A/A774T/A976T/A977G/ T978C/A1166T/A1167C;
2) T224A/C560T/G561T/T772A/A774T/A976T/A977G/ T978C/A1141C/A1142G/A 1143T;
3) T224A/C560T/G561T/T772A/A774T/A971T/A972T/ A976T/A977G/T978C/A1166T/A1167C/C1276T/T1278C/ C1366T/C1367T/A1368G;
4) T224A/C560T/G561T/T772A/A774T/A853C/A976T/ A977G/T978C/A1216T/T1218G;
5) T224A/C560T/G561T/T772A/A774T/A853C/A976T/ A977G/T978C/A1166T/A1167C;
6) T224A/C560T/G561T/G963T/A1216T/T1218G/A976T/ A977G/T978C/C1276T/T 1278C;
7) T224A/C560T/G561T/A976T/A977G/T978C/A1141C/ A1142G/A1143T/A1216T/T 1218G;
8) T224A/C560T/G561T/A976T/A977G/T978C/A1141C/ A1142G/A1143T/A1166T/A 1167C/A1216T/T1218G/ C1276T/T1278C;
9) T224A/C560T/G561T/A971T/A972T/A976T/A977G/ T978C/A1166T/A1167C;
10) T224A/C560T/G561T/A853C/G963T/A971T/A972T/ A976T/A977G/T978C/C1276T/T1278C;
11) T224A/C560T/G561T/A853C/A971T/A972T/A976T/ A977G/T978C/C1276T/T 1278C;
12) T224A/C560T/G561T/A853C/A971T/A972T/A976T/ A977G/T978C/A1141C/A 1142G/A1143T/C1276T/ T1278C;
13) T224A/C560T/G561T/A677T/C678T/T772A/A774T/ A971T/A972T/A976T/A977G/T978C/A1141C/A1142G/ A1143T/A1216T/T1218G;
14) T224A/C560T/G561T/A677T/C678T/G963T/A971T/ A972T/A976T/A977G/T978C/C1366T/C1367T/A1368G;
15) T224A/C560T/G561T/A677T/C678T/A976T/A977G/ T978C/A1141C/A1142G/A 1143T;
16) T224A/C560T/G561T/A677T/C678T/A853C/A976T/ A977G/T978C;
17) T224A/C560T/G561T/A611G/T612C/G963T/A976T/ A977G/T978C;
18) T224A/C560T/G561T/A611G/T612C/A976T/A977G/ T978C/A1216T/T1218G;
19) T224A/C560T/G561T/A611G/T612C/A853C/G963T/ A976T/A977G/T978C/A1141C/A1142G/A1143T/A1216T/ T1218G/C1366T/C1367T/A1368G;
20) T224A/C560T/G561T/A611G/T612C/A677T/C678T/ T772A/A774T/A976T/A977G/T978C/A1216T/T1218G;
21) T224A/C560T/G561T/A611G/T612C/A677T/C678T/ A971T/A972T/A976T/A977G/T978C/A1141C/A1142G/ A1143T/A1216T/T1218G;
22) T224A/C560T/G561T/A611G/T612C/A677T/C678T/ A853C/A971T/A972T/A976T/A977G/T978C/A1141C/ A1142G/A1143T/C1276T/T1278C;
23) T224A/C491T/A492T/C560T/G561T/T772A/A774T/ A976T/A977G/T978C/A1166T/A1167C;
24) T224A/C491T/A492T/C560T/G561T/T772A/A774T/ A976T/A977G/T978C/A1141C/A1142G/A1143T/C1276T/ T1278C;
25) T224A/C491T/A492T/C560T/G561T/T772A/A774T/ A853C/G963T/A976T/A977G/T978C/A1141C/A42G/ A1143T2G/A1166T/A166T/A1167C/A1216T/T1218G/ C1276T/T 1278C;
26) T224A/C491T/A492T/C560T/G561T/T772A/A774T/ A853C/G963T/A971T/A972T/A976T/A977G/T978C/ A1216T/T1218G/C1276T/T1278C;
27) T224A/C491T/A492T/C560T/G561T/G963T/A976T/ A977G/T978C/A1216T/T 1218G;
28) T224A/C491T/A492T/C560T/G561T/G963T/A976T/ A977G/T978C/A1141C/A 1142G/A1143T/A1216T/ T1218G;
29) T224A/C491T/A492T/C560T/G561T/G963T/A971T/ A972T/A976T/A977G/T978C/A1166T/A1167C/C1276T/ T1278C/C1366T/C1367T/A1368G;
30) T224A/C491T/A492T/C560T/G561T/A677T/C678T/ T772A/A774T/A976T/A977G/T978C/A1166T/A1167C;
31) T224A/C491T/A492T/C560T/G561T/A677T/C678T/ T772A/A774T/A853C/A976T/A977G/T978C/A1166T/ A1167C/A1216T/T1218G;
32) T224A/C491T/A492T/C560T/G561T/A677T/C678T/ T772A/A774T/A853C/A971T/A972T/A976T/A977G/ T978C/A1166T/A1167C;
33) T224A/C491T/A492T/C560T/G561T/A677T/C678T/ G963T/A976T/A977G/T978C/A1166T/A1167C;
34) T224A/C491T/A492T/C560T/G561T/A677T/C678T/ A971T/A972T/A976T/A977G/T978C/A1216T/T1218G;
35) T224A/C491T/A492T/C560T/G561T/A677T/C678T/ A853C/A971T/A972T/A976T/A977G/T978C/A1141C/ A1142G/A1143T;
36) T224A/C491T/A492T/C560T/G561T/A611G/T612C/ T772A/A774T/G963T/A976T/A977G/T978C/A1141C/ A1142G/A1143T/A1166T/A1167C/A1216T/T1218G;
37) T224A/A468T/C560T/G561T/T772A/A774T/A971T/ A972T/A976T/A977G/T978C;
38) T224A/A468T/C560T/G561T/A976T/A977G/T978C/ C1276T/T1278C;
39) T224A/A468T/C560T/G561T/A976T/A977G/T978C/ A1166T/A1167C/C1276T/T 1278C;
40) T224A/A468T/C560T/G561T/A853C/G963T/A976T/ A977G/T978C/A1216T/T 1218G/C1276T/T1278C;

41) T224A/A468T/C560T/G561T/A853C/G963T/A971T/ A972T/A976T/A977G/T978C/A1141C/A1142G/A1143T/ C1366T/C1367T/A1368G;
42) T224A/A468T/C560T/G561T/A853C/A976T/A977G/ T978C/A1166T/A1167C;
43) T224A/A468T/C560T/G561T/A677T/C678T/T772A/ A774T/A853C/A976T/A977G/T978C;
44) T224A/A468T/C560T/G561T/A677T/C678T/A971T/ A972T/A976T/A977G/T978C/A1216T/T1218G/C1276T/ T1278C;
45) T224A/A468T/C560T/G561T/A611G/T612C/T772A/ A774T/G963T/A976T/A977G/T978C/A1141C/A1142G/ A1143T/A1216T/T1218G/C1276T/T1278C;
46) T224A/A468T/C560T/G561T/A611G/T612C/T772A/ A774T/G963T/A971T/A972T/A976T/A977G/T978C/ A1141C/A1142G/A1143T/A1216T/T1218G/C1276T/ T1278C;
47) T224A/A468T/C560T/G561T/A611G/T612C/G963T/ A976T/A977G/T978C/A1166T/A1167C/C1276T/T1278C;
48) T224A/A468T/C491T/A492T/C560T/G561T/T772A/ A774T/A976T/A977G/T978C;
49) T224A/A468T/C491T/A492T/C560T/G561T/T772A/ A774T/A853C/G963T/A976T/A977G/T978C/A1141C/ A1142G/A1143T/A1166T/A1167C/C1276T/T1278C;
50) T224A/A468T/C491T/A492T/C560T/G561T/T772A/ A774T/A853C/A976T/A977G/T978C/A1141C/A1142G/ A1143T/A1166T/A1167C/C1276T/T1278C;
51) T224A/A468T/C491T/A492T/C560T/G561T/G963T/ A976T/A977G/T978C;
52) T224A/A468T/C491T/A492T/C560T/G561T/A611G/ T612C/T772A/A774T/A976T/A977G/T978C/A1166T/ A1167C/A1216T/T1218G;
53) T224A/A468T/C491T/A492T/C560T/G561T/A611G/ T612C/T772A/A774T/A853C/G963T/A976T/A977G/ T978C/A1166T/A1167C/A1216T/T1218G;
54) T224A/A468T/C491T/A492T/C560T/G561T/A611G/ T612C/A853C/A976T/A977G/T978C;
55) T224A/A468T/C491T/A492T/C560T/G561T/A611G/ T612C/A677T/C678T/T772A/A774T/A976T/A977G/ T978C/A1216T/T1218G;
56) T224A/A468T/C491T/A492T/C560T/G561T/A611G/ T612C/A677T/C678T/T772A/A774T/A853C/G963T/ A971T/A972T/A976T/A977G/T978C;
57) T224A/A267T/C560T/G561T/T772A/A774T/G963T/ A976T/A977G/T978C/A1216T/T1218G/C1276T/T1278C;
58) T224A/A267T/C560T/G561T/T772A/A774T/A976T/ A977G/T978C/A1141C/A1142G/A1143T/A1166T/ A1167C;
59) T224A/A267T/C560T/G561T/G963T/A976T/A977G/ T978C/A1141C/A1142G/A1143T/A1166T/A1167C/ A1216T/T1218G/C1366T/C1367T/A1368G;
60) T224A/A267T/C560T/G561T/G963T/A971T/A972T/ A976T/A977G/T978C/A1216T/T1218G;
61) T224A/A267T/C560T/G561T/A976T/A977G/T978C/ A1166T/A1167C/C1276T/T1278C;
62) T224A/A267T/C560T/G561T/A677T/C678T/A976T/ A977G/T978C/A1166T/A1167C;
63) T224A/A267T/C560T/G561T/A611G/T612C/T772A/ A774T/G963T/A976T/A977G/T978C/A1141C/A42G/ A1143T2G/A1166T/A166T/A1167C/A1216T/T1218G/ C1276T/T1278C;
64) T224A/A267T/C560T/G561T/A611G/T612C/T772A/ A774T/A853C/G963T/A976T/A977G/T978C/A1216T/ T1218G/C1276T/T1278C;
65) T224A/A267T/C560T/G561T/A611G/T612C/A971T/ A972T/A976T/A977G/T978C/A1216T/T1218G;
66) T224A/A267T/C560T/G561T/A611G/T612C/A677T/ C678T/T772A/A774T/A971T/A972T/A976T/A977G/ T978C/A1141C/A1142G/A1143T;
67) T224A/A267T/C491T/A492T/C560T/G561T/T772A/ A774T/A853C/G963T/A976T/A977G/T978C/A1166T/ A1167C/C1276T/T1278C;
68) T224A/A267T/C491T/A492T/C560T/G561T/G963T/ A976T/A977G/T978C/A1141C/A1142G/A1143T/A1166T/ A1167C/C1276T/T1278C;
69) T224A/A267T/C491T/A492T/C560T/G561T/G963T/ A971T/A972T/A976T/A977G/T978C/A1141C/A1142G/ A1143T/A1216T/T1218G;
70) T224A/A267T/C491T/A492T/C560T/G561T/A976T/ A977G/T978C/A1141C/A1142G/A1143T/A1166T/ A1167C;
71) T224A/A267T/C491T/A492T/C560T/G561T/A976T/ A977G/T978C;
72) T224A/A267T/C491T/A492T/C560T/G561T/A611G/ T612C/T772A/A774T/G963T/A976T/A977G/T978C;
73) T224A/A267T/C491T/A492T/C560T/G561T/A611G/ T612C/T772A/A774T/A976T/A977G/T978C/A1216T/ T1218G;
74) T224A/A267T/C491T/A492T/C560T/G561T/A611G/ T612C/A976T/A977G/T978C/A1166T/A1167C;
75) T224A/A267T/C491T/A492T/C560T/G561T/A611G/ T612C/A853C/A976T/A977G/T978C/C1276T/T1278C;
76) T224A/A267T/C491T/A492T/C560T/G561T/A611G/ T612C/A853C/A976T/A977G/T978C/A1166T/A1167C/ C1276T/T1278C;
77) T224A/A267T/C491T/A492T/C560T/G561T/A611G/ T612C/A677T/C678T/A853C/G963T/A976T/A977G/ T978C/A1166T/A1167C/C1276T/T1278C;
78) T224A/A267T/A468T/C560T/G561T/T772A/A774T/ G963T/A976T/A977G/T978C/A1216T/T1218G/C1276T/ T1278C;
79) T224A/A267T/A468T/C560T/G561T/G963T/A976T/ A977G/T978C/C1276T/T 1278C;
80) T224A/A267T/A468T/C560T/G561T/G963T/A976T/ A977G/T978C/A1216T/T 1218G;
81) T224A/A267T/A468T/C560T/G561T/G963T/A971T/ A972T/A976T/A977G/T978C;
82) T224A/A267T/A468T/C560T/G561T/A976T/A977G/ T978C/A1141C/A1142G/A 1143T/C1276T/T1278C;
83) T224A/A267T/A468T/C560T/G561T/A971T/A972T/ A976T/A977G/T978C/A1166T/A1167C/C1276T/T1278C/ C1366T/C1367T/A1368G
84) T224A/A267T/A468T/C560T/G561T/A677T/C678T/ G963T/A971T/A972T/A976T/A977G/T978C/C1276T/ T1278C;
85) T224A/A267T/A468T/C560T/G561T/A677T/C678T/ A853C/A976T/A977G/T978C/A1141C/A1142G/A1143T/ A1166T/A1167C;
86) T224A/A267T/A468T/C560T/G561T/A611G/T612C/ A976T/A977G/T978C;
87) T224A/A267T/A468T/C491T/A492T/C560T/G561T/ A853C/A976T/A977G/T978C/A1141C/A1142G/A1143T/ A1166T/A1167C/C1276T/T1278C;
88) T224A/A267T/A468T/C491T/A492T/C560T/G561T/ A677T/C678T/G963T/A976T/A977G/T978C/A1216T/ T1218G;
89) T224A/A267T/A468T/C491T/A492T/C560T/G561T/ A677T/C678T/A976T/A977G/T978C/A1216T/T1218G;
90) T224A/A267T/A468T/C491T/A492T/C560T/G561T/ A677T/C678T/A976T/A977G/T978C/A1166T/A1167C/ A1216T/T1218G;

91) T224A/A267T/A468T/C491T/A492T/C560T/G561T/ A611G/T612C/T772A/A774T/A853C/G963T/A976T/ A977G/T978C/A1166T/A1167C;
92) T224A/A267T/A468T/C491T/A492T/C560T/G561T/ A611G/T612C/A853C/G963T/A976T/A977G/T978C/ A1166T/A1167C;
93) T224A/A267T/A468T/C491T/A492T/C560T/G561T/ A611G/T612C/A853C/A976T/A977G/T978C/A1141C/ A1142G/A1143T/A1166T/A1167C/C1276T/T1278C;
94) T224A/A267T/A468T/C491T/A492T/C560T/G561T/ A611G/T612C/A677T/C678T/A853C/A971T/A972T/ A976T/A977G/T978C;
95) C560T/G561T/T772A/A774T/G963T/A976T/A977G/ T978C/A1216T/T1218G;
96) C560T/G561T/T772A/A774T/A976T/A977G/T978C/ A1216T/T1218G/C1276T/T1278C;
97) C560T/G561T/T772A/A774T/A976T/A977G/T978C/ A1166T/A1167C/A1216T/T1218G/C1276T/T1278C;
98) C560T/G561T/T772A/A774T/A976T/A977G/T978C/ A1141C/A1142G/A1143T/C1276T/T1278C;
99) C560T/G561T/T772A/A774T/A976T/A977G/T978C/ A1141C/A1142G/A1143T/A1216T/T1218G/C1276T/ T1278C;
100) C560T/G561T/T772A/A774T/A976T/A977G/T978C/ A1141C/A1142G/A1143T/A1166T/A1167C/A1216T/ T1218G;
101) C560T/G561T/T772A/A774T/A971T/A972T/A976T/ A977G/T978C/A1166T/A1167C/A1216T/T1218G;
102) C560T/G561T/T772A/A774T/A853C/G963T/A976T/ A977G/T978C/A1141C/A1142G/A1143T;
103) C560T/G561T/T772A/A774T/A853C/G963T/A976T/ A977G/T978C;
104) C560T/G561T/T772A/A774T/A853C/G963T/A971T/ A972T/A976T/A977G/T978C/A1141C/A1142G/A1143T/ A1216T/T1218G;
105) C560T/G561T/T772A/A774T/A853C/A976T/A977G/ T978C/C1276T/T1278C;
106) C560T/G561T/T772A/A774T/A853C/A976T/A977G/ T978C/A1166T/A1167C;
107) C560T/G561T/G963T/A976T/A977G/T978C/ A1141C/A1142G/A1143T/A1166T/A1167C/C1276T/ T1278C;
108) C560T/G561T/G963T/A971T/A972T/A976T/A977G/ T978C/A1141C/A1142G/A1143T;
109) C560T/G561T/A976T/A977G/T978C/A1166T/ A1167C/A1216T/T1218G/C1276T/T1278C/C1366T/ C1367T/A1368G;
110) C560T/G561T/A976T/A977G/T978C/A1141C/ A1142G/A1143T/A1166T/A1167C/C1366T/C1367T/ A1368G;
111) C560T/G561T/A976T/A977G/T978C/A1141C/ A1142G/A1143T/A1166T/A1167C/A1216T/T1218G/ C1276T/T1278C;
112) C560T/G561T/A971T/A972T/A976T/A977G/T978C/ A1216T/T1218G/C1276T/T1278C/C1366T/C1367T/ A1368G;
113) C560T/G561T/A971T/A972T/A976T/A977G/T978C/ A1166T/A1167C/C1276T/T1278C;
114) C560T/G561T/A971T/A972T/A976T/A977G/T978C/ A1141C/A1142G/A1143T/A1166T/A1167C/A1216T/ T1218G;
115) C560T/G561T/A853C/G963T/A976T/A977G/T978C/ C1276T/T1278C;
116) C560T/G561T/A853C/G963T/A976T/A977G/T978C/ A1216T/T1218G/C1276T/T1278C;
117) C560T/G561T/A853C/A976T/A977G/T978C/ A1216T/T1218G/C1276T/T1278C/C1366T/C1367T/ A1368G;
118) C560T/G561T/A853C/A976T/A977G/T978C/ A1216T/T1218G/C1276T/T1278C;
119) C560T/G561T/A853C/A976T/A977G/T978C/ A1141C/A1142G/A1143T/A1216T/T1218G/C1276T/ T1278C;
120) C560T/G561T/A853C/A976T/A977G/T978C/ A1141C/A1142G/A1143T/A1166T/A1167C/C1366T/ C1367T/A1368G;
121) C560T/G561T/A677T/C678T/T772A/A774T/G963T/ A976T/A977G/T978C/C1276T/T1278C;
122) C560T/G561T/A677T/C678T/T772A/A774T/A976T/ A977G/T978C/C1366T/C1367T/A1368G;
123) C560T/G561T/A677T/C678T/T772A/A774T/A976T/ A977G/T978C/A1216T/T1218G/C1366T/C1367T/ A1368G;
124) C560T/G561T/A677T/C678T/T772A/A774T/A976T/ A977G/T978C/A1216T/T1218G;
125) C560T/G561T/A677T/C678T/T772A/A774T/A976T/ A977G/T978C/A1141C/A1142G/A1143T/C1276T/ T1278C;
126) C560T/G561T/A677T/C678T/T772A/A774T/A853C/ G963T/A976T/A977G/T978C/A1141C/A1142G/A1143T/ A1216T/T1218G/C1276T/T1278C/C1366T/C1367T/ A1368G;
127) C560T/G561T/A677T/C678T/T772A/A774T/A853C/ G963T/A976T/A977G/T978C;
128) C560T/G561T/A677T/C678T/T772A/A774T/A853C/ G963T/A971T/A972T/A976T/A977G/T978C/A1216T/ T1218G/C1276T/T1278C/C1366T/C1367T/A1368G;
129) C560T/G561T/A677T/C678T/T772A/A774T/A853C/ G963T/A971T/A972T/A976T/A977G/T978C/A1141C/ A1141C/A1142G/A1143T/A1166T/A1167C/C1366T/ C1367T/A1368G;
130) C560T/G561T/A677T/C678T/T772A/A774T/A853C/ G963T/A971T/A972T/A976T/A977G/T978C;
131) C560T/G561T/A677T/C678T/G963T/A976T/A977G/ T978C/A1216T/T1218G/C1276T/T1278C;
132) C560T/G561T/A677T/C678T/G963T/A976T/A977G/ T978C/A1166T/A1167C/A1216T/T1218G;
133) C560T/G561T/A677T/C678T/G963T/A971T/A972T/ A976T/A977G/T978C;
134) C560T/G561T/A677T/C678T/A976T/A977G/T978C/ A1216T/T1218G/C1366T/C1367T/A1368G;
135) C560T/G561T/A677T/C678T/A976T/A977G/T978C/ A1141C/A1142G/A1143T/C1366T/C1367T/A1368G;
136) C560T/G561T/A677T/C678T/A976T/A977G/T978C/ A1141C/A1142G/A1143T/A1216T/T1218G/C1276T/ T1278C;
137) C560T/G561T/A677T/C678T/A853C/G963T/A976T/ A977G/T978C/A1141C/A1142G/A1143T/A1166T/ A1167C/A1216T/T1218G/C1276T/T1278C/C1366T/ C1367T/A1368G;
138) C560T/G561T/A677T/C678T/A853C/G963T/A971T/ A972T/A976T/A977G/T978C/A1141C/A1142G/A1143T/ A1166T/A1167C/A1216T/T1218G/C1366T/C1367T/ A1368G;
139) C560T/G561T/A677T/C678T/A853C/A976T/A977G/ T978C/C1276T/T1278C;
140) C560T/G561T/A677T/C678T/A853C/A976T/A977G/ T978C/A166T/A1167C/C1276T/T1278C/C1366T/ C1367T/A1368G;
141) C560T/G561T/A677T/C678T/A853C/A976T/A977G/ T978C/A1141C/A1142G/A1143T/A1166T/A1167C;

142) C560T/G561T/A677T/C678T/A853C/A971T/A972T/A976T/A977G/T978C/C 1276T/T1278C;
143) C560T/G561T/A677T/C678T/A853C/A971T/A972T/A976T/A977G/T978C;
144) C560T/G561T/A611G/T612C/T772A/A774T/G963T/A976T/A977G/T978C/C 1276T/T1278C;
145) C560T/G561T/A611G/T612C/T772A/A774T/A976T/A977G/T978C/A1141C/A 1142G/A1143T;
146) C560T/G561T/A611G/T612C/T772A/A774T/A971T/A972T/A976T/A977G/T 978C;
147) C560T/G561T/A611G/T612C/T772A/A774T/A853C/G963T/A971T/A972T/A 976T/A977G/T978C/A1141C/A1142G/A1143T/A1216T/T1218G/C1276T/T1278C;
148) C560T/G561T/A611G/T612C/T772A/A774T/A853C/G963T/A971T/A972T/A 976T/A977G/T978C/A1141C/A1142G/A1143T/A1166T/A1167C/A1216T/T1218G;
149) C560T/G561T/A611G/T612C/T772A/A774T/A853C/A971T/A972T/A976T/A 977G/T978C;
150) C560T/G561T/A611G/T612C/G963T/A976T/A977G/T978C/A1141C/A1142G/A 1143T;
151) C560T/G561T/A611G/T612C/A976T/A977G/T978C/C1276T/T1278C/C1366T/C1367T/A1368G;
152) C560T/G561T/A611G/T612C/A976T/A977G/T978C/A1216T/T1218G/C1276T/T1278C;
153) C560T/G561T/A611G/T612C/A976T/A977G/T978C/A1216T/T1218G/C1366T/C1367T/A1368G;
154) C560T/G561T/A611G/T612C/A976T/A977G/T978C/A1141C/A1142G/A1143T/A1166T/A1167C;
155) C560T/G561T/A611G/T612C/A971T/A972T/A976T/A977G/T978C/A1216T/T 1218G/C1276T/T1278C;
156) C560T/G561T/A611G/T612C/A853C/A976T/A977G/T978C/C1366T/C1367T/A 1368G;
157) C560T/G561T/A611G/T612C/A853C/A976T/A977G/T978C/A1141C/A1142G/A 1143T/C1276T/T1278C;
158) C560T/G561T/A611G/T612C/A853C/A976T/A977G/T978C/A1141C/A1142G/A 1143T;
159) C560T/G561T/A611G/T612C/A677T/C678T/T772A/A774T/G963T/A976T/A 977G/T978C/A1216T/T1218G;
160) C560T/G561T/A611G/T612C/A677T/C678T/T772A/A774T/G963T/A971T/A 972T/A976T/A977G/T978C/A1141C/A1142G/A1143T/A1166T/A1167C/C1366T/C 1367T/A1368G;
161) C560T/G561T/A611G/T612C/A677T/C678T/T772A/A774T/A976T/A977G/T 978C/C1276T/T1278C;
162) C560T/G561T/A611G/T612C/A677T/C678T/T772A/A774T/A976T/A977G/T 978C;
163) C560T/G561T/A611G/T612C/A677T/C678T/T772A/A774T/A853C/G963T/A 976T/A977G/T978C/A1166T/A1167C/A1216T/T1218G/C1276T/T1278C;
164) C560T/G561T/A611G/T612C/A677T/C678T/A976T/A977G/T978C/A1141C/A 1142G/A1143T;
165) C560T/G561T/A611G/T612C/A677T/C678T/A971T/A972T/A976T/A977G/T 978C/C1276T/T1278C;
166) C560T/G561T/A611G/T612C/A677T/C678T/A853C/G963T/A976T/A977G/T 978C/A1141C/A1142G/A1143T/A1166T/A1167C/A1216T/T1218G/C1366T/C1367T/A1368G;
167) C560T/G561T/A611G/T612C/A677T/C678T/A853C/A976T/A977G/T978C/C 1276T/T1278C;
168) C491T/A492T/C560T/G561T/T772A/A774T/A853C/G963T/A976T/A977G/T 978C/A1141C/A1142G/A1143T/A1166T/A1167C/A1216T/T1218G/C1366T/C1367T/A1368G;
169) C491T/A492T/C560T/G561T/T772A/A774T/A853C/G963T/A971T/A972T/A 976T/A977G/T978C/A1141C/A1142G/A1143T/A1166T/A1167C/C1366T/C1367T/A 1368G;
170) C491T/A492T/C560T/G561T/G963T/A976T/A977G/T978C/A1216T/T1218G;
171) C491T/A492T/C560T/G561T/A976T/A977G/T978C/A1141C/A1142G/A1143T/A1216T/T1218G;
172) C491T/A492T/C560T/G561T/A971T/A972T/A976T/A977G/T978C/C1276T/T 1278C;
173) C491T/A492T/C560T/G561T/A971T/A972T/A976T/A977G/T978C/A1166T/A 1167C/C1276T/T1278C;
174) C491T/A492T/C560T/G561T/A853C/G963T/A976T/A977G/T978C/A1141C/A 1142G/A1143T;
175) C491T/A492T/C560T/G561T/A853C/A976T/A977G/T978C/A1166T/A1167C;
176) C491T/A492T/C560T/G561T/A853C/A976T/A977G/T978C/A1141C/A1142G/A 1143T/C1276T/T1278C;
177) C491T/A492T/C560T/G561T/A677T/C678T/T772A/A774T/A853C/G963T/A 976T/A977G/T978C/A1141C/A1142G/A1143T/C1276T/T1278C;
178) C491T/A492T/C560T/G561T/A677T/C678T/T772A/A774T/A853C/G963T/A 971T/A972T/A976T/A977G/T978C/A1141C/A1142G/A1143T/A1166T/A1167C/C1366T/C1367T/A1368G;
179) C491T/A492T/C560T/G561T/A677T/C678T/G963T/A971T/A972T/A976T/A 977G/T978C/A1141C/A1142G/A1143T;
180) C491T/A492T/C560T/G561T/A677T/C678T/A976T/A977G/T978C/C1276T/T 1278C;
181) C491T/A492T/C560T/G561T/A677T/C678T/A976T/A977G/T978C/A1141C/A 1142G/A1143T;
182) C491T/A492T/C560T/G561T/A677T/C678T/A971T/A972T/A976T/A977G/T 978C/A1166T/A1167C/C1366T/C1367T/A1368G;
183) C491T/A492T/C560T/G561T/A677T/C678T/A853C/G963T/A971T/A972T/A 976T/A977G/T978C/A1141C/A1142G/A1143T/A1216T/T1218G/C1276T/T1278C;
184) C491T/A492T/C560T/G561T/A677T/C678T/A853C/A976T/A977G/T978C/C 1276T/T1278C;
185) C491T/A492T/C560T/G561T/A611G/T612C/T772A/A774T/G963T/A971T/A 972T/A976T/A977G/T978C/A1166T/A1167C;
186) C491T/A492T/C560T/G561T/A611G/T612C/T772A/A774T/A971T/A972T/A 976T/A977G/T978C/A1166T/A1167C;
187) C491T/A492T/C560T/G561T/A611G/T612C/A853C/A976T/A977G/T978C/C 1276T/T1278C;
188) C491T/A492T/C560T/G561T/A611G/T612C/A677T/C678T/T772A/A774T/G 963T/A976T/A977G/T978C/A1141C/A1142G/A1143T/A1166T/A1167C/A1216T/T 1218G/C1366T/C1367T/A1368G;
189) C491T/A492T/C560T/G561T/A611G/T612C/A677T/C678T/T772A/A774T/G 963T/A971T/A972T/A976T/A977G/T978C/A1141C/A1142G/A1143T/C1276T/T1278C;
190) C491T/A492T/C560T/G561T/A611G/T612C/A677T/C678T/T772A/A774T/A 853C/G963T/A971T/A972T/A976T/A977G/T978C/A1216T/T1218G;
191) C491T/A492T/C560T/G561T/A611G/T612C/A677T/C678T/T772A/A774T/A 853C/A971T/A972T/A976T/A977G/T978C/A1166T/A1167C;
192) C491T/A492T/C560T/G561T/A611G/T612C/A677T/C678T/A971T/A972T/A 976T/A977G/T978C/A1166T/A1167C/A1216T/T1218G;
193) C491T/A492T/C560T/G561T/A468T/A971T/A972T/A976T/A977G/T978C;
194) A59T/C60G/T224A/C560T/G561T/A677T/C678T/T772A/A774T/A971T/A972T/A976T/A977G/T978C/A1141C/A1142G/A1143T/A1166T/A1167C/C1366T/C1367T/A1368G;

195) A59T/C60G/T224A/C560T/G561T/A677T/C678T/ T772A/A774T/A853C/A976T/A977G/T978C/C1276T/ T1278C;
196) A59T/C60G/T224A/C560T/G561T/A677T/C678T/ G963T/A971T/A972T/A976T/A977G/T978C;
197) A59T/C60G/T224A/C560T/G561T/A677T/C678T/ A971T/A972T/A976T/A977G/T978C/A1141C/A1142G/ A1143T/A1166T/A1167C/C1366T/C1367T/A1368G;
198) A59T/C60G/T224A/C491T/A492T/C560T/G561T/ A853C/G963T/A976T/A977G/T978C/A1141C/A1142G/ A1143T/C1276T/T1278C;
199) A59T/C60G/T224A/C491T/A492T/C560T/G561T/ A611G/T612C/A976T/A977G/T978;
200) A59T/C60G/T224A/C491T/A492T/C560T/G561T/ A611G/T612C/A853C/G963T/A976T/A977G/T978C/ A1141C/A1142G/A1143T/C1276T/T1278C;
201) A59T/C60G/T224A/A468T/C560T/G561T/G963T/ A971T/A972T/A976T/A977G/T978C/C1276T/T1278C/ C1366T/C1367T/A1368G;
202) A59T/C60G/T224A/A468T/C560T/G561T/A976T/ A977G/T978C/A1166T/A1167C/A1216T/T1218G/ C1276T/T1278C;
203) A59T/C60G/T224A/A468T/C560T/G561T/A976T/ A977G/T978C/A1141C/A1142G/A1143T/C1276T/ T1278C;
204) A59T/C60G/T224A/A468T/C560T/G561T/A677T/ C678T/G963T/A971T/A972T/A976T/A977G/T978C/ C1276T/T1278C/C1366T/C1367T/A1368G;
205) A59T/C60G/T224A/A468T/C560T/G561T/A611G/ T612C/A853C/A976T/A977G/T978C/A1141C/A1142G/ A1143T/A1166T/A1167C;
206) A59T/C60G/T224A/A468T/C491T/A492T/C560T/ G561T/T772A/A774T/G963T/A971T/A972T/A976T/ A977G/T978C/A1141C/A1142G/A1143T/A1216T/ T1218G;
207) A59T/C60G/T224A/A468T/C491T/A492T/C560T/ G561T/A611G/T612C/A853C/A976T/A977G/T978C/ A1141C/A1142G/A1143T/A1166T/A1167C;
208) A59T/C60G/T224A/A267T/C560T/G561T/T772A/ A774T/A853C/G963T/A976T/A977G/T978C/A1166T/ A1167C;
209) A59T/C60G/T224A/A267T/C560T/G561T/A611G/ T612C/G963T/A971T/A972T/A976T/A977G/T978C/ A1141C/A1142G/A1143T;
210) A59T/C60G/T224A/A267T/C491T/A492T/C560T/ G561T/A853C/G963T/A971T/9722T/A976T/A977G/ T978C/A1141C/A1142G/A1143T;
211) A59T/C60G/T224A/A267T/C491T/A492T/C560T/ G561T/A677T/C678T/A853C/G963T/A976T/A977G/ T978C/A1166T/A1167C/A1216T/T1218G;
212) A59T/C60G/T224A/A267T/C491T/A492T/C560T/ G561T/A611G/T612C/T772A/A774T/A853C/A971T/ A972T/A976T/A977G/T978;
213) A59T/C60G/T224A/A267T/A468T/C560T/G561T/ T772A/A774T/A853C/A971T/A972T/A976T/A977G/ T978C;
214) A59T/C60G/T224A/A267T/A468T/C560T/G561T/ A611G/T612C/T772A/A774T/G963T/A976T/A977G/ T978C/A1166T/A1167C/A1216T/T1218G;
215) A59T/C60G/T224A/A267T/A468T/C560T/G561T/ A611G/T612C/A853C/G963T/A976T/A977G/T978C/ A1166T/A1167C;
216) A59T/C60G/T224A/A267T/A468T/C491T/A492T/ C560T/G561T/T772A/A774T/A976T/A977G/T978C/ A1141C/A1142G/A1143T/A1166T/A1167C/A1216T/ T1218G;

217) A59T/C60G/C560T/G561T/T772A/A774T/G963T/ A976T/A977G/T978C/C1276T/T1278C;
218) A59T/C60G/C560T/G561T/T772A/A774T/G963T/ A976T/A977G/T978C/A1141C/A1142G/A1143T/A1166T/ A1167C/C1276T/T1278C;
219) A59T/C60G/C560T/G561T/T772A/A774T/A971T/ A972T/A976T/A977G/T978C/C1276T/T1278C;
220) A59T/C60G/C560T/G561T/T772A/A774T/A971T/ A972T/A976T/A977G/T978C/A1216T/T1218G;
221) A59T/C60G/C560T/G561T/T772A/A774T/A1216T/ T1218G/A976T/A977G/T 978C/C1276T/T1278C;
222) A59T/C60G/C560T/G561T/G963T/A976T/A977G/ T978C/A1216T/T1218G;
223) A59T/C60G/C560T/G561T/G963T/A976T/A977G/ T978C/A1166T/A1167C;
224) A59T/C60G/C560T/G561T/G963T/A971T/A972T/ A976T/A977G/T978C/A1141C/A1142G/A1143T/A1216T/ T1218G/C1276T/T1278C;
225) A59T/C60G/C560T/G561T/A976T/A977G/T978C/ A1166T/A1167C/C1276T/T1278C;
226) A59T/C60G/C560T/G561T/A976T/A977G/T978C/ A1141C/A1142G/A1143T/C1276T/T1278C;
227) A59T/C60G/C560T/G561T/A976T/A977G/T978C/ A1141C/A1142G/A1143T/A1216T/T1218G;
228) A59T/C60G/C560T/G561T/A971T/A972T/A976T/ A977G/T978C/A1216T/T1218G;
229) A59T/C60G/C560T/G561T/A853C/G963T/A971T/ A972T/A976T/A977G/T978C/C1276T/T1278C;
230) A59T/C60G/C560T/G561T/A853C/G963T/A971T/ A972T/A976T/A977G/T978C/A1166T/A1167C;
231) A59T/C60G/C560T/G561T/A853C/A976T/A977G/ T978C/A1166T/A1167C/A 1216T/T1218G/C1276T/ T1278C;
232) A59T/C60G/C560T/G561T/A853C/A976T/A977G/ T978C/A1141C/A1142G/A 1143T;
233) A59T/C60G/C560T/G561T/A677T/C678T/T772A/ A774T/A976T/A977G/T978C/A1216T/T1218G/C1276T/ T1278C;
234) A59T/C60G/C560T/G561T/A677T/C678T/T772A/ A774T/A976T/A977G/T978C/A1216T/T1218G;
235) A59T/C60G/C560T/G561T/A677T/C678T/T772A/ A774T/A976T/A977G/T978C/A1166T/A1167C/A1216T/ T1218G;
236) A59T/C60G/C560T/G561T/A677T/C678T/A976T/ A977G/T978C/A1166T/A1167C;
237) A59T/C60G/C560T/G561T/A677T/C678T/A976T/ A977G/T978C/A1141C/A1142G/A1143T;
238) A59T/C60G/C560T/G561T/A677T/C678T/A853C/ A976T/A977G/T978C/C1276T/T1278C;
239) A59T/C60G/C560T/G561T/A677T/C678T/A853C/ A971T/A972T/A976T/A977G/T978C/A1141C/A1142G/ A1143T/C1276T/T1278C;
240) A59T/C60G/C560T/G561T/A611G/T612C/T772A/ A774T/A976T/A977G/T978C/A1141C/A1142G/A1143T;
241) A59T/C60G/C560T/G561T/A611G/T612C/T772A/ A774T/A853C/G963T/A971T/A972T/A976T/A977G/ T978C/A1166T/A1167C/C1276T/T1278C;
242) A59T/C60G/C560T/G561T/A611G/T612C/A971T/ A972T/A976T/A977G/T978;
243) A59T/C60G/C560T/G561T/A611G/T612C/A677T/ C678T/T772A/A774T/A976T/A977G/T978C/A1216T/ T1218G/C1276T/T1278C;
244) A59T/C60G/C560T/G561T/A611G/T612C/A677T/ C678T/G963T/A976T/A977G/T978C/A1216T/T1218G/ C1276T/T1278C;

245) A59T/C60G/C560T/G561T/A611G/T612C/A677T/C678T/A976T/A977G/T978 C/A1141C/A1142G/A1143T/A1216T/T1218G/C1276T/T1278C;
246) A59T/C60G/C560T/G561T/A611G/T612C/A677T/C678T/A971T/A972T/A976T/A977G/T978C/A1141C/A1142G/A1143T/C1276T/T1278C;
247) A59T/C60G/C560T/G561T/A611G/T612C/A677T/C678T/A853C/A971T/A972T/A976T/A977G/T978C/C1276T/T1278C;
248) A59T/C60G/C491T/A492T/C560T/G561T/T772A/A774T/G963T/A976T/A977G/T978C/A1166T/A1167C;
249) A59T/C60G/C491T/A492T/C560T/G561T/T772A/A774T/A971T/A972T/A976T/A977G/T978C/A1141C/A1142G/A1143T/A1216T/T1218G;
250) A59T/C60G/C491T/A492T/C560T/G561T/T772A/A774T/A971T/A972T/A976T/A977G/T978C;
251) A59T/C60G/C491T/A492T/C560T/G561T/T772A/A774T/A853C/A971T/A972T/A976T/A977G/T978C/A1216T/T1218G;
252) A59T/C60G/C491T/A492T/C560T/G561T/G963T/A976T/A977G/T978C/A1166T/A1167C/C1366T/C1367T/A1368G;
253) A59T/C60G/C491T/A492T/C560T/G561T/G963T/A976T/A977G/T978C/A1141C/A1142G/A1143T/C1276T/T1278C;
254) A59T/C60G/C491T/A492T/C560T/G561T/G963T/A976T/A977G/T978C;
255) A59T/C60G/C491T/A492T/C560T/G561T/A853C/G963T/A976T/A977G/T978C/A1141C/A1142G/A1143T/A1166T/A1167C/A1216T/T1218G;
256) A59T/C60G/C491T/A492T/C560T/G561T/A853C/G963T/A971T/A972T/A976T/A977G/T978C/A1216T/T1218G;
257) A59T/C60G/C491T/A492T/C560T/G561T/A853C/A976T/A977G/T978C;
258) A59T/C60G/C491T/A492T/C560T/G561T/A677T/C678T/T772A/A774T/A976T/A977G/T978C/C1276T/T1278C;
259) A59T/C60G/C491T/A492T/C560T/G561T/A677T/C678T/T772A/A774T/A976T/A977G/T978C/A1166T/A1167C;
260) A59T/C60G/C491T/A492T/C560T/G561T/A677T/C678T/T772A/A774T/A976T/A977G/T978C/A1141C/A1142G/A1143T/A1166T/A1167C;
261) A59T/C60G/C491T/A492T/C560T/G561T/A677T/C678T/T772A/A774T/A853C/A971T/A972T/A976T/A977G/T978C;
262) A59T/C60G/C491T/A492T/C560T/G561T/A677T/C678T/A971T/A972T/A976T/A977G/T978C;
263) A59T/C60G/C491T/A492T/C560T/G561T/A611G/T612C/A853C/A971T/A972T/A976T/A977G/T978C/A1166T/A1167C/C1276T/T1278C;
264) A59T/C60G/C491T/A492T/C560T/G561T/A611G/T612C/A677T/C678T/A976T/A977G/T978C/A1166T/A1167C/A1216T/T1218G;
265) A59T/C60G/A468T/C560T/G561T/T772A/A774T/G963T/A971T/A972T/A976T/A977G/T978C;
266) A59T/C60G/A468T/C560T/G561T/G963T/A976T/A977G/T978C/A1216T/T1218G/C1276T/T1278C;
267) A59T/C60G/A468T/C560T/G561T/G963T/A971T/A972T/A976T/A977G/T978C/A1166T/A1167C/C1276T/T1278C/C1366T/C1367T/A1368G;
268) A59T/C60G/A468T/C560T/G561T/A853C/G963T/A971T/A972T/A976T/A977G/T978C/C1276T/T1278C;
269) A59T/C60G/A468T/C560T/G561T/A853C/G963T/A971T/A972T/A976T/A977G/T978C/A1166T/A1167C;
270) A59T/C60G/A468T/C560T/G561T/A853C/A976T/A977G/T978C;
271) A59T/C60G/A468T/C560T/G561T/A853C/A971T/A972T/A976T/A977G/T978C/A1141C/A1142G/A1143T/A1166T/A1167C;
272) A59T/C60G/A468T/C560T/G561T/A677T/C678T/A976T/A977G/T978C;
273) A59T/C60G/A468T/C560T/G561T/A677T/C678T/A853C/A976T/A977G/T978C/A1141C/A1142G/A1143T;
274) A59T/C60G/A468T/C560T/G561T/A611G/T612C/A976T/A977G/T978C/A1166T/A1167C/A1216T/T1218G/C1276T/T1278C;
275) A59T/C60G/A468T/C560T/G561T/A611G/T612C/A971T/A972T/A976T/A977G/T978C;
276) A59T/C60G/A468T/C560T/G561T/A611G/T612C/A677T/C678T/T772A/A774T/A971T/A972T/A976T/A977G/T978C/A1141C/A1142G/A1143T/C1276T/T1278C;
277) A59T/C60G/A468T/C491T/A492T/C560T/G561T/T772A/A774T/G963T/A976T/A977G/T978C/A1141C/A1142G/A1143T/A1166T/A1167C/A1216T/T1218G/C1276T/T1278C;
278) A59T/C60G/A468T/C491T/A492T/C560T/G561T/T772A/A774T/A976T/A977G/T978C/A1141C/A1142G/A1143T/A1166T/A1167C/A1216T/T1218G/C1276T/T1278C;
279) A59T/C60G/A468T/C491T/A492T/C560T/G561T/G963T/A971T/A972T/A976T/A977G/T978C;
280) A59T/C60G/A468T/C491T/A492T/C560T/G561T/A677T/C678T/T772A/A774T/A853C/A976T/A977G/T978C/A1216T/T1218G/C1276T/T1278C;
281) A59T/C60G/A468T/C491T/A492T/C560T/G561T/A677T/C678T/A853C/G963T/A971T/A972T/A976T/A977G/T978C/A1216T/T1218G/C1276T/T1278C;
282) A59T/C60G/A468T/C491T/A492T/C560T/G561T/A611G/T612C/A677T/C678T/G963T/A971T/A972T/A976T/A977G/T978C/A1166T/A1167C/C1276T/T1278C;
283) A59T/C60G/A267T/C560T/G561T/T772A/A774T/G963T/A971T/A972T/A976T/A977G/T978C/A1166T/A1167C;
284) A59T/C60G/A267T/C560T/G561T/T772A/A774T/A976T/A977G/T978C;
285) A59T/C60G/A267T/C560T/G561T/A611G/T612C/T772A/A774T/A853C/A976T/A977G/T978C/A1166T/A1167C;
286) A59T/C60G/A267T/C560T/G561T/A611G/T612C/A853C/G963T/A976T/A977G/T978C/A1141C/A1142G/A1143T/C1276T/T1278C;
287) A59T/C60G/A267T/C560T/G561T/A611G/T612C/A853C/A976T/A977G/T978C/C1276T/T1278C;
288) A59T/C60G/A267T/C491T/A492T/C560T/G561T/A853C/A976T/A977G/T978C/A1141C/A1142G/A1143T;
289) A59T/C60G/A267T/C491T/A492T/C560T/G561T/A677T/C678T/T772A/A774T/G963T/T/A1T/A972T/A976T/A977G/T978C/A1141C/A1142G/A1143T/C1366T/C1367T/A1368G;
290) A59T/C60G/A267T/C491T/A492T/C560T/G561T/A677T/C678T/A976T/A977G/T978C/A1166T/A1167C/A1216T/T1218G;
291) A59T/C60G/A267T/C491T/A492T/C560T/G561T/A677T/C678T/A853C/G963T/A976T/A977G/T978C/A1141C/A1142G/A1143T/C1366T/C1367T/A1368G;
292) A59T/C60G/A267T/C491T/A492T/C560T/G561T/A611G/T612C/A677T/C678 T/A971T/A972T/A976T/A977G/T978C;

293) A59T/C60G/A267T/C491T/A492T/C560T/G561T/A611G/T612C/A677T/C678T/A853C/A976T/A977G/T978C/A1141C/A1142G/A1143T/A1166T/A1167C/A1216T/T1218G;
294) A59T/C60G/A267T/A468T/C560T/G561T/T772A/A774T/G963T/A976T/A977G/T978C/A1141C/A1142G/A1143T/C1366T/C1367T/A1368G;
295) A59T/C60G/A267T/A468T/C560T/G561T/A971T/A972T/A976T/A977G/T978C/A1141C/A1142G/A1143T/C1276T/T1278C;
296) A59T/C60G/A267T/A468T/C560T/G561T/A853C/A976T/A977G/T978C/A1141C/A1142G/A1143T/A1166T/A1167C;
297) A59T/C60G/A267T/A468T/C560T/G561T/A853C/A971T/A972T/A976T/A977G/T978C/A1166T/A1167C;
298) A59T/C60G/A267T/A468T/C560T/G561T/A677T/C678T/G963T/A976T/A977G/T978C/A1141C/A1142G/A1143T/A1216T/T1218G;
299) A59T/C60G/A267T/A468T/C560T/G561T/A677T/C678T/A976T/A977G/T978C/A1141C/A1142G/A1143T/A1166T/A1167C;
300) A59T/C60G/A267T/A468T/C560T/G561T/A611G/T612C/A853C/A971T/A972T/A976T/A977G/T978C/A1141C/A1142G/A1143T/A1166T/A1167C;
301) A59T/C60G/A267T/A468T/C560T/G561T/A611G/T612C/A677T/C678T/A853C/A971T/T/A972T/A976T/A977G/T978C/A1141C/A1142G/A1143T/A1166T/A1167C;
302) A59T/C60G/A267T/A468T/C491T/A492T/C560T/G561T/T772A/A774T/A853C/A976T/A977G/T978C/A1141C/A1142G/A1143T/C1276T/T1278C;
303) A59T/C60G/A267T/A468T/C491T/A492T/C560T/G561T/A677T/C678T/G963T/A976T/A977G/T978C/A1166T/A1167C/A1216T/T1218G/C1276T/T1278C;
304) A59T/C60G/A267T/A468T/C491T/A492T/C560T/G561T/A611G/T612C/T772A/A774T/A853C/A976T/A977G/T978C/A1141C/A1142G/A1143T/C1276T/T1278C;
305) A59T/C60G/A267T/A468T/C491T/A492T/C560T/G561T/A611G/T612C/A853C/A971T/A972T/A976T/A977G/T978C/A1141C/A1142G/A1143T/C1276T/T1278C;
306) A468T/C560T/G561T/T772A/A774T/G963T/A976T/A977G/T978C;
307) A468T/C560T/G561T/T772A/A774T/A853C/G963T/A971T/A972T/A976T/A 977G/T978C/A1141C/A1142G/A1143T/A1216T/T1218G/C1276T/T1278C;
308) A468T/C560T/G561T/G963T/A976T/A977G/T978C/A1216T/T1218G;
309) A468T/C560T/G561T/G963T/A976T/A977G/T978C/A1166T/A1167C/C1276T/T1278C;
310) A468T/C560T/G561T/A853C/A976T/A977G/T978C/C1276T/T1278C;
311) A468T/C560T/G561T/A853C/A976T/A977G/T978C/A1166T/A1167C;
312) A468T/C560T/G561T/A677T/C678T/T772A/A774T/A976T/A977G/T978C/A 1216T/T1218G;
313) A468T/C560T/G561T/A677T/C678T/T772A/A774T/A853C/G963T/A976T/A 977G/T978C/A1141C/A1142G/A1143T/A1166T/A1167C/A1216T/T1218G;
314) A468T/C560T/G561T/A677T/C678T/A976T/A977G/T978C/A1141C/A1142G/A1143T;
315) A468T/C560T/G561T/A611G/T612C/T772A/A774T/A853C/G963T/A976T/A 977G/T978C/A1141C/A1142G/A1143T/A1166T/A1167C;
316) A468T/C560T/G561T/A611G/T612C/G963T/A976T/A977G/T978C/A1166T/A1167C/C1276T/T1278C;
317) A468T/C560T/G561T/A611G/T612C/G963T/A971T/A972T/A976T/A977G/T 978C;
318) A468T/C560T/G561T/A611G/T612C/A976T/A977G/T978C/C1276T/T1278C;
319) A468T/C560T/G561T/A611G/T612C/A976T/A977G/T978C/A1141C/A1142G/A1143T/C1276T/T1278C;
320) A468T/C560T/G561T/A611G/T612C/A976T/A977G/T978C/A1141C/A1142G/A1143T;
321) A468T/C560T/G561T/A611G/T612C/A971T/A972T/A976T/A977G/T978C/A 1166T/A1167C/A1216T/T1218G;
322) A468T/C560T/G561T/A611G/T612C/A971T/A972T/A976T/A977G/T978C/A 1141C/A1142G/A1143T/C1276T/T1278C;
323) A468T/C560T/G561T/A611G/T612C/A677T/C678T/A853C/G963T/A976T/A 977G/T978C/A1216T/T1218G/C1276T/T1278C/C1366T/C1367T/A1368G;
324) A468T/C560T/G561T/A611G/T612C/A677T/C678T/A853C/A971T/A972T/A 976T/A977G/T978C/A1166T/A1167C/C1276T/T1278C/C1366T/C1367T/A1368G;
325) A468T/C560T/G561T/A611G/T612C/A1166T/A1167C/A976T/A977G/T978C/C1276T/T1278C;
326) A468T/C491T/A492T/C560T/G561T/T772A/A774T/A976T/A977G/T978C/A 1216T/T1218G/C1276T/T1278C;
327) A468T/C491T/A492T/C560T/G561T/T772A/A774T/A971T/A972T/A976T/A 977G/T978C/A1166T/A1167C;
328) A468T/C491T/A492T/C560T/G561T/T772A/A774T/A971T/A972T/A976T/A 977G/T978C;
329) A468T/C491T/A492T/C560T/G561T/A976T/A977G/T978C/A1166T/A1167C;
330) A468T/C491T/A492T/C560T/G561T/A971T/A972T/A976T/A977G/T978C/C1276T/T1278C;
331) A468T/C491T/A492T/C560T/G561T/A971T/A972T/A976T/A977G/T978C/A 1141C/A1142G/A1143T/A1216T/T1218G/C1276T/T1278C;
332) A468T/C491T/A492T/C560T/G561T/A971T/A972T/A976T/A977G/T978C/A 1141C/A1142G/A1143T;
333) A468T/C491T/A492T/C560T/G561T/A677T/C678T/A976T/A977G/T978C/C1276T/T1278C;
334) A468T/C491T/A492T/C560T/G561T/A611G/T612C/A976T/A977G/T978C/A 1141C/A1142G/A1143T/C1276T/T1278C;
335) A468T/C491T/A492T/C560T/G561T/A611G/T612C/A677T/C678T/T772A/A 774T/G963T/A971T/A972T/A976T/A977G/T978C;
336) A267T/C560T/G561T/T772A/A774T/A976T/A977G/T978C/C1276T/T1278C;
337) A267T/C560T/G561T/T772A/A774T/A976T/A977G/T978C/C1366T/C1367T/A1368G;
338) A267T/C560T/G561T/T772A/A774T/A853C/A976T/A977G/T978C/A1166T/A1167C/A1216T/T1218G;
339) A267T/C560T/G561T/T772A/A774T/A853C/A971T/A972T/A976T/A977G/T 978C/A1216T/T1218G;
340) A267T/C560T/G561T/A976T/A977G/T978C/C1276T/T1278C/C1366T/C1367T/A1368G;
341) A267T/C560T/G561T/A971T/A972T/A976T/A977G/T978C/A1166T/A1167C;
342) A267T/C560T/G561T/A853C/A976T/A977G/T978C/C1276T/T1278C;
343) A267T/C560T/G561T/A853C/A976T/A977G/T978C/A1141C/A1142G/A1143T;
344) A267T/C560T/G561T/A677T/C678T/T772A/A774T/G963T/A976T/A977G/T 978C/A1141C/A1142G/A1143T/A1166T/A1167C/C1366T/C1367T/A1368G;
345) A267T/C560T/G561T/A677T/C678T/G963T/A976T/A977G/T978C;
346) A267T/C560T/G561T/A677T/C678T/A853C/G963T/A971T/A972T/A976T/A 977G/T978C/A1166T/A1167C;

347) A267T/C560T/G561T/A677T/C678T/A853C/G963T/A971T/A972T/A976T/A 977G/T978C;
348) A267T/C560T/G561T/A611G/T612C/T772A/A774T/G963T/A971T/A972T/A 976T/A977G/T978C/A1141C/A1142G/A1143T/C1276T/T1278C;
349) A267T/C560T/G561T/A611G/T612C/A976T/A977G/T978C/C1366T/C1367T/A1368G;
350) A267T/C560T/G561T/A611G/T612C/A976T/A977G/T978C/A1216T/T1218G;
351) A267T/C560T/G561T/A611G/T612C/A971T/A972T/A976T/A977G/T978C/A 1166T/A1167C/A1216T/T1218G/C1276T/T1278C;
352) A267T/C560T/G561T/A611G/T612C/A677T/C678T/A976T/A977G/T978C/A 1166T/A1167C/A1216T/T1218G/C1276T/T1278C;
353) A267T/C560T/G561T/A611G/T612C/A677T/C678T/A976T/A977G/T978C/A 1166T/A1167C;
354) A267T/C491T/A492T/C560T/G561T/G963T/A976T/A977G/T978C/A1216T/T1218G;
355) A267T/C491T/A492T/C560T/G561T/A971T/A972T/A976T/A977G/T978C/A 1166T/A1167C;
356) A267T/C491T/A492T/C560T/G561T/A853C/G963T/A976T/A977G/T978C/A 1141C/A1142G/A1143T/A1166T/A1167C;
357) A267T/C491T/A492T/C560T/G561T/A853C/G963T/A971T/A972T/A976T/A 977G/T978C/A1141C/A1142G/A1143T/A1166T/A1167C/A1216T/T1218G/C1366T/C1367T/A1368G;
358) A267T/C491T/A492T/C560T/G561T/A853C/A976T/A977G/T978C;
359) A267T/C491T/A492T/C560T/G561T/A611G/T612C/T772A/A774T/G963T/A 971T/A972T/A976T/A977G/T978C/A1166T/A1167C/A1216T/T1218G/C1276T/T1278C;
360) A267T/C491T/A492T/C560T/G561T/A611G/T612C/T772A/A774T/A976T/A 977G/T978C/A1141C/A1142G/A1143T;
361) A267T/C491T/A492T/C560T/G561T/A611G/T612C/T772A/A774T/A976T/A 977G/T978C;
362) A267T/C491T/A492T/C560T/G561T/A611G/T612C/G963T/A971T/A972T/A 976T/A977G/T978C/A1141C/A1142G/A1143T/A1216T/T1218G/C1276T/T1278C;
363) A267T/C491T/A492T/C560T/G561T/A611G/T612C/A677T/C678T/T772A/A 774T/G963T/A976T/A977G/T978C/C1276T/T1278C;
364) A267T/C491T/A492T/C560T/G561T/A611G/T612C/A677T/C678T/A971T/A 972T/A976T/A977G/T978C/A1141C/A1142G/A1143T/C1276T/T1278C;
365) A267T/A468T/C560T/G561T/T772A/A774T/G963T/A971T/A972T/A976T/A 977G/T978C;
366) A267T/A468T/C560T/G561T/A976T/A977G/T978C/A1141C/A1142G/A1143T;
367) A267T/A468T/C560T/G561T/A677T/C678T/T772A/A774T/A853C/A976T/A 977G/T978C/A1166T/A1167C/A1216T/T1218G/C1276T/T1278C;
368) A267T/A468T/C560T/G561T/A677T/C678T/A971T/A972T/A976T/A977G/T 978C/A1166T/A1167C/A1216T/T1218G/C1276T/T1278C;
369) A267T/A468T/C560T/G561T/A611G/T612C/A976T/A977G/T978C/A1141C/A1142G/A1143T/A1216T/T1218G/C1276T/T1278C/C1366T/C1367T/A1368G;
370) A267T/A468T/C560T/G561T/A611G/T612C/A853C/G963T/A976T/A977G/T 978C/C1276T/T1278C/C1366T/C1367T/A1368G;
371) A267T/A468T/C560T/G561T/A611G/T612C/A853C/G963T/A976T/A977G/T 978C/A1166T/A1167C/A1216T/T1218G;
372) A267T/A468T/C560T/G561T/A611G/T612C/A677T/C678T/T772A/A774T/A 976T/A977G/T978C/A1166T/A1167C/A1216T/T1218G/C1276T/T1278C;
373) A267T/A468T/C560T/G561T/A611G/T612C/A677T/C678T/T772A/A774T/A 853C/G963T/A971T/A972T/A976T/A977G/T978C;
374) A267T/A468T/C560T/G561T/A611G/T612C/A677T/C678T/G963T/A971T/A 972T/A976T/A977G/T978C/A1141C/A1142G/A1143T/A1216T/T1218G;
375) A267T/A468T/C560T/G561T/A611G/T612C/A677T/C678T/A853C/G963T/A 976T/A977G/T978C/A1166T/A1167C/C1276T/T1278C;
376) A267T/A468T/C491T/A492T/C560T/G561T/T772A/A774T/A976T/A977G/T 978C/A1166T/A1167C/A1216T/T1218G/C1276T/T1278C;
377) A267T/A468T/C491T/A492T/C560T/G561T/T772A/A774T/A976T/A977G/T 978C/A1166T/A1167C;
378) A267T/A468T/C491T/A492T/C560T/G561T/A853C/A976T/A977G/T978C/A 1166T/A1167C/A1216T/T1218G/C1276T/T1278C;
379) A267T/A468T/C491T/A492T/C560T/G561T/A677T/C678T/T772A/A774T/G 963T/A971T/A972T/A976T/A977G/T978C;
380) A267T/A468T/C491T/A492T/C560T/G561T/A611G/T612C/A853C/G963T/A 976T/A977G/T978C/A1166T/A1167C/A1216T/T1218G;
381) A267T/A468T/C491T/A492T/C560T/G561T/A611G/T612C/A853C/A971T/A 972T/A976T/A977G/T978C/A1141C/A1142G/A1143T;
382) A267T/A468T/C491T/A492T/C560T/G561T/A611G/T612C/A677T/C678T/T772A/A774T/A853C/A976T/A977G/T978C/A1166T/A1167C/C1276T/T1278C;
383) A267T/A468T/C491T/A492T/C560T/G561T/A611G/T612C/A677T/C678T/T772A/A774T/A853C/A976T/A977G/T978C/A1166T/A1167C;
384) A267T/A468T/C491T/A492T/C560T/G561T/A611G/T612C/A677T/C678T/A 971T/A972T/A976T/A977G/T978C/C1366T/C1367T/A1368G;
385) A267T/A468T/C491T/A492T/C560T/G561T/A611G/T612C/A677T/C678T/A 853C/A971T/A972T/A976T/A977G/T978C/A1141C/A1142G/A1143T.

The nucleic acid molecule may be obtained based on genes encoding the wild type aspartase shown in sequence 1 according to technical means including but not limited to the following: for example, sequence saturation mutagenesis, site directed mutagenesis, directed evolution, and many other methods of recombination.

Sequence saturation mutagenesis refers to mutagenesis of all forms or all possible forms of bases in a small region of a gene encoding a parent enzyme. Site directed mutagenesis may be achieved by methods known in the art, see, for example, Patent Grant Publication No. CN 1860227 B to German Bremen.

Site directed mutagenesis refers to a technique that introduces one or more, such as several mutations at one or more, such as several positions of the parent polynucleotide. Site directed mutagenesis may be achieved by methods known in the art, see, for example, Patent Grant Publication No. CN 101139586 B to Hubei University. Any procedure for site directed mutagenesis may also be used in the present invention, and there are many commercially available kits that may be used to prepare variants.

Directed evolution refers to random mutagenesis of the gene encoding the parent aspartase by error-prone PCR, chemical mutagenesis. Mutant genes then may be recombined in vitro by SOE PCR, restriction digestion, and DNA shuffling. The target mutant may be selected by the designed high-throughput screening method.

A recombinant vector, an expression cassette or a recombinant cell including the nucleic acid molecule mentioned above also falls into the protection scope of the present invention.

The recombinant vector may be a recombinant cloning vector or a recombinant expression vector.

The expression vector typically includes regulatory sequences encoding a promoter, an operon, a ribosome binding site, a translation initiation signal, and optionally a repressor gene or multiple activator genes. Different nucleic acid sequences and regulatory sequences may be ligated together to produce a recombinant expression vector, which may include one or more convenient restriction sites such that polynucleotides may be inserted at these sites or substitute for polynucleotides encoding the variant.

The recombinant expression vector carrying the DNA sequence encoding the aspartase variant of the present invention may be any vector that can facilitate the recombinant DNA process and allow expression of the polynucleotide. The choice of a recombinant expression vector usually depends on the compatibility of the vector with the host cell into which it is to be introduced. The vector may be a linear or closed circular plasmid.

The vector may be an autonomously replicating vector, that is, a vector that exists as an extrachromosomal entity whose replication is independent of chromosomal replication, such as a plasmid, extrachromosomal element, minichromosome, or artificial chromosome. The vector may contain any element to ensure self-replication. Alternatively, the vector may be a vector, when introduced into a host cell, is integrated into the genome and replicated with one or more chromosomes into which it has been integrated.

The vector preferably includes one or more selectable markers that allow convenient selection of cells such as transformed cells, transfected cells, transduced cells, and the like. A selectable marker is a gene whose product provides biocide resistance, or virus resistance, or heavy metal resistance, or auxotrophic prototrophy.

Examples of bacterial selectable markers are dal genes of *Bacillus licheniformis* or *Bacillus subtilis*, or marks imparting resistance to antibiotics such as, ampicillin, chloramphenicol, kanamycin, neomycin, spectinomycin, or tetracycline. Suitable markers for use in yeast host cells include, but are not limited to, ADE2, HIS3, LEU2, LYS2, MET3, TRP1, and URA3. Selectable markers for use in filamentous fungal host cells include, but are not limited to, amdS (acetamidase), argB (ornithine carbamyltransferase), bar (glufosinate acetyltransferase), hph (hygromycin phosphotransferase), niaD (nitrate reductase), pyrG (orotinoside-5' phosphate decarboxylase), sC (adenosyl sulfate transferase), and trpC (anthranilate synthase), as well as their equivalents.

The vector preferably contains one or more elements that allow the vector to integrate into the host cell's genome or that allow the vector autonomously replicates in the cell independently of the genome.

As for integration into the host cell genome, the vector may rely on a polynucleotide sequence encoding the vector or any other element of the vector for integration into the genome by homologous or non-homologous recombination. Alternatively, the vector may contain additional polynucleotides for directing integration into the host cell genome at one or more precise positions in one or more chromosomes by homologous recombination. To increase the likelihood of integration at precise locations, these integrated elements should contain a sufficient number of nucleic acids, such as 100 to 10,000 base pairs, 400 to 10,000 base pairs, and 800 to 10,000 base pairs. A high degree of sequence identity between these base pairs to the corresponding target sequence may increase the possibility of homologous recombination. These integration elements may be any sequence that is homologous to a target sequence within the genome of the host cell. In addition, these integration elements may be non-coding polynucleotides or coding polynucleotides. On the other hand, the vector may be integrated into the genome of the host cell by non-homologous recombination.

As for autonomous replication, the vector may further include an origin of replication capable of autonomously replicating in the corresponding host cell using the vector. The origin of replication can be any plasmid replicon that functions in a cell to mediate autonomous replication. The term "origin of replication" or "plasmid replicator" means a polynucleotide that allows a plasmid or vector to replicate in vivo.

Examples of origins of replication for bacterial host cells are origins of replication of plasmids pBR322, pUC19, pACYC177, and pACYC184 that allow replication in *E. coli*, and origins of replication of plasmids pUB 110, pE194, pTA1060, and pAMβ1 that allow replication in *Bacillus*.

Examples of origins of replication in yeast host cells are the combination of the 2 micron origin of replication ARS1, ARS4, ARS1 and CEN3, and the combination of ARS4 and CEN6.

Examples of origins of replication for filamentous fungal host cells are AMA1 and ANS1.

The steps for ligating the elements described above to construct the recombinant expression vector of the invention are well known to those of ordinary skill in the art.

In the present invention, the recombinant expression vector is specifically a recombinant vector obtained by cloning the gene into a pET21a vector.

The expression cassette contains a promoter that starts transcription of the gene, the gene and a transcription termination sequence. Of course, it may also include, but not limited to a leader sequence, a polyadenylation sequence, a front sequence, and a signal peptide sequence. Regulatory sequences may be provided with a linker for the purpose of introducing a specific restriction site that facilitates ligation of the expression cassette.

The recombinant cell is obtained after the gene is introduced into a host cell.

The term "host cell" herein includes various types of cells that are susceptible to transformation, transfection, transduction, and the like, for introducing the gene. The term "host cell" encompasses any descendant of a parent cell that is not identical to the parent cell due to mutations that occur during replication. The choice of a host cell will depend to a large extent on the gene encoding the protein and its source.

The host cell may be any cell that is useful, such as a prokaryotic cell or a eukaryotic cell.

The prokaryotic host cell can be any gram positive or gram negative bacterial cell. Gram positive bacteria include, but are not limited to *bacillus, clostridium, enterococcus, solibacillus, lactobacillus*, milk coccus, marine *bacillus, staphylococcus, streptococcus*, and *streptomyces*. Gram negative bacteria include, but are not limited to *E. coli, campylobacter, flavobacterium, fusobacterium, helicobacter, ilyobacter, neisseria, pseudomonas, salmonella*, and *ureaplasma*.

The *bacillus* cells include, but are not limited to, *Bacillus alkalophilus, Bacillus amyloliquefaciens, Bacillus brevis,*

*Bacillus sphaericus, Bacillus circulans, Bacillus clausii, Bacillus coagulans, Bacillus firmus, paenibacillus, Bacillus lentus, Bacillus licheniformis, Bacillus megaterium, Bacillus pumilus, Bacillus stearothermophilus, Bacillus subtilis,* and *Bacillus thuringiensis.*

The *streptococcus* cells include, but are not limited to, *Streptococcus equisimilis, Streptococcus pyogenes,* and *Streptococcus equi* subsp. *zooepidemicus* cells.

The *streptomyces* cells include, but are not limited to, *Streptomyces chromogenes, Streptomyces avermitilis, Streptomyces coelicolor, Streptomyces griseus,* and *Streptomyces lividans* cells.

Introduction of the vector into a bacterial host cell can be achieved by the following: protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988 Biotechniques 6: 742-751) or ligation (see, e.g., Koehler and Thorne, 1987, Journal of Bacteriology 169: 5771-5278). However, any method known in the art for introducing DNA into a host cell may be used.

Eukaryotic host cells may be mammalian, insect, plant or fungal cells.

The eukaryotic host cell may be a fungal cell. "Fungi" as used herein includes Ascomycota, Basidiomycota, Chytridiomycota, and Zygomycota (e.g., as defined by Hawksworth et al., in Ainsworth and Bisby's Dictionary of The Fungi, Eighth edition, 1995, CAB International, University Press, Cambridge, UK), and Oomycota and all mitosporic fungi.

The fungal host cell may be a yeast cell. "Yeast" as used herein includes ascosporogenous yeast (Endomycetales), basidiosporogenous yeast, and yeast belonging to Fungi Imperfecti (Blastomycetes). Since the classification of yeast may change in the future, for the purposes of the present invention, yeast should be defined according to, for example, Biology and Activities of Yeast (Skinner, F A, Passmore, S M and Davenport, Ed. RR, Soc.App. Bacteriol. Symposium Series No. 9, 1980).

The yeast host cell may be *Candida, Hansenula, Kluyveromyces, Pichia, Saccharomyces, Schizosaccharomyces,* or *Yarrowia* cells.

The preferred yeast host cells are *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis* cells, or *Yarrowia lipolytica*cells.

The fungal host cell may be a filamentous fungal cell. "Filamentous fungi" includes all filamentous forms of the subfamily Eumycota and Oomycota. Filamentous fungi are typically characterized by a mycelial wall composed of chitin, cellulose, dextran, chitosan, mannan, and other complex polysaccharides. Vegetative growth occurs through hyphae extension, and carbon catabolism is obligately aerobic. In contrast, the vegetative growth of yeasts such as *Saccharomyces cerevisiae* is performed by budding of singlecellbacterial, and carbon catabolism may be fermented.

The filamentous fungal host cell is *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cells.

The preferred filamentous fungal host cells are *Aspergillus awamori, Aspergillus fumigatus, Aspergillus foetidus, Aspergillus japonicus, Aspergillus niger* or *Aspergillus oryzae* cells. In another most preferred aspect, the filamentous fungal host cell is *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium sulphureum, Fusarium torulosum, Fusarium trichothecioides,* or *Fusarium venenatum* cells. In another most preferred aspect, the filamentous fungal host cell is *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei* or *Trichoderma viride* strain cells.

Fungal cells can be transformed in a manner known per se by methods involving protoplast formation, protoplast transformation, and cell wall reconstruction. As for methods for transforming *Aspergillus* and *Trichoderma* host cells, reference may be made to the introduction disclosed in EP 238023 and Yelton et al., 1984, Proc. Nat. Acad. Sci. USA 81: 1200-1204. As for methods for transforming *Fusarium* species, reference may be made to the contents described in Malardier et al., 1989, Gene 78: 120-156 and WO 96/00787. As for methods for transforming yeast host cells, the following references may be referred: Becker and Guarente, edited by Abelson, J N and Simon M I, Guide to Yeast Genetics and Molecular Biology, Methods in Enzymology, Vol. 194, pp. 182-187, Academic Press, Inc., New York; Ito et al., 1983, Journal of Bacteriology 153: 163; and Hinnen et al., 1978, Proc. Nat. Acad. Sci. USA 75: 1920.

In the present invention, the recombinant cell is specifically *E. coli* containing the gene. The *E. coli* is specifically *E. coli* BL21.

The invention also protects the method for producing the aspartase variant, comprising the steps of culturing a host cell containing the nucleic acid molecule, and recovering the aspartase variant from a cell culture.

In the method for producing an aspartase variant of the present invention, the host cell may be cultured in a nutrient medium suitable for producing the variant using methods well known in the art. For example, the host cells may be cultured by shake flask culture in a suitable medium and under conditions that allow the expression and/or isolation of the aspartase variant, and small-scale or large-scale fermentation in a laboratory or industrial fermentor (including continuous, batch, fedbatch, or solid state fermentation). The culture is carried out using methods known in the art in a suitable nutrient medium comprising a carbon source, a nitrogen source, and an inorganic salt. Suitable media may be obtained from commercial suppliers or can be prepared according to published compositions (for example, in the catalog of the American Type Culture Collection). If the aspartase variant is secreted by the host cell into a nutrient medium, the variant may be recovered directly from the medium. If the aspartase variant cannot be secreted into the nutrient medium by the host cell, the variant may be recovered from the cell lysate.

The variants may be detected using methods known in the art that are specific to these variants. These detection methods include, but are not limited to, the use of specific antibodies, the formation of enzymatic products, or the disappearance of enzymatic substrates. For example, an enzyme assay may be used to determine the activity of the variant.

The aspartase variant may be recovered using methods known in the art. For example, the variant may be recovered from the nutrient medium by conventional methods including, but not limited to, centrifugation, filtration, extraction, spray drying, evaporation, or precipitation.

The aspartase variant may be purified by a variety of methods known in the art, including, but not limited to, chromatography (e.g., ion chromatography exchange, affinity chromatography, hydrophobic interaction chromatography, chromatographic focusing, and size exclusion chromatography), electrophoresis (e.g., preparative isoelectric focusing), differential solubility (e.g., ammonium sulfate precipitation), SDS-PAGE or extraction (see, e.g., Protein Purification, Edited by J. C. Janson and Lars Ryden, VCH Publishers, New York, 1989).

Use of the aspartase variant or the nucleic acid molecule or the recombinant vector or the expression cassette or the recombinant cell in the preparation of a product having the activity of catalyzing the ammoniation of acrylic acid also belongs to the protection scope of the present invention.

Use of the aspartase variant or the nucleic acid molecule or the recombinant vector or the expression cassette or the recombinant cell in the production of a target product also belongs to the protection scope of the present invention, wherein the target product is selected from any one or more of β-alanine, β-alanine salt, multimer of β-alanine.

The invention also provides a method for producing a target product, comprising the steps of using acrylic acid or an acrylate and an ammonia-containing material to perform a reaction under the catalysis of the aspartase variant to obtain the target product; the target product is selected from any one or more of β-alanine, β-alanine salt, multimer of β-alanine.

In one embodiment of the present invention, the ammonia-containing material is specifically ammonia water. In the reaction system, the acrylic acid or acrylate is 20-400 mM (specifically, 400 mM), the pH value is 7.0-10.5 (such as 7.0-9.5, further such as 7.5, 8.0-8.5, 9.0), and the reaction temperature is 30-55° C. (such as 35° C., 37° C., 40-45° C., 50° C.), and the reaction time is 0.5-5h (such as 1h, 2h, 3h, and 4h).

BEST MODE OF IMPLEMENTING THE INVENTION

The following examples are provided for better understanding of the present invention, but the present invention is not limited thereto. Unless otherwise specified, the experimental methods in the following examples are conventional methods. Unless otherwise specified, the test materials used in the following examples were purchased from conventional biochemical reagent stores. The quantitative experiments in the following examples all carried out three times, and the results were averaged.

Example 1. Preparation and Identification of Aspartase Variants

This example involves a total of 300 aspartase variants, all of which are derived from a wild type aspartase protein mature body (corresponding encoding gene is shown in sequence 1 in sequence listing) by mutations. The mutation sites of the 300 aspartase variants at the protein and gene levels are specifically shown in Table 1.

I. Cloning

A method known in the art is used to construct a plasmid containing the gene encoding the aspartase and its variant, and the resulting recombinant plasmid is transformed into a suitable host cell.

In this example, the vector plasmid used is specifically pET21a. The gene fragment containing gene encoding the aspartase and variant thereof are used as templates, TATGGCTAGCATGACTGGTatgaataccgatgttcgtattg and GCTAGTTATTGCTCAGCGGttttctctccagcaattcccg as primers to amplify the corresponding nucleotide gene fragments by PCR. Then, the gene fragment obtained by PCR amplification and pET21a are mixed at a molar ratio of 1:1, and the method of Gibson assembly is used (see, Ji Zhicheng et al., Using the Gibson Assembly method to construct a plant expression vector, Journal of south China agricultural university, 2014, 35(5): 112-116) to construct a plasmid containing a gene encoding aspartase or a variant thereof. *E. coli* BL21 (DE3) is used as a host cell, and a recombinant plasmid containing the gene encoding aspartase was introduced into the host cell.

II. Expression

Host cells containing the recombinant plasmid constructed in step I were cultured using a self-inducing medium. The composition of the self-induction medium is as follows: 10 g/L peptone, 5 g/L yeast powder, 3.55 g/L disodium hydrogen phosphate, 3.4 g/L potassium dihydrogen phosphate, 2.68 g/L ammonium chloride, 0.71 g/L sodium sulfate, 0.493 g/L magnesium sulfate heptahydrate, 0.27 g/L ferric chloride hexahydrate, 20 mL/L 100% glycerol, 0.5 g/L glucose, 2 g/L lactose, 50 mg/L ampicillin sodium. Host cells containing the recombinant plasmid are inoculated into a self-inducing medium, and fermentation is performed in a batch fermentation manner. Incubate with shaking at 30° C. and 200 rpm for 20 hours.

III. Cell Collection

The following three methods may be used: ① Centrifugation: centrifuging the cell culture solution at 4000 g for 10 minutes to collect cells; ② Hollow fiber membrane filtration: filtering the cell culture solution with a 0.22 micron hollow fiber membrane to collect cells; ③ Ceramic membrane filtration: collecting cells by filtering through a 50 KDa ceramic membrane. Under laboratory conditions, cells are preferably collected by centrifugation (this method is used in this example), and the enzyme activity is compared.

IV. Purification of Expressed Proteins

Resuspend the cells with ultrapure water to an $OD_{550}$ value of 200. Cells were disrupted by ultrasonication. The conditions of ultrasonication were as follows: working for 1 second, intermittent for two seconds, 180 W, total disruption for 20-25 minutes. Cells may also be lysed using a high pressure homogeneous fragmentation method. The conditions for high pressure homogeneous fragmentation were as follows: 50 HZ, 800 bar, and fragmentation for 2 times.

First, high-speed centrifugation was used to remove cell debris and macromolecular impurities. The centrifugation conditions were as follows: taking 10-50 mL of cell disruption solution, centrifuging for 20-40 minutes at 12000 rpm, 4° C. Then, ultracentrifugation was used to concentrate the supernatant from which cell debris and macromolecular impurities have been removed. The selected ultrafiltration centrifuge tube was Amicon Ultra-15 (or 50) mL ultracentrifugal ultracentrifuge equipped with Ultracel-50 ultrafiltration membrane filter tube. The centrifugation conditions were as follows: centrifuging for 20-40 minutes at 12000 rpm, 4° C. 1-5 mL of pure water was added at 4° C. into the ultrafiltration tube, so as to resuspend the aspartase protein retained by the ultrafiltration tube.

V. Determination of Enzyme Protein Concentration

After the enzyme protein suspension was diluted 100-500 times, its concentration was measured by Bradford method.

VI. Determination of Catalytic Activity for the Ammoniation of Acrylic Acid

Preparation of substrates affected by aspartase variants: acrylic acid or acrylate 20-400 mM, adjust the pH to 7.0-9.5 with ammonia.

The operation steps for the determination of aspartase variants enzyme activity are as follows: take a certain amount of fermented cells or purified enzyme protein, add a substrate, and react at a certain temperature for 0.5-5 h.

β-alanine was detected by high performance liquid chromatography, and the amount of β-alanine before and after the reaction was determined by external standard method. The conditions for liquid chromatography detection are as follows: chromatographic column of Eclipse XDB-C18; mobile phase, potassium dihydrogen phosphate (pH 2.6): acetonitrile=95:5 (volume ratio); flow rate 1.0 mL/min; and detection wavelength of 210 nm.

Preparation of potassium dihydrogen phosphate ($KH_2PO_4$) with pH of 2.6: take 1.44 g of $KH_2PO_4$ and dissolve it in 1 L of ultrapure water, and adjust the pH to 2.6 with 0.6-0.7 mL of 85% phosphoric acid.

Definition of the activity of enzymes for catalyzing the ammoniation of acrylic acid: the production of 1 mM of β-alanine within 1 minute is defined as 1 U. Definition of the activity of enzymes for catalyzing the ammoniation of acrylic acid by unit cell: the production of 1 mM of β-alanine within 1 minute at the concentration of 1.0 $OD_{550}$ cell is defined as 1 $U/OD_{550}$. Definition of the activity of enzymes for catalyzing the ammoniation of acrylic acid by unit protein: the production of 1 mM of β-alanine within 1 minute using 1.0 mg of aspartase protein is defined as 1 U/mg.

Calculation of Conversion Ratio:

Conversion ratio %=A/B×100%, where A is the molar concentration of produced β-alanine in mM, and B is the initial molar concentration of acrylic acid in the unit of mol/L.

Calculation of Enzyme Activity Per Unit Cell:

Enzyme activity per unit cell=molar concentration of produced β-alanine/reaction time/concentration of cell, where the unit of reaction time is min, and the cell concentration is $OD_{550}$ value in the reaction system.

Calculation of Enzyme Activity Per Unit Protein:

Enzyme activity per unit protein=molar concentration of produced β-alanine/reaction time/concentration of protein, where the unit of reaction time is min, and the concentration of protein is the crude enzyme protein concentration in the reaction system, in the unit of g/L.

VII. Relative Enzyme Activity

Mixing 25 mg of the crude enzyme protein of wild type aspartase or a variant thereof with 1.0 mL of a 400 mM substrate at pH 8.0, stirring at 40° C. for 1.0 h of reaction, and then its catalytic activity of ammoniation of acrylic acid is measured.

Relative enzyme activity is the ratio of the activity of the aspartase variant enzyme activity to the wild type aspartase enzyme activity. The results of the relative enzyme activity of the aspartase variants are shown in Table 1.

TABLE 1

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB001 | protein: | T187I/N326C | 5.42 |
| | gene: | C560T/G561T/A976T/A977G/T978C | |
| AHB002 | protein: | V75E/Q89H/T187I/L258I/N326C/K381R/K389I | 12.77 |
| | gene: | T224A/A267T/C560T/G561T/T772A/A774T/A976T/A977G/T978C/A1141C/A1142G/A1143T/A1166T/A1167C | |
| AHB003 | protein: | D20V/Q89H/L156F/T164I/T187I/Y204C/L258I/M285L/N326C/K381R/R426C | 28.59 |
| | gene: | A59T/C60G/A267T/A468T/C491T/A492T/C560T/G561T/A611G/T612C/T772A/A774T/A853C/A976T/A977G/T978C/A1141C/A1142G/A1143T/C1276T/T1278C | |
| AHB004 | protein: | Q89H/L156F/T164I/T187I/L258I/N326C/K389I/I406L/R426C | 28.05 |
| | gene: | A267T/A468T/C491T/A492T/C560T/G561T/T772A/A774T/A976T/A977G/T978C/A1166T/A1167C/A1216T/T1218G/C1276T/T1278C | |
| AHB005 | protein: | L156F/T187I/Y204C/K324I/N326C/K389I/I406L | 26.98 |
| | gene: | A468T/C560T/G561T/A611G/T612C/A971T/A972T/A976T/A977G/T978C/A1166T/A1167C/A1216T/T1218G | |
| AHB006 | protein: | T187I/N226I/M285L/M321I/K324I/N326C/K381R/K389I/I406L/P456L | 13.95 |
| | gene: | C560T/G561T/A677T/C678T/A853C/G963T/A971T/A972T/A976T/A977G/T978C/A1141C/A1142G/A1143T/A1166T/A1167C/A1216T/T1218G/C1366T/C1367T/A1368G | |
| AHB007 | protein: | D20V/Q89H/L156F/T187I/M285L/N326C/K381R/K389I | 21.02 |
| | gene: | A59T/C60G/A267T/A468T/C560T/G561T/A853C/A976T/A977G/T978C/A1141C/A1142G/A1143T/A1166T/A1167C | |
| AHB008 | protein: | D20V/Q89H/T164I/T187I/Y204C/N226I/K324I/N326C | 39.97 |
| | gene: | A59T/C60G/A267T/C491T/A492T/C560T/G561T/A611G/T612C/A677T/C678T/A971T/A972T/A976T/A977G/T978C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB0 09 | protein: | L156F/T164I/T187I/L258I/N326C/I406L/R426C | 31.14 |
| | gene: | A468T/C491T/A492T/C560T/G561T/T772A/A774T/A976T/ A977G/T978C/A1216T/T1218G/C1276T/T1278C | |
| AHB0 10 | protein: | V75E/T187I/N226I/L258I/K324I/N326C/K381R/I406L | 36.16 |
| | gene: | T224A/C560T/G561T/A677T/C678T/T772A/A774T/A971T/ A972T/A976T/A977G/T978C/A1141C/A1142G/A1143T/ A1216T/T1218G | |
| AHB0 11 | protein: | V75E/T187I/L258I/M285L/N326C/I406L | 6.70 |
| | gene: | T224A/C560T/G561T/T772A/A774T/A853C/A976T/A977G/ T978C/A1216T/T1218G | |
| AHB0 12 | protein: | L156F/T187I/N226I/L258I/N326C/I406L | 22.48 |
| | gene: | A468T/C560T/G561T/A677T/C678T/T772A/A774T/A976T/ A977G/T978C/A1216T/T1218G | |
| AHB0 13 | protein: | D20V/L156F/T164I/T187I/N226I/M285L/M321I/K324I/ N326C/I406L/R426C | 6.87 |
| | gene: | A59T/C60G/A468T/C491T/A492T/C560T/G561T/A677T/ C678T/A853C/G963T/A971T/A972T/A976T/A977G/T978C/ A1216T/T1218G/C1276T/T1278C | |
| AHB0 14 | protein: | V75E/T187I/N226I/M321I/K324I/N326C/P456L | 11.06 |
| | gene: | T224A/C560T/G561T/A677T/C678T/G963T/A971T/A972T/ A976T/A977G/T978C/C1366T/C1367T/A1368G | |
| AHB0 15 | protein: | V75E/Q89H/L156F/T187I/N326C/K381R/R426C | 22.81 |
| | gene: | T224A/A267T/A468T/C560T/G561T/A976T/A977G/T978C/ A1141C/A1142G/A1143T/C1276T/T1278C | |
| AHB0 16 | protein: | T187I/N226I/M321I/N326C/K389I/I406L | 14.50 |
| | gene: | C560T/G561T/A677T/C678T/G963T/A976T/A977G/T978C/ A1166T/A1167C/A1216T/T1218G | |
| AHB0 17 | protein: | V75E/L156F/T187I/M285L/M321I/K324I/N326C/K381R/P456L | 20.35 |
| | gene: | T224A/A468T/C560T/G561T/A853C/G963T/A971T/A972T/ A976T/A977G/T978C/A1141C/A1142G/A1143T/C1366T/ C1367T/A1368G | |
| AHB0 18 | protein: | Q89H/L156F/T164I/T187I/Y204C/N226I/M285L/K324I/ N326C/K381R | 6.32 |
| | gene: | A267T/A468T/C491T/A492T/C560T/G561T/A611G/T612C/ A677T/C678T/A853C/A971T/A972T/A976T/A977G/T978C/ A1141C/A1142G/A1143T | |
| AHB0 19 | protein: | T187I/N226I/M321I/N326C/I406L/R426C | 26.72 |
| | gene: | C560T/G561T/A677T/C678T/G963T/A976T/A977G/T978C/ A1216T/T1218G/C1276T/T1278C | |
| AHB0 20 | protein: | V75E/L156F/T187I/N226I/L258I/M285L/N326C | 36.12 |
| | gene: | T224A/A468T/C560T/G561T/A677T/C678T/T772A/A774T/ A853C/A976T/A977G/T978C | |
| AHB0 21 | protein: | V75E/Q89H/L156F/T164I/T187I/N226I/N326C/K389I/ I406L | 7.49 |
| | gene: | T224A/A267T/A468T/C491T/A492T/C560T/G561T/A677T/ C678T/A976T/A977G/T978C/A1166T/A1167C/A1216T/T1218G | |
| AHB0 22 | protein: | Q89H/T164I/T187 VY204C/N226I/K324I/N326C/K381R/ R426C | 26.81 |
| | gene: | A267T/C491T/A492T/C560T/G561T/A611G/T612C/A677T/ C678T/A971T/A972T/A976T/A977G/T978C/A1141C/A1142G/ A1143T/C1276T/T1278C | |
| AHB0 23 | protein: | D20V/Q89H/L156F/T187I/Y204C/M285L/K324I/N326C/K381R/ K389I | 47.97 |
| | gene: | A59T/C60G/A267T/A468T/C560T/G561T/A611G/T612C/ A853C/A971T/A972T/A976T/A977G/T978C/A1141C/ A1142G/A1143T/A1166T/A1167C | |
| AHB0 24 | protein: | D20V/T164I/T187I/N226I/L258I/M285L/K324I/N326C | 43.46 |
| | gene: | A59T/C60G/C491T/A492T/C560T/G561T/A677T/C678T/ T772A/A774T/A853C/A971T/A972T/A976T/A977G/T978C | |
| AHB0 25 | protein: | V75E/Q89H/T187I/Y204C/L258I/M321I/N326C/K381R/ K389I/I406L/R426C | 39.17 |
| | gene: | T224A/A267T/C560T/G561T/A611G/T612C/T772A/A774T/ G963T/A976T/A977G/T978C/A1141C/A1142G/A1143T/ A1166T/A1167C/A1216T/T1218G/C1276T/T1278C | |
| AHB0 26 | protein: | V75E/Q89H/T164I/T187I/Y204C/N226I/M285L/M321I/ N326C/K389I/R426C | 44.00 |
| | gene: | T224A/A267T/C491T/A492T/C560T/G561T/A611G/T612C/ A677T/C678T/A853C/G963T/A976T/A977G/T978C/A1166T/ A1167C/C1276T/T1278C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB0 27 | protein: | D20V/V75E/T187I/N226I/L258I/M285L/N326C/R426C | 31.40 |
| | gene: | A59T/C60G/T224A/C560T/G561T/A677T/C678T/T772A/ A774T/A853C/A976T/A977G/T978C/C1276T/T1278C | |
| AHB0 28 | protein: | D20V/Q89H/L156F/T187I/N226I/N326C/K381R/K389I | 30.12 |
| | gene: | A59T/C60G/A267T/A468T/C560T/G561T/A677T/C678T/ A976T/A977G/T978C/A1141C/A1142G/A1143T/A1166T/ A1167C | |
| AHB0 29 | protein: | D20V/V75E/L156F/T187I/N226I/M321I/K324I/N326C/ R426C/P456L | 38.56 |
| | gene: | A59T/C60G/T224A/A468T/C560T/G561T/A677T/C678T/ G963T/A971T/A972T/A976T/A977G/T978C/C1276T/ T1278C/C1366T/C1367T/A1368G | |
| AHB0 30 | protein: | V75E/Q89H/T164I/T187I/M321I/N326C/K381R/K389I/R426C | 28.92 |
| | gene: | T224A/A267T/C491T/A492T/C560T/G561T/G963T/A976T/ A977G/T978C/A1141C/A1142G/A1143T/A1166T/A1167C/ C1276T/T1278C | |
| AHB0 31 | protein: | D20V/V75E/T164I/T187I/Y204C/M285L/M321I/N326C/ K381R/R426C | 16.78 |
| | gene: | A59T/C60G/T224A/C491T/A492T/C560T/G561T/A611G/ T612C/A853C/G963T/A976T/A977G/T978C/A1141C/A1142G/ A1143T/C1276T/T1278C | |
| AHB0 32 | protein: | V75E/T164I/T187I/M321I/N326C/K381R/I406L | 27.79 |
| | gene: | T224A/C491T/A492T/C560T/G561T/G963T/A976T/A977G/ T978C/A1141C/A1142G/A1143T/A1216T/T1218G | |
| AHB0 33 | protein: | V75E/L156F/T187I/Y204C/M321I/N326C/K389I/R426C | 46.48 |
| | gene: | T224A/A468T/C560T/G561T/A611G/T612C/G963T/A976T/ A977G/T978C/A1166T/A1167C/C1276T/T1278C | |
| AHB0 34 | protein: | T187I/M285L/N326C/I406L/R426C/P456L | 26.52 |
| | gene: | C560T/G561T/A853C/A976T/A977G/T978C/A1216T/T1218G/ C1276T/T1278C/C1366T/C1367T/A1368G | |
| AHB0 35 | protein: | D20V/Q89H/T164I/T187I/M285L/N326C/K381R | 37.80 |
| | gene: | A59T/C60G/A267T/C491T/A492T/C560T/G561T/A853C/ A976T/A977G/T978C/A1141C/A1142G/A1143T | |
| AHB0 36 | protein: | Q89H/T187I/Y204C/L258I/M321I/K324I/N326C/K381R/ R426C | 7.01 |
| | gene: | A267T/C560T/G561T/A611G/T612C/T772A/A774T/G963T/ A971T/A972T/A976T/A977G/T978C/A1141C/A1142G/ A1143T/C1276T/T1278C | |
| AHB0 37 | protein: | V75E/Q89H/T187I/Y204C/L258I/M285L/M321I/N326C/ I406L/R426C | 26.53 |
| | gene: | T224A/A267T/C560T/G561T/A611G/T612C/T772A/A774T/ A853C/G963T/A976T/A977G/T978C/A1216T/T1218G/ C1276T/T1278C | |
| AHB0 38 | protein: | D20V/T187I/Y204C/L258I/N326C/K381R | 24.57 |
| | gene: | A59T/C60G/C560T/G561T/A611G/T612C/T772A/A774T/ A976T/A977G/T978C/A1141C/A1142G/A1143T | |
| AHB0 39 | protein: | T187I/N226I/N326C/I406L/P456L | 10.62 |
| | gene: | C560T/G561T/A677T/C678T/A976T/A977G/T978C/A1216T/ T1218G/C1366T/C1367T/A1368G | |
| AHB0 40 | protein: | D20V/L156F/T187I/L258I/M321I/K324I/N326C | 39.70 |
| | gene: | A59T/C60G/A468T/C560T/G561T/T772A/A774T/G963T/ A971T/A972T/A976T/A977G/T978C | |
| AHB0 41 | protein: | V75E/Q89H/L156F/T187I/M321I/N326C/R426C | 10.19 |
| | gene: | T224A/A267T/A468T/C560T/G561T/G963T/A976T/A977G/ T978C/C1276T/T1278C | |
| AHB0 42 | protein: | T187I/Y204C/N226I/M285L/M321I/N326C/K381R/K389I/ I406L/P456L | 31.57 |
| | gene: | C560T/G561T/A611G/T612C/A677T/C678T/A853C/G963T/ A976T/A977G/T978C/A1141C/A1142G/A1143T/A1166T/ A1167C/A1216T/T1218G/C1366T/C1367T/A1368G | |
| AHB0 43 | protein: | Q89H/T187I/N226I/M285L/M321I/K324I/N326C/K389I | 38.43 |
| | gene: | A267T/C560T/G561T/A677T/C678T/A853C/G963T/A971T/ A972T/A976T/A977G/T978C/A1166T/A1167C | |
| AHB0 44 | protein: | V75E/L156F/T164I/T187I/Y204C/N226I/L258I/N326C/ I406L | 28.65 |
| | gene: | T224A/A468T/C491T/A492T/C560T/G561T/A611G/T612C/ A677T/C678T/T772A/A774T/A976T/A977G/T978C/A1216T/ T1218G | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB0 45 | protein: | V75E/Q89H/L156F/T164I/T187I/Y204C/M285L/N326C/K381R/K389I/R426C | 40.19 |
| | gene: | T224A/A267T/A468T/C491T/A492T/C560T/G561T/A611G/T612C/A853C/A976T/A977G/T978C/A1141C/A1142G/A1143T/A1166T/A1167C/C1276T/T1278C | |
| AHB0 46 | protein: | D20V/V75E/L156F/T187I/N326C/K381R/R426C | 32.80 |
| | gene: | A59T/C60G/T224A/A468T/C560T/G561T/A976T/A977G/T978C/A1141C/A1142G/A1143T/C1276T/T1278C | |
| AHB0 47 | protein: | V75E/T187I/L258I/N326C/K381R | 30.10 |
| | gene: | T224A/C560T/G561T/T772A/A774T/A976T/A977G/T978C/A1141C/A1142G/A1143T | |
| AHB0 48 | protein: | D20V/V75E/T164I/T187I/M285L/M321I/N326C/K381R/R426C | 15.71 |
| | gene: | A59T/C60G/T224A/C491T/A492T/C560T/G561T/A853C/G963T/A976T/A977G/T978C/A1141C/A1142G/A1143T/C1276T/T1278C | |
| AHB0 49 | protein: | T187I/N226I/L258I/N326C/I406L | 23.15 |
| | gene: | C560T/G561T/A677T/C678T/T772A/A774T/A976T/A977G/T978C/A1216T/T1218G | |
| AHB0 50 | protein: | V75E/T164I/T187I/M321I/N326C/I406L | 18.38 |
| | gene: | T224A/C491T/A492T/C560T/G561T/G963T/A976T/A977G/T978C/A1216T/T1218G | |
| AHB0 51 | protein: | T187I/L258I/M285L/M321I/N326C | 40.49 |
| | gene: | C560T/G561T/T772A/A774T/A853C/G963T/A976T/A977G/T978C | |
| AHB0 52 | protein: | D20V/Q89H/T187I/Y204C/L258I/M285L/N326C/K389I | 29.46 |
| | gene: | A59T/C60G/A267T/C560T/G561T/A611G/T612C/T772A/A774T/A853C/A976T/A977G/T978C/A1166T/A1167C | |
| AHB0 53 | protein: | D20V/T187I/L258I/K324I/N326C/R426C | 18.66 |
| | gene: | A59T/C60G/C560T/G561T/T772A/A774T/A971T/A972T/A976T/A977G/T978C/C1276T/T1278C | |
| AHB0 54 | protein: | T187I/Y204C/M285L/N326C/K381R | 11.17 |
| | gene: | C560T/G561T/A611G/T612C/A853C/A976T/A977G/T978C/A1141C/A1142G/A1143T | |
| AHB0 55 | protein: | T187I/Y204C/L258I/M285L/M321I/K324I/N326C/K381R/K389I/I406L | 47.71 |
| | gene: | C560T/G561T/A611G/T612C/T772A/A774T/A853C/G963T/A971T/A972T/A976T/A977G/T978C/A1141C/A1142G/A1143T/A1166T/A1167C/A1216T/T1218G | |
| AHB0 56 | protein: | Q89H/T187I/L258I/M285L/K324I/N326C/I406L | 24.72 |
| | gene: | A267T/C560T/G561T/T772A/A774T/A853C/A971T/A972T/A976T/A977G/T978C/A1216T/T1218G | |
| AHB0 57 | protein: | D20V/V75E/T187I/N226I/L258I/K324I/N326C/K381R/K389I/P456L | 6.24 |
| | gene: | A59T/C60G/T224A/C560T/G561T/A677T/C678T/T772A/A774T/A971T/A972T/A976T/A977G/T978C/A1141C/A1142G/A1143T/A1166T/A1167C/C1366T/C1367T/A1368G | |
| AHB0 58 | protein: | D20V/T164I/T187I/N226I/L258I/N326C/K389I | 33.98 |
| | gene: | A59T/C60G/C491T/A492T/C560T/G561T/A677T/C678T/T772A/A774T/A976T/A977G/T978C/A1166T/A1167C | |
| AHB0 59 | protein: | T187I/Y204C/N326C/I406L/P456L | 30.76 |
| | gene: | C560T/G561T/A611G/T612C/A976T/A977G/T978C/A1216T/T1218G/C1366T/C1367T/A1368G | |
| AHB0 60 | protein: | D20V/T164I/T187I/L258I/M285L/K324I/N326C/I406L | 11.13 |
| | gene: | A59T/C60G/C491T/A492T/C560T/G561T/T772A/A774T/A853C/A971T/A972T/A976T/A977G/T978C/A1216T/T1218G | |
| AHB0 61 | protein: | Q89H/T187I/M285L/N326C/K381R | 30.26 |
| | gene: | A267T/C560T/G561T/A853C/A976T/A977G/T978C/A1141C/A1142G/A1143T | |
| AHB0 62 | protein: | V75E/T187I/L258I/K324I/N326C/K389I/R426C/P456L | 15.54 |
| | gene: | T224A/C560T/G561T/T772A/A774T/A971T/A972T/A976T/A977G/T978C/A1166T/A1167C/C1276T/T1278C/C1366T/C1367T/A1368G | |
| AHB0 63 | protein: | D20V/Q89H/L156F/T187I/N226I/M321I/N326C/K381R/I406L | 40.82 |
| | gene: | A59T/C60G/A267T/A468T/C560T/G561T/A677T/C678T/G963T/A976T/A977G/T978C/A1141C/A1142G/A1143T/A1216T/T1218G | |

TABLE 1-continued

Aspartase variant protein, gene mutation sites and the relative results of the catalytic activity of the ammoniation of acrylic acid

| Variants | | substitutions | relative activity Variants/ WT |
|---|---|---|---|
| WT | — | — | WT |
| AHB0 64 | protein: | V75E/T164I/T187I/N226I/M285L/K324I/N326C/K381R | 47.01 |
| | gene: | T224A/C491T/A492T/C560T/G561T/A677T/C678T/A853C/ A971T/A972T/A976T/A977G/T978C/A1141C/A1142G/A1143T | |
| AHB0 65 | protein: | V75E/L156F/T164I/T187I/L258I/M285L/M321I/N326C/ K381R/K389I/R426C | 37.95 |
| | gene: | T224A/A468T/C491T/A492T/C560T/G561T/T772A/A774T/ A853C/G963T/A976T/A977G/T978C/A1141C/A1142G/ A1143T/A1166T/A1167C/C1276T/T1278C | |
| AHB0 66 | protein: | V75E/T164I/T187I/L258I/M2 85L/M321I/N326C/K381R/ K389I/I406L/R426C | 34.24 |
| | gene: | T224A/C491T/A492T/C560T/G561T/T772A/A774T/A853C/ G963T/A976T/A977G/T978C/A1141C/A1142G/A1143T/ A1166T/A1167C/A1216T/T1218C/C1276T/T1278C | |
| AHB0 67 | protein: | D20V/V75E/Q89H/T187FL258I/M285L/M321I/N326C/ K389I | 39.39 |
| | gene: | A59T/C60G/T224A/A267T/C560T/G561T/T772A/A774T/ A853C/G963T/A976T/A977G/T978C/A1166T/A1167C | |
| AHB0 68 | protein: | T187I/N326C/K381R/K389I/P456L | 19.34 |
| | gene: | C560T/G561T/A976T/A977G/T978C/A1141C/A1142G/ A1143T/A1166T/A1167C/C1366T/C1367T/A1368G | |
| AHB0 69 | protein: | T164I/T187I/N226I/M285L/N326C/R426C | 27.35 |
| | gene: | C491T/A492T/C560T/G561T/A677T/C678T/A853C/A976T/ A977G/T978C/C1276T/T1278C | |
| AHB0 70 | protein: | D20V/V75E/Q89H/L156F/T187I/L258I/M285L/K324I/ N326C | 19.80 |
| | gene: | A59T/C60G/T224A/A267T/A468T/C560T/G561T/T772A/ A774T/A853C/A971T/A972T/A976T/A977G/T978C | |
| AHB0 71 | protein: | D20V/V75E/Q89H/T164I/T187I/Y204C/L258I/M285L/ K324I/N326C | 17.80 |
| | gene: | A59T/C60G/T224A/A267T/C491T/A492T/C560T/G561T/ A611G/T612C/T772A/A774T/A853C/A971T/A972T/A976T/ A977G/T978C | |
| AHB0 72 | protein: | L156F/T164I/T187I/K324I/N326C/R426C | 33.38 |
| | gene: | A468T/C491T/A492T/C560T/G561T/A971T/A972T/A976T/ A977G/T978C/C1276T/T1278C | |
| AHB0 73 | protein: | D20V/V75E/L156F/T164I/T187I/L258I/M321I/K324I/N326C/ K381R/I406L | 14.46 |
| | gene: | A59T/C60G/T224A/A468T/C491T/A492T/C560T/G561T/ T772A/A774T/G963T/A971T/A972T/A976T/A977G/T978C/ A1141C/A1142G/A1143T/A1216T/T1218G | |
| AHB0 74 | protein: | D20V/T187I/N226I/L258I/N326C/I406L | 36.54 |
| | gene: | A59T/C60G/C560T/G561T/A677T/C678T/T772A/A774T/ A976T/A977G/T978C/A1216T/T1218G | |
| AHB0 75 | protein: | V75E/Q89H/L156F/T187I/M321I/K324I/N326C | 18.52 |
| | gene: | T224A/A267T/A468T/C560T/G561T/G963T/A971T/A972T/ A976T/A977G/T978C | |
| AHB0 76 | protein: | L156F/T164I/T187I/K324I/N326C/K381R | 11.35 |
| | gene: | A468T/C491T/A492T/C560T/G561T/A971T/A972T/A976T/ A977G/T978C/A1141C/A1142G/A1143T | |
| AHB0 77 | protein: | L156F/T164I/T187I/L258I/K324I/N326C | 35.52 |
| | gene: | A468T/C491T/A492T/C560T/G561T/T772A/A774T/A971T/ A972T/A976T/A977G/T978C | |
| AHB0 78 | protein: | D20V/V75E/Q89H/L156F/T187I/Y204C/L258I/M321I/ N326C/K389I/I406L | 34.31 |
| | gene: | A59T/C60G/T224A/A267T/A468T/C560T/G561T/A611G/ T612C/T772A/A774T/G963T/A976T/A977G/T978C/A1166T/ A1167C/A1216T/T1218G | |
| AHB0 79 | protein: | T187I/M285L/N326C/I406L/R426C | 30.55 |
| | gene: | C560T/G561T/A853C/A976T/A977G/T978C/A1216T/ T1218G/C1276T/T1278C | |
| AHB0 80 | protein: | T187I/N226I/N326C/K381R/P456L | 22.81 |
| | gene: | C560T/G561T/A677T/C678T/A976T/A977G/T978C/A1141C/ A1142G/A1143T/C1366T/C1367T/A1368G | |
| AHB0 81 | protein: | D20V/T164I/T187I/Y204C/M285L/K324I/N326C/K389I/ R426C | 45.15 |
| | gene: | A59T/C60G/C491T/A492T/C560T/G561T/A611G/T612C/ A853C/A971T/A972T/A976T/A977G/T978C/A1166T/A1167C/ C1276T/T1278C | |

TABLE 1-continued

Aspartase variant protein, gene mutation sites and the relative results of the catalytic activity of the ammoniation of acrylic acid

| Variants | | substitutions | relative activity Variants/ WT |
|---|---|---|---|
| WT | — | — | WT |
| AHB0 82 | protein: | V75E/T187I/N326C/K381R/I406L | 27.19 |
| | gene: | T224A/C560T/G561T/A976T/A977G/T978C/A1141C/ A1142G/A1143T/A1216T/T1218G | |
| AHB0 83 | protein: | T187I/Y204C/N326C/K381R/K389I | 20.17 |
| | gene: | C560T/G561T/A611G/T612C/A976T/A977G/T978C/A1141C/ A1142G/A1143T/A1166T/A1167C | |
| AHB0 84 | protein: | T187I/N226I/L258I/M285L/M321I/N326C | 10.19 |
| | gene: | C560T/G561T/A677T/C678T/T772A/A774T/A853C/ G963T/A976T/A977G/T978C | |
| AHB0 85 | protein: | D20V/L156F/T187I/M285L/M321I/K324I/N326C/K389I | 49.44 |
| | gene: | A59T/C60G/A468T/C560T/G561T/A853C/G963T/A971T/ A972T/A976T/A977G/T978C/A1166T/A1167C | |
| AHB0 86 | protein: | D20V/L156F/T187I/Y204C/N326C/K389I/I406L/R426C | 54.78 |
| | gene: | A59T/C60G/A468T/C560T/G561T/A611G/T612C/A976T/ A977G/T978C/A1166T/A1167C/A1216T/T1218G/C1276T/ T1278C | |
| AHB0 87 | protein: | T164I/T187I/K324I/N326C/K389I/R426C | 33.11 |
| | gene: | C491T/A492T/C560T/G561T/A971T/A972T/A976T/A977G/ T978C/A1166T/A1167C/C1276T/T1278C | |
| AHB0 88 | protein: | V75E/Q89H/T187I/M321I/K324I/N326C/I406L | 27.31 |
| | gene: | T224A/A267T/C560T/G561T/G963T/A971T/A972T/A976T/ A977G/T978C/A1216T/T1218G | |
| AHB0 89 | protein: | V75E/T187I/L258I/N326C/K389I | 42.27 |
| | gene: | T224A/C560T/G561T/T772A/A774T/A976T/A977G/T978C/ A1166T/A1167C | |
| AHB0 90 | protein: | D20V/V75E/L156F/T187I/N326C/K389I/I406L/R426C | 47.72 |
| | gene: | A59T/C60G/T224A/A468T/C560T/G561T/A976T/A977G/ T978C/A1166T/A1167C/A1216T/T1218G/C1276T/T1278C | |
| AHB0 91 | protein: | D20V/Q89H/T164I/T187I/N226I/N326C/K389I/I406L | 16.27 |
| | gene: | A59T/C60G/A267T/C491T/A492T/C560T/G561T/A677T/ C678T/A976T/A977G/T978C/A1166T/A1167C/A1216T/T1218G | |
| AHB0 92 | protein: | D20V/Q89H/L156F/T164I/T187I/L258I/M285L/N326C/ K381R/R426C | 37.40 |
| | gene: | A59T/C60G/A267T/A468T/C491T/A492T/C560T/G561T/ T772A/A774T/A853C/A976T/A977G/T978C/A1141C/A1142G/ A1143T/C1276T/T1278C | |
| AHB0 93 | protein: | V75E/T164I/T187I/N226I/K324I/N326C/I406L | 21.06 |
| | gene: | T224A/C491T/A492T/C560T/G561T/A677T/C678T/A971T/ A972T/A976T/A977G/T978C/A1216T/T1218G | |
| AHB0 94 | protein: | D20V/T164ET187I/L258I/M321I/N326C/K389I | 34.04 |
| | gene: | A59T/C60G/C491T/A492T/C560T/G561T/T772A/A774T/ G963T/A976T/A977G/T978C/A1166T/A1167C | |
| AHB0 95 | protein: | T187I/N226I/M285L/N326C/K381R/K389I | 27.16 |
| | gene: | C560T/G561T/A677T/C678T/A853C/A976T/A977G/T978C/ A1141C/A1142G/A1143T/A1166T/A1167C | |
| AHB0 96 | protein: | T187I/N226I/L258I/M285L/M321I/K324I/N326C/K381R/ K389I/P456L | 21.09 |
| | gene: | C560T/G561T/A677T/C678T/T772A/A774T/A853C/G963T/ A971T/A972T/A976T/A977G/T978C/A1141C/A1142G/ A1143T/A1166T/A1167C/C1366T/C1367T/A1368G | |
| AHB0 97 | protein: | V75E/Q89H/L156F/T187I/M321I/N326C/I406L | 13.79 |
| | gene: | T224A/A267T/A468T/C560T/G561T/G963T/A976T/A977G/ T978C/A1216T/T1218G | |
| AHB0 98 | protein: | D20V/Q89H/L156F/T164I/T187I/N226I/M321I/N326C/ K389I/I406L/R426C | 15.28 |
| | gene: | A59T/C60G/A267T/A468T/C491T/A492T/C560T/G561T/ A677T/C678T/G963T/A976T/A977G/T978C/A1166T/A1167C/ A1216T/T1218G/C1276T/T1278C | |
| AHB0 99 | protein: | V75E/T187I/Y204C/M285L/M321I/N326C/K381R/I406L/ P456L | 12.73 |
| | gene: | T224A/C560T/G561T/A611G/T612C/A853C/G963T/A976T/ A977G/T978C/A1141C/A1142G/A1143T/A1216T/T1218G/ C1366T/C1367T/A1368G | |
| AHB1 00 | protein: | Q89H/T164I/T187I/M285L/M321I/N326C/K381R/K389I | 30.85 |
| | gene: | A267T/C491T/A492T/C560T/G561T/A853C/G963T/A976T/ A977G/T978C/A1141C/A1142G/A1143T/A1166T/A1167C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB1 01 | protein: | T187I/N226I/L258I/M285L/M321I/N326C/K381R/I406L/R426C/P456L | 47.93 |
| | gene: | C560T/G561T/A677T/C678T/T772A/A774T/A853G/G963T/A976T/A977G/T978C/A1141C/A1142G/A1143T/A1216T/T1218G/C1276T/T1278C/C1366T/C1367T/A1368G | |
| AHB1 02 | protein: | L156F/T187I/Y204C/M321I/K324I/N326C | 26.75 |
| | gene: | A468T/C560T/G561T/A611G/T612C/G963T/A971T/A972T/A976T/A977G/T978C | |
| AHB1 03 | protein: | D20V/L156F/T164I/T187I/M321I/K324I/N326C | 22.66 |
| | gene: | A59T/C60G/A468T/C491T/A492T/C560T/G561T/G963T/A971T/A972T/A976T/A977G/T978C | |
| AHB1 04 | protein: | T187I/Y204C/L258I/K324I/N326C | 18.88 |
| | gene: | C560T/G561T/A611G/T612C/T772A/A774T/A971T/A972T/A976T/A977G/T978C | |
| AHB1 05 | protein: | T164I/T187I/N226I/M285L/M321I/K324I/N326C/K381R/I406L/R426C | 32.02 |
| | gene: | C491T/A492T/C560T/G561T/A677T/C678T/A853G/G963T/A971T/A972T/A976T/A977G/T978C/A1141C/A1142G/A1143T/A1216T/T1218G/C1276T/T1278C | |
| AHB1 06 | protein: | D20V/T164I/T187I/Y204C/N226I/N326C/K389I/I406L | 27.92 |
| | gene: | A59T/C60G/C491T/A492T/C560T/G561T/A611G/T612C/A677T/C678T/A976T/A977G/T978C/A1166T/A1167C/A1216T/T1218G | |
| AHB1 07 | protein: | L156F/T187I/Y204C/N226I/M285L/M321I/N326C/I406L/R426C/P456L | 26.52 |
| | gene: | A468T/C560T/G561T/A611G/T612C/A677T/C678T/A853C/G963T/A976T/A977G/T978C/A1216T/T1218G/C1276T/T1278C/C1366T/C1367T/A1368G | |
| AHB1 08 | protein: | V75E/Q89H/L156F/T187I/K324I/N326C/K389I/R426C/P456L | 35.35 |
| | gene: | T224A/A267T/A468T/C560T/G5 61T/A971T/A972T/A976T/A977G/T978C/A1166T/A1167C/C1276T/T1278C/C1366T/C1367T/A1368G | |
| AHB1 09 | protein: | L156F/T164I/T187I/K324I/N326C/K381R/I406L/R426C | 23.80 |
| | gene: | A468T/C491T/A492T/C560T/G561T/A971T/A972T/A976T/A977G/T978C/A1141C/A1142G/A1143T/A1216T/T1218G/C1276T/T1278C | |
| AHB1 10 | protein: | T164I/T187I/M321I/N326C/I406L | 44.58 |
| | gene: | C491T/A492T/C560T/G561T/G963T/A976T/A977G/T978C/A1216T/T1218G | |
| AHB1 11 | protein: | D20V/Q89H/L156F/T164I/T187I/Y204C/M285L/K324I/N326C/K381R/R426C | 34.80 |
| | gene: | A59T/C60G/A267T/A468T/C491T/A492T/C560T/G561T/A611G/T612C/A853C/A971T/A972T/A976T/A977G/T978C/A1141C/A1142G/A1143T/C1276T/T1278C | |
| AHB1 12 | protein: | L156F/T187I/Y204C/N326C/R426C | 44.44 |
| | gene: | A468T/C560T/G561T/A611G/T612C/A976T/A977G/T978C/C1276T/T1278C | |
| AHB1 13 | protein: | D20V/T164I/T187I/N226I/L258I/N326C/R426C | 18.08 |
| | gene: | A59T/C60G/C491T/A492T/C560T/G561T/A677T/C678T/T772A/A774T/A976T/A977G/T978C/C1276T/T1278C | |
| AHB1 14 | protein: | T187I/Y204C/N226I/L258I/M285L/M321I/N326C/K389I/I406L/R426C | 14.79 |
| | gene: | C560T/G561T/A611G/T612C/A677T/C678T/T772A/A774T/A853C/G963T/A976T/A977G/T978C/A1166T/A1167C/A1216T/T1218G/C1276T/T1278C | |
| AHB1 15 | protein: | D20V/T187I/N226I/N326C/K389I | 41.16 |
| | gene: | A59T/C60G/C560T/G561T/A677T/C678T/A976T/A977G/T978C/A1166T/A1167C | |
| AHB1 16 | protein: | V75E/Q89H/L156F/T187I/L258I/M321I/N326C/I406L/R426C | 20.58 |
| | gene: | T224A/A267T/A468T/C560T/G561T/T772A/A774T/G963T/A976T/A977G/T978C/A1216T/T1218G/C1276T/T1278C | |
| AHB1 17 | protein: | T187I/Y204C/N226I/M285L/N326C/R426C | 52.49 |
| | gene: | C560T/G561T/A611G/T612C/A677T/C678T/A853C/A976T/A977G/T978C/C1276T/T1278C | |
| AHB1 18 | protein: | T187I/Y204C/M285L/N326C/K381R/R426C | 23.80 |
| | gene: | C560T/G561T/A611G/T612C/A853C/A976T/A977G/T978C/A1141C/A1142G/A1143T/C1276T/T1278C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB1 19 | protein: | L156F/T187I/N226I/N326C/K381R | 10.77 |
| | gene: | A468T/C560T/G561T/A677T/C678T/A976T/A977G/T978C/A1141C/A1142G/A1143T | |
| AHB1 20 | protein: | D20V/Q89H/T187I/Y204C/M285L/N326C/R426C | 53.10 |
| | gene: | A59T/C60G/A267T/C560T/G561T/A611G/T612C/A853C/A976T/A977G/T978C/C1276T/T1278C | |
| AHB1 21 | protein: | L156F/T187I/L258I/M285L/M321I/K324I/N326C/K381R/I406L/R426C | 18.82 |
| | gene: | A468T/C560T/G561T/T772A/A774T/A853C/G963T/A971T/A972T/A976T/A977G/T978C/A1141C/A1142G/A1143T/A1216T/C1218G/C1276T/T1278C | |
| AHB1 22 | protein: | T187I/Y204C/L258I/M285L/K324I/N326C | 37.18 |
| | gene: | C560T/G561T/A611G/T612C/T772A/A774T/A853C/A971T/A972T/A976T/A977G/T978C | |
| AHB1 23 | protein: | D20V/T187I/Y204C/N226I/L258I/N326C/I406L/R426C | 43.79 |
| | gene: | A59T/C60G/C560T/G561T/A611G/T612C/A677T/C678T/T772A/A774T/A976T/A977G/T978C/A1216T/C1218G/C1276T/T1278C | |
| AHB1 24 | protein: | D20V/L156F/T187I/N226I/M285L/N326C/K381R | 25.49 |
| | gene: | A59T/C60G/A468T/C560T/G561T/A677T/C678T/A853C/A976T/A977G/T978C/A1141C/A1142G/A1143T | |
| AHB1 25 | protein: | D20V/Q89H/L156F/T187I/M285L/K324I/N326C/K389I | 14.69 |
| | gene: | A59T/C60G/A267T/A468T/C560T/G561T/A853C/A971T/A972T/A976T/A977G/T978C/A1166T/A1167C | |
| AHB1 26 | protein: | V75E/T187I/K324I/N326C/K389I | 39.72 |
| | gene: | T224A/C560T/G561T/A971T/A972T/A976T/A977G/T978C/A1166T/A1167C | |
| AHB1 27 | protein: | Q89H/L156F/T164I/T187I/Y204C/N226I/L258I/M285L/N326C/K389I/R426C | 11.27 |
| | gene: | A267T/A468T/C491T/A492T/C560T/G561T/A611G/T612C/A677T/C678T/T772A/A774T/A853C/A976T/A977G/T978C/A1166T/A1167C/C1276T/T1278C | |
| AHB1 28 | protein: | Q89H/T187I/N226I/L258I/M321I/N326C/K381R/K389I/P456L | 39.78 |
| | gene: | A267T/C560T/G561T/A677T/C678T/T772A/A774T/G963T/A976T/A977G/T978C/A1141C/A1142G/A1143T/A116617 A1167C/C1366T/C1367T/A1368G | |
| AHB1 29 | protein: | D20V/V75E/Q89H/T187I/Y204C/M321I/K324I/N326C/K381R | 39.30 |
| | gene: | A59T/C60G/T224A/A267T/C560T/G561T/A611G/T612C/G963T/A971T/A972T/A976T/A977G/T978C/A1141C/A1142G/A1143T | |
| AHB1 30 | protein: | Q89H/T164I/T187I/M285L/N326C | 34.10 |
| | gene: | A267T/C491T/A492T/C560T/G561T/A853C/A976T/A977G/T978C | |
| AHB1 31 | protein: | T187I/L258I/N326C/K381R/R426C | 22.14 |
| | gene: | C560T/G561T/T772A/A774T/A976T/A977G/T978C/A1141C/A1142G/A1143T/C1276T/T1278C | |
| AHB1 32 | protein: | L156F/T164I/T187I/N326C/K389I | 21.70 |
| | gene: | A468T/C491T/A492T/C560T/G561T/A976T/A977G/T978C/A1166T/A1167C | |
| AHB1 33 | protein: | L156F/T164I/T187I/N226I/N326C/R426C | 51.65 |
| | gene: | A468T/C491T/A492T/C560T/G561T/A677T/C678T/A976T/A977G/T978C/C1276T/T1278C | |
| AHB1 34 | protein: | D20V/Q89H/T187I/Y204C/M285L/M321I/N326C/K381R/R426C | 52.00 |
| | gene: | A59T/C60G/A267T/C560T/G561T/A611G/T612C/A853C/G963T/A976T/A977G/T978C/A1141C/A1142G/A1143T/C1276T/T1278C | |
| AHB1 35 | protein: | V75E/Q89H/T187I/M321I/N326C/K381R/K389I/I406L/P456L | 24.62 |
| | gene: | T224A/A267T/C560T/G561T/G963T/A976T/A977G/T978C/A1141C/A1142G/A1143T/A1166T/A1167C/A1216T/T1218G/C1366T/C1367T/A1368G | |
| AHB1 36 | protein: | D20V/T164I/T187I/M321I/N326C/K389I/P456L | 43.89 |
| | gene: | A59T/C60G/C491T/A492T/C560T/G561T/G963T/A976T/A977G/T978C/A1166T/A1167C/C1366T/C1367T/A1368G | |
| AHB1 37 | protein: | Q89H/T187I/L258I/N326C/P456L | 42.33 |
| | gene: | A267T/C560T/G561T/T772A/A774T/A976T/A977G/T978C/C1366T/C1367T/A1368G | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB1 38 | protein: | V75E/L156F/T164I/T187I/L258I/M285L/N326C/K381R/ K389FR426C | 28.66 |
| | gene: | T224A/A468T/C491T/A492T/C560T/G561T/T772A/A774T/ A853C/A976T/A977G/T978C/A1141C/A1142G/A1143T/ A1166T/A1167C/C1276T/T1278C | |
| AHB1 39 | protein: | T187I/N226I/M285L/K324I/N326C | 18.06 |
| | gene: | C560T/G561T/A677T/C678T/A853C/A971T/A972T/A976T/ A977G/T978C | |
| AHB1 40 | protein: | T187I/L258I/N326C/K381R/K389I/I406L | 14.27 |
| | gene: | C560T/G561T/T772A/A774T/A976T/A977G/T978C/A1141C/ A1142G/A1143T/A1166T/A1167C/A1216T/T1218G | |
| AHB1 41 | protein: | D20V/T187I/L258I/K324I/N326C/I406L | 30.60 |
| | gene: | A59T/C60G/C560T/G561T/T772A/A774T/A971T/A972T/ A976T/A977G/T978C/A1216T/T1218G | |
| AHB1 42 | protein: | V75E/L156F/T164I/T187I/Y204C/L258I/N326C/K389I/ I406L | 37.56 |
| | gene: | T224A/A468T/C491T/A492T/C560T/G561T/A611G/T612C/ T772A/A774T/A976T/A977G/T978C/A1166T/A1167C/ A1216T/T1218G | |
| AHB1 43 | protein: | D20V/Q89H/L156F/T187I/K324I/N326C/K381R/R426C | 14.03 |
| | gene: | A59T/C60G/A267T/A468T/C560T/G561T/A971T/A972T/ A976T/A977G/T978C/A1141C/A1142G/A1143T/C1276T/ T1278C | |
| AHB1 44 | protein: | Q89H/T187I/N226I/M285L/M321I/K324I/N326C | 10.59 |
| | gene: | A267T/C560T/G561T/A677T/C678T/A853C/G963T/A971T/ A972T/A976T/A977G/T978C | |
| AHB1 45 | protein: | T164I/T187I/M285L/M321I/N326C/K381R | 11.91 |
| | gene: | C491T/A492T/C560T/G561T/A853C/G963T/A976T/A977G/ T978C/A1141C/A1142G/A1143T | |
| AHB1 46 | protein: | Q89H/L156F/T187I/Y204C/N226I/M285L/M321I/N326C/ K389I/R426C | 34.37 |
| | gene: | A267T/A468T/C560T/G561T/A611G/T612C/A677T/C678T/ A853C/G963T/A976T/A977G/T978C/A1166T/A1167C/ C1276T/T1278C | |
| AHB1 47 | protein: | Q89H/L156F/T164I/T187I/L258I/N326C/K389I | 34.78 |
| | gene: | A267T/A468T/C491T/A492T/C560T/G561T/T772A/A774T/ A976T/A977G/T978C/A1166T/A1167C | |
| AHB1 48 | protein: | T164I/T187I/N226I/M321I/K324I/N326C/K381R | 29.96 |
| | gene: | C491T/A492T/C560T/G561T/A677T/C678T/G963T/A971T/ A972T/A976T/A977G/T978C/A1141C/A1142G/A1143T | |
| AHB1 49 | protein: | D20V/Q89H/T164I/T187I/Y204C/N226I/M285L/N326C/ K381R/K389I/I406L | 47.59 |
| | gene: | A59T/C60G/A267T/C491T/A492T/C560T/G561T/A611G/ T612C/A677T/C678T/A853C/A976T/A977G/T978C/A1141C/ A1142G/A1143T/A1166T/A1167C/A1216T/T1218G | |
| AHB1 50 | protein: | V75E/T164I/T187I/L258I/N326C/K389I | 26.46 |
| | gene: | T224A/C491T/A492T/C560T/G561T/T772A/A774T/A976T/ A977G/T978C/A1166T/A1167C | |
| AHB1 51 | protein: | T187I/N326C/K389I/I406L/R426C/P456L | 29.62 |
| | gene: | C560T/G561T/A976T/A977G/T978C/A1166T/A1167C/A1216T/ T1218G/C1276T/T1278C/C1366T/C1367T/A1368G | |
| AHB1 52 | protein: | V75E/T187I/N326C/K381R/K389I/I406L/R426C | 15.74 |
| | gene: | T224A/C560T/G561T/A976T/A977G/T978C/A1141C/A1142G/ A1143T/A1166T/A1167C/A1216T/T1218G/C1276T/ T1278C | |
| AHB1 53 | protein: | T187I/L258I/M321I/N326C/I406L | 36.73 |
| | gene: | C560T/G561T/T772A/A774T/G963T/A976T/A977G/T978C/ A1216T/T1218G | |
| AHB1 54 | protein: | Q89H/L156F/T164I/T187I/Y204C/N226I/K324I/N326C/ P456L | 47.99 |
| | gene: | A267T/A468T/C491T/A492T/C560T/G561T/A611G/T612C/ A677T/C678T/A971T/A972T/A976T/A977G/T978C/C1366T/ C1367T/A1368G | |
| AHB1 55 | protein: | T187I/N226I/L258I/M285L/M321I/K324I/N326C/I406L/ R426C/P456L | 29.70 |
| | gene: | C560T/G561T/A677T/C678T/T772A/A774T/A853C/G963T/ A971T/A972T/A976T/A977G/T978C/A1216T/T1218G/ C1276T/T1278C/C1366T/C1367T/A1368G | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB1 56 | protein: | D20V/T187I/M285L/N326C/K381R | 49.63 |
| | gene: | A59T/C60G/C560T/G561T/A853C/A976T/A977G/T978C/ A1141C/A1142G/A1143T | |
| AHB1 57 | protein: | V75E/T187I/Y204C/M321I/N326C | 39.42 |
| | gene: | T224A/C560T/G561T/A611G/T612C/G963T/A976T/A977G/ T978C | |
| AHB1 58 | protein: | T164I/T187I/Y204C/L258I/K324I/N326C/K389I | 40.96 |
| | gene: | C491T/A492T/C560T/G561T/A611G/T612C/T772A/A774T/ A971T/A972T/A976T/A977G/T978C/A1166T/A1167C | |
| AHB1 59 | protein: | V75E/L156F/T164I/T187I/Y204C/L258I/M285L/M321I/N326C/ K389I/I406L | 49.07 |
| | gene: | T224A/A468T/C491T/A492T/C560T/G561T/A611G/T612C/ T772A/A774T/A853C/G963T/A976T/A977G/T978C/A1166T/ A1167C/A1216T/T1218G | |
| AHB1 60 | protein: | V75E/T164I/T187I/L258I/M285L/M321I/K324I/N326C/I406L/ R426C | 39.24 |
| | gene: | T224A/C491T/A492T/C560T/G561T/T772A/A774T/A853C/ G963T/A971T/A972T/A976T/A977G/T978C/A1216T/ T1218G/C1276T/T1278C | |
| AHB1 61 | protein: | D20V/T187I/M285L/N326C/K389I/I406L/R426C | 25.46 |
| | gene: | A59T/C60G/C560T/G561T/A853C/A976T/A977G/T978C/ A1166T/A1167C/A1216T/T1218G/C1276T/T1278C | |
| AHB1 62 | protein: | T187I/M285L/M321I/N326C/R426C | 37.91 |
| | gene: | C560T/G561T/A853C/G963T/A976T/A977G/T978C/C1276T/ T1278C | |
| AHB1 63 | protein: | Q89H/L156F/T164I/T187I/N226I/L258I/M321I/K324I/N326C | 47.32 |
| | gene: | A267T/A468T/C491T/A492T/C560T/G561T/A677T/C678T/ T772A/A774T/G963T/A971T/A972T/A976T/A977G/T978C | |
| AHB1 64 | protein: | Q89H/T164I/T187I/Y204C/L258I/N326C | 40.15 |
| | gene: | A267T/C491T/A492T/C560T/G561T/A611G/T612C/T772A/ A774T/A976T/A977G/T978C | |
| AHB1 65 | protein: | T187I/M285L/M321I/N326C/I406L/R426C | 42.51 |
| | gene: | C560T/G561T/A853C/G963T/A976T/A977G/T978C/A1216T/ T1218G/C1276T/T1278C | |
| AHB1 66 | protein: | D20V/L156F/T187I/M285L/M321I/K324I/N326C/R426C | 17.90 |
| | gene: | A59T/C60G/A468T/C560T/G561T/A853C/G963T/A971T/ A972T/A976T/A977G/T978C/C1276T/T1278C | |
| AHB1 67 | protein: | D20V/T187I/M285L/M321I/K324I/N326C/K389I | 14.86 |
| | gene: | A59T/C60G/C560T/G561T/A853C/G963T/A971T/A972T/ A976T/A977G/T978C/A1166T/A1167C | |
| AHB1 68 | protein: | L156F/T164I/T187I/L258I/K324I/N326C/K389I | 15.42 |
| | gene: | A468T/C491T/A492T/C560T/G561T/T772A/A774T/A971T/ A972T/A976T/A977G/T978C/A1166T/A1167C | |
| AHB1 69 | protein: | T187I/M285L/N326C/K381R/I406L/R426C | 34.56 |
| | gene: | C560T/G561T/A853C/A976T/A977G/T978C/A1141C/A1142G/ A1143T/A1216T/T1218G/C1276T/T1278C | |
| AHB1 70 | protein: | V75E/Q89H/L156F/T164I/T187I/Y204C/N226I/M285L/ K324I/N326C | 35.63 |
| | gene: | T224A/A267T/A468T/C491T/A492T/C560T/G561T/A611G/ T612C/A677T/C678T/A853C/A971T/A972T/A976T/A977G/ T978C | |
| AHB1 71 | protein: | V75E/L156F/T164I/T187I/Y204C/M285L/N326C | 34.13 |
| | gene: | T224A/A468T/C491T/A492T/C560T/G561T/A611G/T612C/ A853C/A976T/A977G/T978C | |
| AHB1 72 | protein: | D20V/T187I/M285L/M321I/K324I/N326C/R426C | 33.60 |
| | gene: | A59T/C60G/C560T/G561T/A853C/G963T/A971T/A972T/ A976T/A977G/T978C/C1276T/T1278C | |
| AHB1 73 | protein: | T187I/Y204C/K324I/N326C/I406L/R426C | 15.43 |
| | gene: | C560T/G561T/A611G/T612C/A971T/A972T/A976T/A977G/ T978C/A1216T/T1218G/C1276T/T1278C | |
| AHB1 74 | protein: | V75E/Q89H/L156F/T187EY204C/N326C | 43.57 |
| | gene: | T224A/A267T/A468T/C560T/G561T/A611G/T612C/A976T/ A977G/T978C | |
| AHB1 75 | protein: | Q89H/T164I/T187I/M285L/M321I/K324I/N326C/K381R/ K389I/I406L/P456L | 13.09 |
| | gene: | A267T/C491T/A492T/C560T/G561T/A853C/G963T/A971T/ A972T/A976T/A977G/T978C/A1141C/A1142G/A1143T/ A1166T/A1167C/A1216T/T1218G/C1366T/C1367T/A1368G | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB1 76 | protein: | T164I/T187I/L258I/M285L/M321I/N326C/K381R/K389I/ I406L/P456L | 48.38 |
| | gene: | C491T/A492T/C560T/G561T/T772A/A774T/A853C/G963T/ A976T/A977G/T978C/A1141C/A1142G/A1143T/A1166T/ A1167C/A1216T/T1218G/C1366T/C1367T/A1368G | |
| AHB1 77 | protein: | T187I/L258I/N326C/I406L/R426C | 41.69 |
| | gene: | C560T/G561T/T772A/A774T/A976T/A977G/T978C/A1216T/ T1218G/C1276T/T1278C | |
| AHB1 78 | protein: | V75E/T164I/T187I/L258I/N326C/K381R/R426C | 44.62 |
| | gene: | T224A/C491T/A492T/C560T/G561T/T772A/A774T/A976T/ A977G/T978C/A1141C/A1142G/A1143T/C1276T/T1278C | |
| AHB1 79 | protein: | D20V/T187I/N226I/M285L/N326C/R426C | 52.03 |
| | gene: | A59T/C60G/C560T/G561T/A677T/C678T/A853C/A976T/ A977G/T978C/C1276T/T1278C | |
| AHB1 80 | protein: | V75E/Q89H/T164I/T187I/Y204C/L258I/N326C/I406L | 30.42 |
| | gene: | T224A/A267T/C491T/A492T/C560T/G561T/A611G/T612C/ T772A/A774T/A976T/A977G/T978C/A1216T/T1218G | |
| AHB1 81 | protein: | L156F/T187I/M321I/N326C/I406L | 34.17 |
| | gene: | A468T/C560T/G561T/G963T/A976T/A977G/T978C/A1216T/ T1218G | |
| AHB1 82 | protein: | V75E/Q89H/L156F/T164I/T187I/Y204C/L258I/M285L/ M321I/N326C/K389I | 51.41 |
| | gene: | T224A/A267T/A468T/C491T/A492T/C560T/G561T/A611G/ T612C/T772A/A774T/A853C/G963T/A976T/A977G/T978C/ A1166T/A1167C | |
| AHB1 83 | protein: | V75E/T164I/T187I/N226I/L258I/M285L/K324I/N326C/ K389I | 42.59 |
| | gene: | T224A/C491T/A492T/C560T/G561T/A677T/C678T/T772A/ A774T/A853C/A971T/A972T/A976T/A977G/T978C/A1166T/ A1167C | |
| AHB1 84 | protein: | V75E/T187I/M285L/K324I/N326C/R426C | 15.71 |
| | gene: | T224A/C560T/G561T/A853C/A971T/A972T/A976T/A977G/ T978C/C1276T/T1278C | |
| AHB1 85 | protein: | D20V/Q89H/T164I/T187I/N226I/L258I/M321I/K324I/N326C/ K381R/P456L | 24.71 |
| | gene: | A59T/C60G/A267T/C491T/A492T/C560T/G561T/A677T/ C678T/T772A/A774T/G963T/A971T/A972T/A976T/A977G/ T978C/A1141C/A1142G/A1143T/C1366T/C1367T/A1368G | |
| AHB1 86 | protein: | V75E/Q89H/T164I/T187I/Y204C/L258I/M321I/N326C | 33.23 |
| | gene: | T224A/A267T/C491T/A492T/C560T/G561T/A611G/T612C/ T772A/A774T/G963T/A976T/A977G/T978C | |
| AHB1 87 | protein: | Q89H/L156F/T164I/T187I/Y204C/N226I/L258I/M285L/ N326C/K389I | 40.29 |
| | gene: | A267T/A468T/C491T/A492T/C560T/G561T/A611G/T612C/ A677T/C678T/T772A/A774T/A853C/A976T/A977G/T978C/ A1166T/A1167C | |
| AHB1 88 | protein: | Q89H/L156F/T187I/Y204C/N226I/M321I/K324I/N326C/ K381R/I406L | 25.52 |
| | gene: | A267T/A468T/C560T/G561T/A611G/T612C/A677T/C678T/ G963T/A971T/A972T/A976T/A977G/T978C/A1141C/ A1142G/A1143T/A1216T/T1218G | |
| AHB1 89 | protein: | L156F/T187I/M285L/N326C/R426C | 32.17 |
| | gene: | A468T/C560T/G561T/A853C/A976T/A977G/T978C/C1276T/ T1278C | |
| AHB1 90 | protein: | T187I/N226I/M285L/M321I/N326C/K381R/K389I/I406L/ R426C/P456L | 10.02 |
| | gene: | C560T/G561T/A677T/C678T/A853C/G963T/A976T/A977G/ T978C/A1141C/A1142G/A1143T/A1166T/A1167C/A1216T/ T1218G/C1276T/T1278C/C1366T/C1367T/A1368G | |
| AHB1 91 | protein: | Q89H/T187I/N326C/R426C/P456L | 19.01 |
| | gene: | A267T/C560T/G561T/A976T/A977G/T978C/C1276T/T1278C/ C1366T/C1367T/A1368G | |
| AHB1 92 | protein: | Q89H/T187I/Y204C/K324I/N326C/K389I/I406L/R426C | 36.57 |
| | gene: | A267T/C560T/G561T/A611G/T612C/A971T/A972T/A976T/ A977G/T978C/A1166T/A1167C/A1216T/T1218G/C1276T/ T1278C | |

TABLE 1-continued

Aspartase variant protein, gene mutation sites and the relative results
of the catalytic activity of the ammoniation of acrylic acid

| Variants | | substitutions | relative activity Variants/WT |
|---|---|---|---|
| WT | — | — | WT |
| AHB193 | protein: | D20V/Q89H/T164I/T187I/N226I/M285L/M321I/N326C/K381R/P456L | 11.61 |
| | gene: | A59T/C60G/A267T/C491T/A492T/C560T/G561T/A677T/C678T/A853C/G963T/A976T/A977G/T978C/A1141C/A1142G/A1143T/C1366T/C1367T/A1368G | |
| AHB194 | protein: | V75E/L156F/T187I/Y204C/L258I/M321I/K324I/N326C/K381R/I406L/R426C | 37.01 |
| | gene: | T224A/A468T/C560T/G561T/A611G/T612C/T772A/A774T/G963T/A971T/A972T/A976T/A977G/T978C/A1141C/A1142G/A1143T/A1216T/T1218G/C1276T/T1278C | |
| AHB195 | protein: | D20V/T187I/N226I/N326C/K381R | 12.80 |
| | gene: | A59T/C60G/C560T/G561T/A677T/C678T/A976T/A977G/T978C/A1141C/A1142G/A1143T | |
| AHB196 | protein: | D20 V/L156F/T187I/M285L/K324I/N326C/K381R/K389I | 37.25 |
| | gene: | A59T/C60G/A468T/C560T/G561T/A853C/A971T/A972T/A976T/A977G/T978C/A1141C/A1142G/A1143T/A1166T/A1167C | |
| AHB197 | protein: | Q89H/L156F/T164I/T187I/Y204C/M285L/K324I/N326C/K381R | 22.56 |
| | gene: | A267T/A468T/C491T/A492T/C560T/G561T/A611G/T612C/A853C/A971T/A972T/A976T/A977G/T978C/A1141C/A1142G/A1143T | |
| AHB198 | protein: | V75E/L156F/T187I/N326C/K389I/R426C | 47.60 |
| | gene: | T224A/A468T/C560T/G561T/A976T/A977G/T978C/A1166T/A1167C/C1276T/T1278C | |
| AHB199 | protein: | T187I/Y204C/N226I/N326C/K381R | 24.39 |
| | gene: | C560T/G561T/A611G/T612C/A677T/C678T/A976T/A977G/T978C/A1141C/A1142G/A1143T | |
| AHB200 | protein: | T187I/Y204C/L258I/M285L/M321I/K324I/N326C/K381R/I406L/R426C | 31.79 |
| | gene: | C560T/G561T/A611G/T612C/T772A/A774T/A853C/G963T/A971T/A972T/A976T/A977G/T978C/A1141C/A1142G/A1143T/A1216T/T1218G/C1276T/T1278C | |
| AHB201 | protein: | T187I/L258I/K324I/N326C/K389I/I406L | 22.84 |
| | gene: | C560T/G561T/T772A/A774T/A971T/A972T/A976T/A977G/T978C/A1166T/A1167C/A1216T/T1218G | |
| AHB202 | protein: | T187I/M321I/K324I/N326C/K381R | 16.67 |
| | gene: | C560T/G561T/G963T/A971T/A972T/A976T/A977G/T978C/A1141C/A1142G/A1143T | |
| AHB203 | protein: | V75E/Q89H/T164I/T187I/Y204C/N326C/K389I | 53.92 |
| | gene: | T224A/A267T/C491T/A492T/C560T/G561T/A611G/T612C/A976T/A977G/T978C/A1166T/A1167C | |
| AHB204 | protein: | V75E/Q89H/T187I/N226I/N326C/K389I | 30.13 |
| | gene: | T224A/A267T/C560T/G561T/A677T/C678T/A976T/A977G/T978C/A1166T/A1167C | |
| AHB205 | protein: | T187I/Y204C/M285L/N326C/P456L | 35.97 |
| | gene: | C560T/G561T/A611G/T612C/A853C/A976T/A977G/T978C/C1366T/C1367T/A1368G | |
| AHB206 | protein: | L156F/T187I/Y204C/K324I/N326C/K381R/R426C | 19.71 |
| | gene: | A468T/C560T/G561T/A611G/T612C/A971T/A972T/A976T/A977G/T978C/A1141C/A1142G/A1143T/C1276T/T1278C | |
| AHB207 | protein: | Q89H/T164I/T187I/M321I/N326C/I406L | 36.98 |
| | gene: | A267T/C491T/A492T/C560T/G561T/G963T/A976T/A977G/T978C/A1216T/T1218G | |
| AHB208 | protein: | T164I/T187I/L156F/K324I/N326C | 26.84 |
| | gene: | C491T/A492T/C560T/G561T/A468T/A971T/A972T/A976T/A977G/T978C | |
| AHB209 | protein: | D20V/V75E/T187I/N226I/M321I/K324I/N326C | 19.99 |
| | gene: | A59T/C60G/T224A/C560T/G561T/A677T/C678T/G963T/A971T/A972T/A976T/A977G/T978C | |
| AHB210 | protein: | T187I/K324I/N326C/I406L/R426C/P456L | 17.98 |
| | gene: | C560T/G561T/A971T/A972T/A976T/A977G/T978C/A1216T/T1218G/C1276T/T1278C/C1366T/C1367T/A1368G | |
| AHB211 | protein: | T164I/T187I/K324I/N326C/R426C | 43.42 |
| | gene: | C491T/A492T/C560T/G561T/A971T/A972T/A976T/A977G/T978C/C1276T/T1278C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB2 12 | protein: | T164I/T187I/L258I/M285L/M321I/K324I/N326C/K381R/K389I/P456L | 40.53 |
| | gene: | C491T/A492T/C560T/G561T/T772A/A774T/A853C/G963T/A971T/A972T/A976T/A977G/T978C/A1141C/A1142G/A1143T/A1166T/A1167C/C1366T/C1367T/A1368G | |
| AHB2 13 | protein: | Q89H/T164I/T187I/Y204C/N226I/L258I/M321I/N326C/R426C | 43.62 |
| | gene: | A267T/C491T/A492T/C560T/G561T/A611G/T612C/A677T/C678T/T772A/A774T/G963T/A976T/A977G/T978C/C1276T/T1278C | |
| AHB2 14 | protein: | Q89H/T187I/N226I/M321I/N326C | 33.19 |
| | gene: | A267T/C560T/G561T/A677T/C678T/G963T/A976T/A977G/T978C | |
| AHB2 15 | protein: | Q89H/L156F/T187I/Y204C/N326C/K381R/I406L/R426C/P456L | 17.80 |
| | gene: | A267T/A468T/C560T/G561T/A611G/T612C/A976T/A977G/T978C/A1141C/A1142G/A1143T/A1216T/T1218G/C1276T/T1278C/C1366T/C1367T/A1368G | |
| AHB2 16 | protein: | D20V/T187I/M321I/K324I/N326C/K381R/I406L/R426C | 23.32 |
| | gene: | A59T/C60G/C560T/G561T/G963T/A971T/A972T/A976T/A977G/T978C/A1141C/A1142G/A1143T/A1216T/T1218G/C1276T/T1278C | |
| AHB2 17 | protein: | T187I/N226I/L258I/N326C/I406L/P456L | 37.34 |
| | gene: | C560T/G561T/A677T/C678T/T772A/A774T/A976T/A977G/T978C/A1216T/T1218G/C1366T/C1367T/A1368G | |
| AHB2 18 | protein: | L156F/T187I/L258I/M321I/N326C | 39.18 |
| | gene: | A468T/C560T/G561T/T772A/A774T/G963T/A976T/A977G/T978C | |
| AHB2 19 | protein: | T164I/T187I/Y204C/N226I/L258I/M321I/N326C/K381R/K389I/I406L/P456L | 10.89 |
| | gene: | C491T/A492T/C560T/G561T/A611G/T612C/A677T/C678T/T772A/A774T/G963T/A976T/A977G/T978C/A1141C/A1142G/A1143T/A1166T/A1167C/A1216T/T1218G/C1366T/C1367T/A1368G | |
| AHB2 20 | protein: | D20V/L156F/T187I/N226I/N326C | 10.50 |
| | gene: | A59T/C60G/A468T/C560T/G561T/A677T/C678T/A976T/A977G/T978C | |
| AHB2 21 | protein: | V75E/Q89H/L156F/T187I/N226I/M321I/K324I/N326C/R426C | 43.86 |
| | gene: | T224A/A267T/A468T/C560T/G561T/A677T/C678T/G963T/A971T/A972T/A976T/A977G/T978C/C1276T/T1278C | |
| AHB2 22 | protein: | D20V/T187I/Y204C/N226I/K324I/N326C/K381R/R426C | 31.14 |
| | gene: | A59T/C60G/C560T/G561T/A611G/T612C/A677T/C678T/A971T/A972T/A976T/A977G/T978C/A1141C/A1142G/A1143T/C1276T/T1278C | |
| AHB2 23 | protein: | Q89H/T164I/T187I/Y204C/L258I/M321I/K324I/N326C/K389I/I406L/R426C | 43.83 |
| | gene: | A267T/C491T/A492T/C560T/G561T/A611G/T612C/T772A/A774T/G963T/A971T/A972T/A976T/A977G/T978C/A1166T/A1167C/A1216T/T1218G/C1276T/T1278C | |
| AHB2 24 | protein: | D20V/L156F/T187I/M285L/N326C | 34.58 |
| | gene: | A59T/C60G/A468T/C560T/G561T/A853C/A976T/A977G/T978C | |
| AHB2 25 | protein: | V75E/T187I/Y204C/N226I/K324I/N326C/K381R/I406L | 15.40 |
| | gene: | T224A/C560T/G561T/A611G/T612C/A677T/C678T/A971T/A972T/A976T/A977G/T978C/A1141C/A1142G/A1143T/A1216T/T1218G | |
| AHB2 26 | protein: | V75E/T187I/M321I/I406L/N326C/R426C | 46.83 |
| | gene: | T224A/C560T/G561T/G963T/A1216T/T1218G/A976T/A977G/T978C/C1276T/T1278C | |
| AHB2 27 | protein: | Q89H/T187I/L258I/N326C/R426C | 24.10 |
| | gene: | A267T/C560T/G561T/T772A/A774T/A976T/A977G/T978C/C1276T/T1278C | |
| AHB2 28 | protein: | V75E/Q89H/L156F/T164FT187I/Y204C/M285L/M321I/N326C/K389I | 40.78 |
| | gene: | T224A/A267T/A468T/C491T/A492T/C560T/G561T/A611G/T612C/A853C/G963T/A976T/A977G/T978C/A1166T/A1167C | |
| AHB2 29 | protein: | L156F/T187I/Y204C/N226I/M285L/K324I/N326C/K389I/R426C/P456L | 13.16 |
| | gene: | A468T/C560T/G561T/A611G/T612C/A677T/C678T/A853C/A971T/A972T/A976T/A977G/T978C/A1166T/A1167C/C1276T/T1278C/C1366T/C1367T/A1368G | |

TABLE 1-continued

Aspartase variant protein, gene mutation sites and the relative results of the catalytic activity of the ammoniation of acrylic acid

| Variants | | substitutions | relative activity Variants/ WT |
|---|---|---|---|
| WT | — | — | WT |
| AHB2 30 | protein: | T187I/N226I/M285L/N326C/R426C | 50.93 |
| | gene: | C560T/G561T/A677T/C678T/A853C/A976T/A977G/T978C/ C1276T/T1278C | |
| AHB2 31 | protein: | V75E/Q89H/T164I/T187I/L258I/M285L/M321I/N326C/ K389I/R426C | 25.23 |
| | gene: | T224A/A267T/C491T/A492T/C560T/G561T/T772A/A774T/ A853C/G963T/A976T/A977G/T978C/A1166T/A1167C/ C1276T/T1278C | |
| AHB2 32 | protein: | D20V/T187I/L258I/M321I/N326C/R426C | 28.21 |
| | gene: | A59T/C60G/C560T/G561T/T772A/A774T/G963T/A976T/ A977G/T978C/C1276T/T1278C | |
| AHB2 33 | protein: | D20V/L156F/T187I/Y204C/N226I/L258I/K324I/N326C/ K381R/R426C | 21.56 |
| | gene: | A59T/C60G/A468T/C560T/G561T/A611G/T612C/A677T/ C678T/T772A/A774T/A971T/A972T/A976T/A977G/T978C/ A1141C/A1142G/A1143T/C1276T/T1278C | |
| AHB2 34 | protein: | D20V/L156F/T187I/Y204C/K324I/N326C | 39.25 |
| | gene: | A59T/C60G/A468T/C560T/G561T/A611G/T612C/A971T/ A972T/A976T/A977G/T978C | |
| AHB2 35 | protein: | V75E/Q89H/T187I/N326C/K389I/R426C | 13.50 |
| | gene: | T224A/A267T/C560T/G561T/A976T/A977G/T978C/A1166T/ A1167C/C1276T/T1278C | |
| AHB2 36 | protein: | T164I/T187I/Y204C/L258I/M321I/K324I/N326C/K389I | 24.76 |
| | gene: | C491T/A492T/C560T/G561T/A611G/T612C/T772A/A774T/ G963T/A971T/A972T/A976T/A977G/T978C/A1166T/A1167C | |
| AHB2 37 | protein: | D20V/T164I/T187I/M285L/N326C | 15.38 |
| | gene: | A59T/C60G/C491T/A492T/C560T/G561T/A853C/A976T/ A977G/T978C | |
| AHB2 38 | protein: | T164I/T187I/Y204C/N226I/K324I/N326C/K389I/I406L | 28.69 |
| | gene: | C491T/A492T/C560T/G561T/A611G/T612C/A677T/C678T/ A971T/A972T/A976T/A977G/T978C/A1166T/A1167C/A1216T/ T1218G | |
| AHB2 39 | protein: | T187I/L258I/M285L/M321I/K324I/N326C/K381R/I406L | 12.32 |
| | gene: | C560T/G561T/T772A/A774T/A853C/G963T/A971T/A972T/ A976T/A977G/T978C/A1141C/A1142G/A1143T/A1216T/ T1218G | |
| AHB2 40 | protein: | T187I/Y204C/N226I/L258I/M321I/N326C/I406L | 32.95 |
| | gene: | C560T/G561T/A611G/T612C/A677T/C678T/T772A/A774T/ G963T/A976T/A977G/T978C/A1216T/T1218G | |
| AHB2 41 | protein: | V75E/T187I/N226I/N326C/K381R | 11.20 |
| | gene: | T224A/C560T/G561T/A677T/C678T/A976T/A977G/T978C/ A1141C/A1142G/A1143T | |
| AHB2 42 | protein: | V75E/T187I/Y204C/N326C/I406L | 22.36 |
| | gene: | T224A/C560T/G561T/A611G/T612C/A976T/A977G/T978C/ A1216T/T1218G | |
| AHB2 43 | protein: | V75E/T187I/Y204C/N226I/M285L/K324I/N326C/K381R/ R426C | 31.88 |
| | gene: | T224A/C560T/G561T/A611G/T612C/A677T/C678T/A853C/ A971T/A972T/A976T/A977G/T978C/A1141C/A1142G/ A1143C/C1276T/T1278C | |
| AHB2 44 | protein: | Q89H/T187I/M285L/N326C/R426C | 15.97 |
| | gene: | A267T/C560T/G561T/A853C/A976T/A977G/T978C/C1276T/ T1278C | |
| AHB2 45 | protein: | Q89H/T187I/K324I/N326C/K389I | 50.05 |
| | gene: | A267T/C560T/G561T/A971T/A972T/A976T/A977G/T978C/ A1166T/A1167C | |
| AHB2 46 | protein: | Q89H/T164I/T187I/K324I/N326C/K389I | 17.15 |
| | gene: | A267T/C491T/A492T/C560T/G561T/A971T/A972T/A976T/ A977G/T978C/A1166T/A1167C | |
| AHB2 47 | protein: | L156F/T187I/Y204C/L25 8I/M285L/M321I/N326C/K381R/K389I | 46.09 |
| | gene: | A468T/C560T/G561T/A611G/T612C/T772A/A774T/A853C/ G963T/A976T/A977G/T978C/A1141C/A1142G/A1143T/ A1166T/A1167C | |
| AHB2 48 | protein: | T187I/K324I/N326C/K381R/K389I/I406L | 27.96 |
| | gene: | C560T/G561T/A971T/A972T/A976T/A977G/T978C/A1141C/ A1142G/A1143T/A1166T/A1167C/A1216T/T1218G | |
| AHB2 49 | protein: | V75E/Q89H/T164I/T187VY204C/M285L/N326C/K389I/ R426C | 52.79 |
| | gene: | T224A/A267T/C491T/A492T/C560T/G561T/A611G/T612C/ A853C/A976T/A977G/T978C/A1166T/A1167C/C1276T/T1278C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB2 50 | protein: | V75E/T187I/Y204C/N226I/L258I/N326C/I406L | 46.36 |
| | gene: | T224A/C560T/G561T/A611G/T612C/A677T/C678T/T772A/A774T/A976T/A977G/T978C/A1216T/T1218G | |
| AHB2 51 | protein: | T187I/Y204C/N226I/K324I/N326C/R426C | 41.42 |
| | gene: | C560T/G561T/A611G/T612C/A677T/C678T/A971T/A972T/A976T/A977G/T978C/C1276T/T1278C | |
| AHB2 52 | protein: | V75E/Q89H/L156F/T164I/T187I/M285L/N326C/K381R/K389I/R426C | 31.37 |
| | gene: | T224A/A267T/A468T/C491T/A492T/C560T/G561T/A853C/A976T/A977G/T978C/A1141C/A1142G/A1143T/A1166T/A1167C/C1276T/T1278C | |
| AHB2 53 | protein: | D20V/L156F/T187I/M321I/N326C/I406L/R426C | 17.17 |
| | gene: | A59T/C60G/A468T/C560T/G561T/G963T/A976T/A977G/T978C/A1216T/T1218G/C1276T/T1278C | |
| AHB2 54 | protein: | D20V/T187I/Y204C/N226I/M285L/K324I/N326C/R426C | 18.13 |
| | gene: | A59T/C60G/C560T/G561T/A611G/T612C/A677T/C678T/A853C/A971T/A972T/A976T/A977G/T978C/C1276T/T1278C | |
| AHB2 55 | protein: | T164I/T187I/N226I/L258I/M285L/M321I/N326C/K381R/R426C | 40.54 |
| | gene: | C491T/A492T/C560T/G561T/A677T/C678T/T772A/A774T/A853C/G963T/A976T/A977G/T978C/A1141C/A1142G/A1143T/C1276T/T1278C | |
| AHB2 56 | protein: | V75E/Q89H/L156F/T187I/N226I/M285L/N326C/K381R/K389I | 27.05 |
| | gene: | T224A/A267T/A468T/C560T/G561T/A677T/C678T/A853C/A976T/A977G/T978C/A1141C/A1142G/A1143T/A1166T/A1167C | |
| AHB2 57 | protein: | D20V/T187I/N226I/M285L/K324I/N326C/K381R/R426C | 26.95 |
| | gene: | A59T/C60G/C560T/G561T/A677T/C678T/A853C/A971T/A972T/A976T/A977G/T978C/A1141C/A1142G/A1143T/C1276T/T1278C | |
| AHB2 58 | protein: | T187I/Y204C/M321I/N326C/K381R | 26.92 |
| | gene: | C560T/G561T/A611G/T612C/G963T/A976T/A977G/T978C/A1141C/A1142G/A1143T | |
| AHB2 59 | protein: | V75E/T164I/T187I/N226I/L258I/N326C/K389I | 45.00 |
| | gene: | T224A/C491T/A492T/C560T/G561T/A677T/C678T/T772A/A774T/A976T/A977G/T978C/A1166T/A1167C | |
| AHB2 60 | protein: | D20V/L156F/T164I/T187I/L258I/N326C/K381R/K389I/I406L/R426C | 40.38 |
| | gene: | A59T/C60G/A468T/C491T/A492T/C560T/G561T/T772A/A774T/A976T/A977G/T978C/A1141C/A1142G/A1143T/A1166T/A1167C/A1216T/T1218G/C1276T/T1278C | |
| AHB2 61 | protein: | D20V/V75E/Q89H/L156F/T164I/T187I/L258I/N326C/K381R/K389I/I406L | 38.67 |
| | gene: | A59T/C60G/T224A/A267T/A468T/C491T/A492T/C560T/G561T/T772A/A774T/A976T/A977G/T978C/A1141C/A1142G/A1143T/A1166T/A1167C/A1216T/T1218G | |
| AHB2 62 | protein: | T187I/N226I/N326C/K381R/I406L/R426C | 46.09 |
| | gene: | C560T/G561T/A677T/C678T/A976T/A977G/T978C/A1141C/A1142G/A1143T/A1216T/T1218G/C1276T/T1278C | |
| AHB2 63 | protein: | Q89H/T187I/Y204C/N326C/I406L | 16.60 |
| | gene: | A267T/C560T/G561T/A611G/T612C/A976T/A977G/T978C/A1216T/T1218G | |
| AHB2 64 | protein: | D20V/L156F/T164I/T187I/Y204C/N226I/M321I/K324I/N326C/K389I/R426C | 37.96 |
| | gene: | A59T/C60G/A468T/C491T/A492T/C560T/G561T/A611G/T612C/A677T/C678T/G963T/A971T/A972T/A976T/A977G/T978C/A1166T/A1167C/C1276T/T1278C | |
| AHB2 65 | protein: | D20V/T164I/T187I/L258I/K324I/N326C/K381R/I406L | 10.91 |
| | gene: | A59T/C60G/C491T/A492T/C560T/G561T/T772A/A774T/A971T/A972T/A976T/A977G/T978C/A1141C/A1142G/A1143T/A1216T/T1218G | |
| AHB2 66 | protein: | V75E/T164I/T187I/M321I/K324I/N326C/K389I/R426C/P456L | 46.29 |
| | gene: | T224A/C491T/A492T/C560T/G561T/G963T/A971T/A972T/A976T/A977G/T978C/A1166T/A1167C/C1276T/T1278C/C1366T/C1367T/A1368G | |
| AHB2 67 | protein: | Q89H/T187I/Y204C/N226I/N326C/K389I | 16.72 |
| | gene: | A267T/C560T/G561T/A611G/T612C/A677T/C678T/A976T/A977G/T978C/A1166T/A1167C | |

TABLE 1-continued

Aspartase variant protein, gene mutation sites and the relative results
of the catalytic activity of the ammoniation of acrylic acid

| Variants | | substitutions | relative activity Variants/ WT |
|---|---|---|---|
| WT | — | — | WT |
| AHB2 68 | protein: | L156F/T187I/M321I/N326C/K389I/R426C | 38.04 |
| | gene: | A468T/C560T/G561T/G963T/A976T/A977G/T978C/A1166T/ A1167C/C1276T/T1278C | |
| AHB2 69 | protein: | Q89H/L156F/T187I/N226I/L258I/M285L/N326C/K389I/ I406L/R426C | 18.33 |
| | gene: | A267T/A468T/C560T/G561T/A677T/C678T/T772A/A774T/ A853C/A976T/A977G/T978C/A1166T/A1167C/A1216T/ T1218G/C1276T/T1278C | |
| AHB2 70 | protein: | Q89H/L156F/T187I/Y204C/M285L/M321I/N326C/R426C/ P456L | 44.17 |
| | gene: | A267T/A468T/C560T/G561T/A611G/T612C/A853C/G963T/ A976T/A977G/T978C/C1276T/T1278C/C1366T/C1367T/ A1368G | |
| AHB2 71 | protein: | Q89H/L156F/T187I/N226FK324I/N326C/K389I/I406L/R426C | 14.39 |
| | gene: | A267T/A468T/C560T/G561T/A677T/C678T/A971T/A972T/ A976T/A977G/T978C/A1166T/A1167C/A1216T/T1218G/ C1276T/T1278C | |
| AHB2 72 | protein: | T164I/T187I/N226I/N326C/K381R | 24.88 |
| | gene: | C491T/A492T/C560T/G561T/A677T/C678T/A976T/A977G/ T978C/A1141C/A1142G/A1143T | |
| AHB2 73 | protein: | V75E/Q89H/T187I/Y204C/N226I/L258I/K324I/N326C/K381R | 31.25 |
| | gene: | T224A/A267T/C560T/G561T/A611G/T612C/A677T/C678T/ T772A/A774T/A971T/A972T/A976T/A977G/T978C/A1141C/ A1142G/A1143T | |
| AHB2 74 | protein: | Q89H/T164I/T187I/Y204C/M321FK324I/N326C/K381R/ I406L/R426C | 45.22 |
| | gene: | A267T/C491T/A492T/C560T/G561T/A611G/T612C/G963T/ A971T/A972T/A976T/A977G/T978C/A1141C/A1142G/ A1143T/A1216T/T1218G/C1276T/T1278C | |
| AHB2 75 | protein: | D20V/V75E/Q89H/T164I/T187I/M285L/M321I/K324I/N326C/ K381R | 28.25 |
| | gene: | A59T/C60G/T224A/A267T/C491T/A492T/C560T/G561T/ A853C/G963T/A971T/A972T/A976T/A977G/T978C/A1141C/ A1142G/A1143T | |
| AHB2 76 | protein: | D20V/T187I/N326C/K381R/R426C | 39.81 |
| | gene: | A59T/C60G/C560T/G561T/A976T/A977G/T978C/A1141C/ A1142G/A1143T/C1276T/T1278C | |
| AHB2 77 | protein: | T187I/K324I/N326C/K389I/R426C | 40.72 |
| | gene: | C560T/G561T/A971T/A972T/A976T/A977G/T978C/A1166T/ A1167C/C1276T/T1278C | |
| AHB2 78 | protein: | Q89H/T187I/L258I/M285L/N326C/K389I/I406L | 21.71 |
| | gene: | A267T/C560T/G561T/T772A/A774T/A853C/A976T/A977G/ T978C/A1166T/A1167C/A1216T/T1218G | |
| AHB2 79 | protein: | D20V/T187I/M321I/N326C/I406L | 30.39 |
| | gene: | A59T/C60G/C560T/G561T/G963T/A976T/A977G/T978C/ A1216T/T1218G | |
| AHB2 80 | protein: | V75E/Q89H/T187I/L258I/M321I/N326C/I406L/R426C | 25.67 |
| | gene: | T224A/A267T/C560T/G561T/T772A/A774T/G963T/A976T/ A977G/T978C/A1216T/T1218G/C1276T/T1278C | |
| AHB2 81 | protein: | T187I/N226I/L258I/M321I/N326C/R426C | 23.08 |
| | gene: | C560T/G561T/A677T/C678T/T772A/A774T/G963T/A976T/ A977G/T978C/C1276T/T1278C | |
| AHB2 82 | protein: | T164I/T187I/Y204C/N226I/L258I/M321I/K324I/N326C/ K381R/R426C | 45.52 |
| | gene: | C491T/A492T/C560T/G561T/A611G/T612C/A677T/C678T/ T772A/A774T/G963T/A971T/A972T/A976T/A977G/T978C/ A1141C/A1142G/A1143T/C1276T/T1278C | |
| AHB2 83 | protein: | L156F/T164I/T187I/Y204C/N326C/K381R/R426C | 37.98 |
| | gene: | A468T/C491T/A492T/C560T/G561T/A611G/T612C/ A976T/A977G/T978C/A1141C/A1142G/A1143T/C1276T/T1278C | |
| AHB2 84 | protein: | T187I/N226I/M285L/K324I/N326C/R426C | 48.04 |
| | gene: | C560T/G561T/A677T/C678T/A853C/A971T/A972T/A976T/ A977G/T978C/C1276T/T1278C | |
| AHB2 85 | protein: | D20V/T187I/Y204C/N226I/M321I/N326C/I406L/R426C | 37.40 |
| | gene: | A59T/C60G/C560T/G561T/A611G/T612C/A677T/C678T/ G963T/A976T/A977G/T978C/A1216T/T1218G/C1276T/T1278C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB2 86 | protein: | Q89H/L156F/T187I/Y204C/N226I/L258I/M285L/M321I/K324I/N326C | 34.96 |
| | gene: | A267T/A468T/C560T/G561T/A611G/T612C/A677T/C678T/T772A/A774T/A853C/G963T/A971T/A972T/A976T/A977G/T978C | |
| AHB2 87 | protein: | V75E/L156F/T164I/T187I/L258I/N326C | 32.41 |
| | gene: | T224A/A468T/C491T/A492T/C560T/G561T/T772A/A774T/A976T/A977G/T978C | |
| AHB2 88 | protein: | D20V/V75E/T164I/T187I/Y204C/N326C | 19.27 |
| | gene: | A59T/C60G/T224A/C491T/A492T/C560T/G561T/A611G/T612C/A976T/A977G/T978C | |
| AHB2 89 | protein: | D20V/T187I/Y204C/K324I/N326C | 26.57 |
| | gene: | A59T/C60G/C5 60T/G561T/A611G/T612C/A971T/A972T/A976T/A977G/T978C | |
| AHB2 90 | protein: | L156F/T187I/Y204C/N326C/K381R/R426C | 23.85 |
| | gene: | A468T/C560T/G561T/A611G/T612C/A976T/A977G/T978C/A1141C/A1142G/A1143T/C1276T/T1278C | |
| AHB2 91 | protein: | V75E/Q89H/T164I/T187I/N326C | 41.43 |
| | gene: | T224A/A267T/C491T/A492T/C560T/G561T/A976T/A977G/T978C | |
| AHB2 92 | protein: | D20V/T164I/T187I/N226I/K324I/N326C | 17.12 |
| | gene: | A59T/C60G/C491T/A492T/C560T/G561T/A677T/C678T/A971T/A972T/A976T/A977G/T978C | |
| AHB2 93 | protein: | T187I/N226I/L258I/M285L/M321I/K324I/N326C | 35.48 |
| | gene: | C560T/G561T/A677T/C678T/T772A/A774T/A853C/G963T/A971T/A972T/A976T/A977G/T978C | |
| AHB2 94 | protein: | T187I/N226I/L258I/N326C/P456L | 31.00 |
| | gene: | C560T/G561T/A677T/C678T/T772A/A774T/A976T/A977G/T978C/C1366T/C1367T/A1368G | |
| AHB2 95 | protein: | T64I/T187I/N226I/K324I/N326C/K389I/P456L | 53.54 |
| | gene: | C491T/A492T/C560T/G561T/A677T/C678T/A971T/A972T/A976T/A977G/T978C/A1166T/A1167C/C1366T/C1367T/A1368G | |
| AHB2 96 | protein: | D20V/T187I/Y204C/L258I/M285L/M321I/K324I/N326C/K389I/R426C | 13.89 |
| | gene: | A59T/C60G/C560T/G561T/A611G/T612C/T772A/A774T/A853C/G963T/A971T/A972T/A976T/A977G/T978C/A1166T/A1167C/C1276T/T1278C | |
| AHB2 97 | protein: | V75E/L156F/T187I/Y204C/L258I/M321I/N326C/K381R/I406L/R426C | 23.26 |
| | gene: | T224A/A468T/C560T/G561T/A611G/T612C/T772A/A774T/G963T/A976T/A977G/T978C/A1141C/A1142G/A1143T/A1216T/T1218G/C1276T/T1278C | |
| AHB2 98 | protein: | T187I/Y204C/N226I/L258I/M321I/K324I/N326C/K381R/K389I/P456L | 28.70 |
| | gene: | C560T/G561T/A611G/T612C/A677T/C678T/T772A/A774T/G963T/A971T/A972T/A976T/A977G/T978C/A1141C/A1142G/A1143T/A1166T/A1167C/C1366T/C1367T/A1368G | |
| AHB2 99 | protein: | T187I/N226I/M321I/K324I/N326C | 23.30 |
| | gene: | C560T/G561T/A677T/C678T/G963T/A971T/A972T/A976T/A977G/T978C | |
| AHB300 | protein: | V75E/T164I/T187I/N226I/L258I/M285L/N326C/K389I/I406L | 36.51 |
| | gene: | T224A/C491T/A492T/C560T/G561T/A677T/C678T/T772A/A774T/A853C/A976T/A977G/T978C/A1166T/A1167C/A1216T/T1218G | |
| AHB301 | protein: | V75E/T187I/M285L/M321I/K324I/N326C/R426C | 21.11 |
| | gene: | T224A/C560T/G561T/A853C/G963T/A971T/A972T/A976T/A977G/T978C/C1276T/T1278C | |
| AHB302 | protein: | V75E/T187I/L258I/M285L/N326C/K389I | 29.14 |
| | gene: | T224A/C560T/G561T/T772A/A774T/A853C/A976T/A977G/T978C/A1166T/A1167C | |
| AHB303 | protein: | T164I/T187I/M285L/N326C/K381R/R426C | 49.63 |
| | gene: | C491T/A492T/C560T/G561T/A853C/A976T/A977G/T978C/A1141C/A1142G/A1143T/C1276T/T1278C | |
| AHB304 | protein: | T164I/T187I/N326C/K381R/I406L | 38.86 |
| | gene: | C491T/A492T/C560T/G561T/A976T/A977G/T978C/A1141C/A1142G/A1143T/A1216T/T1218G | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB3 05 | protein: | T164I/T187I/M285L/N326C/K389I | 26.50 |
| | gene: | C491T/A492T/C560T/G561T/A853C/A976T/A977G/T978C/A1166T/A1167C | |
| AHB3 06 | protein: | D20V/L156F/T164I/T187I/L258I/M321I/N326C/K381R/K389I/I406L/R426C | 13.11 |
| | gene: | A59T/C60G/A468T/C491T/A492T/C560T/G561T/T772A/A774T/G963T/A976T/A977G/T978C/A1141C/A1142G/A1143T/A1166T/A1167C/A1216T/T1218G/C1276T/T1278C | |
| AHB3 07 | protein: | D20V/L156F/T187I/M321FK324I/N326C/K389I/R426C/P456L | 17.58 |
| | gene: | A59T/C60G/A468T/C560T/G561T/G963T/A971T/A972T/A976T/A977G/T978C/A1166T/A1167C/C1276T/T1278C/C1366T/C1367T/A1368G | |
| AHB3 08 | protein: | T187I/N226I/L258I/N326C/K381R/R426C | 25.20 |
| | gene: | C560T/G561T/A677T/C678T/T772A/A774T/A976T/A977G/T978C/A1141C/A1142G/A1143T/C1276T/T1278C | |
| AHB3 09 | protein: | T187I/N226I/M285L/N326C/K389I/R426C/P456L | 44.86 |
| | gene: | C560T/G561T/A677T/C678T/A853C/A976T/A977G/T978C/A1166T/A1167C/C1276T/T1278C/C1366T/C1367T/A1368G | |
| AHB3 10 | protein: | D20V/T164I/T187I/M321I/N326C/K381R/R426C | 13.36 |
| | gene: | A59T/C60G/C491T/A492T/C560T/G561T/G963T/A976T/A977G/T978C/A1141C/A1142G/A1143T/C1276T/T1278C | |
| AHB3 11 | protein: | T187I/M321I/N326C/K381R/K389I/R426C | 22.82 |
| | gene: | C560T/G561T/G963T/A976T/A977G/T978C/A1141C/A1142G/A1143T/A1166T/A1167C/C1276T/T1278C | |
| AHB3 12 | protein: | T164I/T187I/Y204C/N226I/L258I/M285L/K324I/N326C/K389I | 40.49 |
| | gene: | C491T/A492T/C560T/G561T/A611G/T612C/A677T/C678T/T772A/A774T/A853C/A971T/A972T/A976T/A977G/T978C/A1166T/A1167C | |
| AHB3 13 | protein: | Q89H/T187I/Y204C/N226I/N326C/K389I/I406L/R426C | 12.46 |
| | gene: | A267T/C560T/G561T/A611G/T612C/A677T/C678T/A976T/A977G/T978C/A1166T/A1167C/A1216T/T1218G/C1276T/T1278C | |
| AHB3 14 | protein: | V75E/L156F/T187I/N226I/K324I/N326C/I406L/R426C | 41.37 |
| | gene: | T224A/A468T/C560T/G561T/A677T/C678T/A971T/A972T/A976T/A977G/T978C/A1216T/T1218G/C1276T/T1278C | |
| AHB3 15 | protein: | Q89H/L156F/T187FY204C/M285L/M321I/N326C/K389I/I406L | 37.44 |
| | gene: | A267T/A468T/C560T/G561T/A611G/T612C/A853C/G963T/A976T/A977G/T978C/A1166T/A1167C/A1216T/T1218G | |
| AHB3 16 | protein: | Q89H/T187I/Y204C/N326C/P456L | 42.78 |
| | gene: | A267T/C560T/G561T/A611G/T612C/A976T/A977G/T978C/C1366T/C1367T/A1368G | |
| AHB3 17 | protein: | D20V/Q89H/L156F/T187I/L258I/M321I/N326C/K381R/P456L | 21.08 |
| | gene: | A59T/C60G/A267T/A468T/C560T/G561T/T772A/A774T/G963T/A976T/A977G/T978C/A1141C/A1142G/A1143T/C1366T/C1367T/A1368G | |
| AHB3 18 | protein: | L156F/T187I/Y204C/M321I/N326C/K389I/R426C | 31.34 |
| | gene: | A468T/C560T/G561T/A611G/T612C/G963T/A976T/A977G/T978C/A1166T/A1167C/C1276T/T1278C | |
| AHB3 19 | protein: | D20V/V75E/L156F/T187I/Y204C/M285L/N326C/K381R/K389I | 27.27 |
| | gene: | A59T/C60G/T224A/A468T/C560T/G561T/A611G/T612C/A853C/A976T/A977G/T978C/A1141C/A1142G/A1143T/A1166T/A1167C | |
| AHB3 20 | protein: | D20V/TI87I/L258I/1406L/N326C/R426C | 24.71 |
| | gene: | A59T/C60G/C560T/G561T/T772A/A774T/A1216T/T1218G/A976T/A977G/T978C/C1276T/T1278C | |
| AHB3 21 | protein: | D20V/V75E/L156F/T187I/M321I/K324I/N326C/R426C/P456L | 11.15 |
| | gene: | A59T/C60G/T224A/A468T/C560T/G561T/G963T/A971T/A972T/A976T/A977G/T978C/C1276T/T1278C/C1366T/C1367T/A1368G | |
| AHB3 22 | protein: | T164I/T187I/N226I/L258I/M285L/M321I/K324I/N326C/K381R/K389I/P456L | 19.45 |
| | gene: | C491T/A492T/C560T/G561T/A677T/C678T/T772A/A774T/A853C/G963T/A971T/A972T/A976T/A977G/T978C/A1141C/A1142G/A1143T/A1166T/A1167C/C1366T/C1367T/A1368G | |

TABLE 1-continued

Aspartase variant protein, gene mutation sites and the relative results of the catalytic activity of the ammoniation of acrylic acid

| Variants | | substitutions | relative activity Variants/ WT |
|---|---|---|---|
| WT | — | — | WT |
| AHB3 23 | protein: | V75E/L156F/T187I/M285L/M321I/N326C/I406L/R426C | 15.24 |
| | gene: | T224A/A468T/C560T/G561T/A853C/G963T/A976T/A977G/ T978C/A1216T/T1218G/C1276T/T1278C | |
| AHB3 24 | protein: | T164I/T187I/Y2O4C/N226I/L258I/M285L/M321I/K324I/ N326C/I406L | 34.32 |
| | gene: | C491T/A492T/C560T/G561T/A611G/T612C/A677T/C678T/ T772A/A774T/A853C/G963T/A971T/A972T/A976T/A977G/ T978C/A1216T/T1218G | |
| AHB3 25 | protein: | T187I/N326C/K381R/K389I/I406L/R426C | 27.33 |
| | gene: | C560T/G561T/A976T/A977G/T978C/A1141C/A1142G/ A1143T/A1166T/A1167C/A1216T/T1218G/C1276T/T1278C | |
| AHB3 26 | protein: | T164I/T187I/N226I/N326C/R426C | 27.55 |
| | gene: | C491T/A492T/C560T/G561T/A677T/C678T/A976T/A977G/ T978C/C1276T/T1278C | |
| AHB3 27 | protein: | V75E/T164I/T187I/N226I/M321I/N326C/K389I | 37.66 |
| | gene: | T224A/C491T/A492T/C560T/G561T/A677T/C678T/G963T/ A976T/A977G/T978C/A1166T/A1167C | |
| AHB3 28 | protein: | T187I/Y204C/N326C/R426C/P456L | 49.60 |
| | gene: | C560T/G561T/A611G/T612C/A976T/A977G/T978C/C1276T/ T1278C/C1366T/C1367T/A1368G | |
| AHB3 29 | protein: | V75E/Q89H/T187I/Y204C/K324I/N326C/I406L | 25.48 |
| | gene: | T224A/A267T/C560T/G561T/A611G/T612C/A971T/A972T/ A976T/A977G/T978C/A1216T/T1218G | |
| AHB3 30 | protein: | D20V/T187I/N226I/L258I/N326C/K389I/I406L | 19.42 |
| | gene: | A59T/C60G/C560T/G561T/A677T/C678T/T772A/A774T/ A976T/A977G/T978C/A1166T/A1167C/A1216T/T1218G | |
| AHB3 31 | protein: | D20V/T164I/T187I/M285L/M321I/K324I/N326C/I406L | 35.80 |
| | gene: | A59T/C60G/C491T/A492T/C560T/G561T/A853C/G963T/ A971T/A972T/A976T/A977G/T978C/A1216T/T1218G | |
| AHB3 32 | protein: | D20V/T187I/L258I/M321I/N326C/K381R/K389I/R426C | 37.14 |
| | gene: | A59T/C60G/C560T/G561T/T772A/A774T/G963T/A976T/ A977G/T978C/A1141C/A1142G/A1143T/A1166T/A1167C/ C1276T/T1278C | |
| AHB3 33 | protein: | V75E/L156F/T187I/L258I/K324I/N326C | 22.86 |
| | gene: | T224A/A468T/C560T/G561T/T772A/A774T/A971T/A972T/ A976T/A977G/T978C | |
| AHB3 34 | protein: | V75E/T164I/T187I/Y204C/L258I/M321I/N326C/K381R/ K389I/I406L | 31.73 |
| | gene: | T224A/C491T/A492T/C560T/G561T/A611G/T612C/T772A/ A774T/G963T/A976T/A977G/T978C/A1141C/A1142G/ A1143T/A1166T/A1167C/A1216T/T1218G | |
| AHB3 35 | protein: | D20V/V75E/Q89H/T164I/T187I/N226I/M285L/M321I/ N326C/K389I/I406L | 31.88 |
| | gene: | A59T/C60G/T224A/A267T/C491T/A492T/C560T/G561T/ A677T/C678T/A853C/G963T/A976T/A977G/T978C/A1166T/ A1167C/A1216T/T1218G | |
| AHB3 36 | protein: | V75E/Q89H/L156F/T164I/T187I/N226I/M321I/N326C/I406L | 14.39 |
| | gene: | T224A/A267T/A468T/C491T/A492T/C560T/G561T/A677T/ C678T/G963T/A976T/A977G/T978C/A1216T/T1218G | |
| AHB3 37 | protein: | D20V/T187I/N226I/L258I/N326C/I406L/R426C | 21.47 |
| | gene: | A59T/C60G/C560T/G561T/A677T/C678T/T772A/A774T/ A976T/A977G/T978C/A1216T/T1218G/C1276T/T1278C | |
| AHB3 38 | protein: | L156F/T187FY204C/K389I/N326C/R426C | 43.81 |
| | gene: | A468T/C560T/G561T/A611G/T612C/A1166T/A1167C/A976T/ A977G/T978C/C1276T/T1278C | |
| AHB3 39 | protein: | T187I/Y204C/L258I/M321I/N326C/R426C | 12.62 |
| | gene: | C560T/G561T/A611G/T612C/T772A/A774T/G963T/A976T/ A977G/C1276T/T1278C | |
| AHB3 40 | protein: | D20V/T187I/N326C/K389I/R426C | 23.80 |
| | gene: | A59T/C60G/C560T/G561T/A976T/A977G/T978C/A1166T/ A1167C/C1276T/T1278C | |
| AHB3 41 | protein: | T187I/L258I/M285L/N326C/R426C | 40.73 |
| | gene: | C560T/G561T/T772A/A774T/A853C/A976T/A977G/T978C/ C1276T/T1278C | |
| AHB3 42 | protein: | D20V/T164I/T187I/M285L/M321I/N326C/K381R/K389I/ I406L | 27.54 |
| | gene: | A59T/C60G/C491T/A492T/C560T/G561T/A853C/G963T/ A976T/A977G/T978C/A1141C/A1142G/A1143T/A1166T/ A1167C/A1216T/T1218G | |

TABLE 1-continued

Aspartase variant protein, gene mutation sites and the relative results of the catalytic activity of the ammoniation of acrylic acid

| Variants | | substitutions | relative activity Variants/ WT |
|---|---|---|---|
| WT | — | — | WT |
| AHB3 43 | protein: | Q89H/L156F/T164I/T187I/Y204C/M285L/M321I/N326C/ K389I/I406L | 39.32 |
| | gene: | A267T/A468T/C491T/A492T/C560T/G561T/A611G/T612C/ A853C/G963T/A976T/A977G/T978C/A1166T/A1167C/ A1216T/T1218G | |
| AHB3 44 | protein: | T187I/L258I/M285L/M321I/N326C/K381R | 12.88 |
| | gene: | C560T/G561T/T772A/A774T/A853C/G963T/A976T/A977G/ T978C/A1141C/A1142G/A1143T | |
| AHB3 45 | protein: | T187I/L258I/N326C/K381R/I406L/R426C | 21.82 |
| | gene: | C560T/G561T/T772A/A774T/A976T/A977G/T978C/A1141C/ A1142G/A1143T/A1216T/T1218G/C1276T/T1278C | |
| AHB3 46 | protein: | D20V/T164I/T187I/M321I/N326C | 15.96 |
| | gene: | A59T/C60G/C491T/A492T/C560T/G561T/G963T/A976T/ A977G/T978C | |
| AHB3 47 | protein: | Q89H/L156F/T164I/T187I/M285L/N326C/K389I/I406L/ R426C | 40.82 |
| | gene: | A267T/A468T/C491T/A492T/C560T/G561T/A853C/A976T/ A977G/T978C/A1166T/A1167C/A1216T/T1218G/C1276T/ T1278C | |
| AHB3 48 | protein: | V75E/L156F/T164I/T187I/M321I/N326C | 33.50 |
| | gene: | T224A/A468T/C491T/A492T/C560T/G561T/G963T/A976T/ A977G/T978C | |
| AHB3 49 | protein: | D20V/T187I/Y204C/N226I/N326C/K381R/I406L/R426C | 29.27 |
| | gene: | A59T/C60G/C560T/G561T/A611G/T612C/A677T/C678T/ A976T/A977G/T978C/A1141C/A1142G/A1143T/A1216T/ T1218G/C1276T/T1278C | |
| AHB3 50 | protein: | D20V/Q89H/L156F/T187I/Y204C/N226I/M285L/K324I/ N326C/K381R/K389I | 40.05 |
| | gene: | A59T/C60G/A267T/A468T/C560T/G561T/A611G/T612C/ A677T/C678T/A853C/A971T/A972T/A976T/A977G/T978C/ A1141C/A1142G/A1143T/A1166T/A1167C | |
| AHB3 51 | protein: | D20V/V75E/Q89H/L156F/T187I/Y204C/M285L/M321I/ N326C/K389I | 19.36 |
| | gene: | A59T/C60G/T224A/A267T/A468T/C560T/G561T/A611G/ T612C/A853C/G963T/A976T/A977G/T978C/A1166T/ A1167C | |
| AHB3 52 | protein: | D20V/T164I/T187I/N226I/L258I/N326C/K381R/K389I | 28.16 |
| | gene: | A59T/C60G/C491T/A492T/C560T/G561T/A677T/C678T/ T772A/A774T/A976T/A977G/T978C/A1141C/A1142G/A1143T/ A1166T/A1167C | |
| AHB3 53 | protein: | L156F/T164I/T187I/Y204C/N226I/L258I/M321I/K324I/N326C | 27.65 |
| | gene: | A468T/C491T/A492T/C560T/G561T/A611G/T612C/A677T/ C678T/T772A/A774T/G963T/A971T/A972T/A976T/A977G/ T978C | |
| AHB3 54 | protein: | V75E/Q89H/T164I/T187I/N326C/K381R/K389I | 30.65 |
| | gene: | T224A/A267T/C491T/A492T/C560T/G561T/A976T/A977G/ T978C/A1141C/A1142G/A1143T/A1166T/A1167C | |
| AHB3 55 | protein: | L156F/T187I/N226I/L258I/M285L/M321I/N326C/K381R/ K389I/I406L | 41.74 |
| | gene: | A468T/C560T/G561T/A677T/C678T/T772A/A774T/A853C/ G963T/A976T/A977G/T978C/A1141C/A1142G/A1143T/ A1166T/A1167C/A1216T/T1218G | |
| AHB3 56 | protein: | Q89H/T164I/T187I/Y204C/L258I/N326C/K381R | 36.40 |
| | gene: | A267T/C491T/A492T/C560T/G561T/A611G/T612C/T772A/ A774T/A976T/A977G/T978C/A1141C/A1142G/A1143T | |
| AHB3 57 | protein: | D20V/Q89H/T187I/L258I/N326C | 41.30 |
| | gene: | A59T/C60G/A267T/C560T/G561T/T772A/A774T/A976T/ A977G/T978C | |
| AHB3 58 | protein: | V75E/L156F/T187I/M285L/N326C/K389I | 53.85 |
| | gene: | T224A/A468T/C560T/G561T/A853C/A976T/A977G/T978C/ A1166T/A1167C | |
| AHB3 59 | protein: | Q89H/L156F/T187I/Y204C/N226I/L258I/N326C/K389I/ I406L/R426C | 31.44 |
| | gene: | A267T/A468T/C560T/G561T/A611G/T612C/A677T/C678T/ T772A/A774T/A976T/A977G/T978C/A1166T/A1167C/ A1216T/T1218G/C1276T/T1278C | |

TABLE 1-continued

Aspartase variant protein, gene mutation sites and the relative results
of the catalytic activity of the ammoniation of acrylic acid

| Variants | | substitutions | relative activity Variants/WT |
|---|---|---|---|
| WT | — | — | WT |
| AHB3 60 | protein: | D20V/V75E/L156F/T164I/T187I/Y204C/M285L/N326C/K381R/K389I | 40.31 |
| | gene: | A59T/C60G/T224A/A468T/C491T/A492T/C560T/G561T/A611G/T612C/A853C/A976T/A977G/T978C/A1141C/A1142G/A1143T/A1166T/A1167C | |
| AHB3 61 | protein: | V75E/Q89H/L156F/T164I/T187I/N226I/N326C/I406L | 24.68 |
| | gene: | T224A/A267T/A468T/C491T/A492T/C560T/G561T/A677T/C678T/A976T/A977G/T978C/A1216T/T1218G | |
| AHB3 62 | protein: | T187I/M285L/N326C/K381R/K389I/P456L | 44.33 |
| | gene: | C560T/G561T/A853C/A976T/A977G/T978C/A1141C/A1142G/A1143T/A1166T/A1167C/C1366T/C1367T/A1368G | |
| AHB3 63 | protein: | V75E/Q89H/T164I/T187I/M321I/K324I/N326C/K381R/I406L | 44.79 |
| | gene: | T224A/A267T/C491T/A492T/C560T/G561T/G963T/A971T/A972T/A976T/A977G/T978C/A1141C/A1142G/A1143T/A1216T/T1218G | |
| AHB3 64 | protein: | Q89H/L156F/T187I/L258I/M321I/K324I/N326C | 15.05 |
| | gene: | A267T/A468T/C560T/G561T/T772A/A774T/G963T/A971T/A972T/A976T/A977G/T978C | |
| AHB3 65 | protein: | T187I/L258I/M285L/N326C/K389I | 41.59 |
| | gene: | C560T/G561T/T772A/A774T/A853C/A976T/A977G/T978C/A1166T/A1167C | |
| AHB3 66 | protein: | T187I/Y204C/N226I/L258I/N326C/R426C | 36.85 |
| | gene: | C560T/G561T/A611G/T612C/A677T/C678T/T772A/A774T/A976T/A977G/T978C/C1276T/T1278C | |
| AHB3 67 | protein: | V75E/Q89H/T164I/T187I/Y204C/M285L/N326C/R426C | 53.56 |
| | gene: | T224A/A267T/C491T/A492T/C560T/G561T/A611G/T612C/A853C/A976T/A977G/T978C/C1276T/T1278C | |
| AHB3 68 | protein: | T187I/Y204C/N226I/L258I/N326C | 13.47 |
| | gene: | C560T/G561T/A611G/T612C/A677T/C678T/T772A/A774T/A976T/A977G/T978C | |
| AHB3 69 | protein: | D20V/L156F/T164I/T187I/N226I/L258I/M285L/N326C/I406L/R426C | 32.02 |
| | gene: | A59T/C60G/A468T/C491T/A492T/C560T/G561T/A677T/C678T/T772A/A774T/A853C/A976T/A977G/T978C/A1216T/T1218G/C1276T/T1278C | |
| AHB3 70 | protein: | T187I/Y204C/L258I/N326C/K381R | 18.37 |
| | gene: | C560T/G561T/A611G/T612C/T772A/A774T/A976T/A977G/T978C/A1141C/A1142G/A1143T | |
| AHB3 71 | protein: | D20V/T187I/N326C/K381R/I406L | 22.23 |
| | gene: | A59T/C60G/C560T/G561T/A976T/A977G/T978C/A1141C/A1142G/A1143T/A1216T/T1218G | |
| AHB3 72 | protein: | D20V/V75E/T187I/N226I/K324I/N326C/K381R/K389I/P456L | 34.19 |
| | gene: | A59T/C60G/T224A/C560T/G561T/A677T/C678T/A971T/A972T/A976T/A977G/T978C/A1141C/A1142G/A1143T/A1166T/A1167C/C1366T/C1367T/A1368G | |
| AHB3 73 | protein: | D20V/Q89H/T187I/L258I/M321I/K324I/N326C/K389I | 35.87 |
| | gene: | A59T/C60G/A267T/C5 60T/G5 61T/T772A/A774T/G963T/A971T/A972T/A976T/A977G/T97 8C/A1166T/A1167C | |
| AHB3 74 | protein: | T164I/T187I/Y204C/M285L/N326C/R426C | 50.12 |
| | gene: | C491T/A492T/C560T/G561T/A611G/T612C/A853C/A976T/A977G/T978C/C1276T/T1278C | |
| AHB3 75 | protein: | L156F/T187I/Y204C/N326C/K381R | 40.72 |
| | gene: | A468T/C560T/G561T/A611G/T612C/A976T/A977G/T978C/A1141C/A1142G/A1143T | |
| AHB3 76 | protein: | T187I/L258I/N326C/K389I/I406L/R426C | 32.68 |
| | gene: | C560T/G561T/T772A/A774T/A976T/A977G/T978C/A1166T/A1167C/A1216T/T1218G/C1276T/T1278C | |
| AHB3 77 | protein: | L156F/T187I/M285L/N326C/K389I | 45.87 |
| | gene: | A468T/C560T/G561T/A853C/A976T/A977G/T978C/A1166T/A1167C | |
| AHB3 78 | protein: | D20V/T164I/T187I/L258I/K324I/N326C | 20.73 |
| | gene: | A59T/C60G/C491T/A492T/C560T/G561T/T772A/A774T/A971T/A972T/A976T/A977G/T978C | |
| AHB3 79 | protein: | V75E/L156F/T164I/T187I/Y204C/N226I/L258I/M285L/M321I/K324I/N326C | 48.01 |
| | gene: | T224A/A468T/C491T/A492T/C560T/G561T/A611G/T612C/A677T/C678T/T772A/A774T/A853C/G963T/A971T/A972T/A976T/A977G/T978C | |

TABLE 1-continued

Aspartase variant protein, gene mutation sites and the relative results of the catalytic activity of the ammoniation of acrylic acid

| Variants | | substitutions | relative activity Variants/WT |
|---|---|---|---|
| WT | — | — | WT |
| AHB3 80 | protein: gene: | V75E/T187I/M285L/K324I/N326C/K381R/R426C T224A/C560T/G561T/A853C/A971T/A972T/A976T/A977G/ T978C/A1141C/A1142G/A1143T/C1276T/T1278C | 31.16 |
| AHB3 81 | protein: gene: | V75E/T187I/N226I/M285L/N326C T224A/C560T/G561T/A677T/C678T/A853C/A976T/A977G/ T978C | 45.50 |
| AHB3 82 | protein: gene: | Q89H/L156F/T187I/N326C/K381R A267T/A468T/C560T/G561T/A976T/A977G/T978C/A1141C/ A1142G/A1143T | 39.12 |
| AHB3 83 | protein: gene: | D20V/T187I/K324I/N326C/I406L A59T/C60G/C560T/G561T/A971T/A972T/A976T/A977G/ T978C/A1216T/T1218G | 28.08 |
| AHB3 84 | protein: gene: | D20V/T187I/M321I/N326C/K389I A59T/C60G/C560T/G561T/G963T/A976T/A977G/T978C/ A1166T/A1167C | 33.93 |
| AHB3 85 | protein: gene: | V75E/L156F/T187I/N326C/R426C T224A/A468T/C560T/G561T/A976T/A977G/T978C/C1276T/ T1278C | 28.65 |
| AHB3 86 | protein: gene: | T187I/Y204C/N326C/I406L/R426C C560T/G561T/A611G/T612C/A976T/A977G/T978C/A1216T/ T1218G/C1276T/T1278C | 16.04 |

Note: numbering of protein substitutions starts from the N-terminus of the amino acid sequence shown in sequence 2; and numbering of gene substitutions starts from the 5' end of the nucleotide sequence shown in sequence 1.

The results show that the enzyme activity of the obtained mutants increased by 5-45 times compared with the wild type aspartase.

VIII. Determination of pH Spectrum

By adjusting the amount of ammonia in the substrate, 400 mM substrates with different pH values (7.0, 7.5, 8.0, 8.5, 9.0, 9.5, 10.0, and 10.5) were prepared.

After mixing 25 mg of crude enzyme proteins of wild type aspartase or variants thereof with different pH substrates, stirring at 40° C. for 1.0 h of the reaction, and the activity of catalyzed acrylic acid ammoniation was determined. To determine the relative activity, the activity measured at pH 8.0 was set to 100%, and the results are shown in Table 2.

TABLE 2 pH spectrum measurement results of aspartase variants

| | pH values | | | | | | | |
|---|---|---|---|---|---|---|---|---|
| Variants | 7.0 | 7.5 | 8.0 | 8.5 | 9.0 | 9.5 | 10.0 | 10.5 |
| WT | 0.21 | 0.46 | 1.00 | 0.81 | 0.59 | 0.32 | 0.27 | 0.19 |
| AHB001 | 0.39 | 0.71 | 1.00 | 0.91 | 0.82 | 0.69 | 0.54 | 0.39 |
| AHB032 | 0.59 | 0.83 | 1.00 | 1.02 | 0.92 | 0.72 | 0.62 | 0.33 |
| AHB063 | 0.61 | 0.81 | 1.00 | 1.17 | 0.87 | 0.86 | 0.71 | 0.46 |
| AHB085 | 0.50 | 0.80 | 1.00 | 1.08 | 0.80 | 0.76 | 0.69 | 0.51 |
| AHB116 | 0.44 | 0.84 | 1.00 | 1.02 | 0.92 | 0.81 | 0.66 | 0.29 |
| AHB148 | 0.46 | 0.74 | 1.00 | 1.15 | 0.95 | 079 | 0.73 | 0.54 |
| AHB229 | 0.45 | 0.84 | 1.00 | 0.99 | 0.82 | 0.76 | 0.62 | 0.44 |
| AHB244 | 0.51 | 0.86 | 1.00 | 1.02 | 0.79 | 0.69 | 0.61 | 0.36 |
| AHB294 | 0.52 | 0.78 | 1.00 | 1.01 | 0.89 | 0.78 | 0.55 | 0.41 |
| AHB327 | 0.43 | 0.73 | 1.00 | 0.95 | 0.85 | 0.81 | 0.73 | 0.49 |
| AHB357 | 0.50 | 0.69 | 1.00 | 1.26 | 1.14 | 0.90 | 0.81 | 0.63 |
| AHB373 | 0.62 | 0.77 | 1.00 | 1.00 | 0.91 | 0.73 | 0.55 | 0.42 |

The results showed that compared with the wild type aspartase, the pH spectrum of the obtained variants was significantly broadened, and the optimal pH value of some variants for catalyzing substrate reactions increased to about 8.5-9.0.

IX. Determination of Temperature Spectrum

Mixing 25 mg of crude protein of wild type aspartase or variants thereof with 1.0 mL of pH 8.0, 400 mM substrate, and stirring at different temperatures (30° C., 35° C., 40° C., 45° C., 50° C., 55° C.), respectively for reacting 1.0 h. Then, the activity of catalyzing the ammoniation of acrylic acid is measured. To determine the relative activity, the activity measured at 40° C. was set to 100%, and the results are shown in Table 3.

TABLE 3

Temperature spectrum measurement results of aspartase variants

| | temperature | | | | | | |
|---|---|---|---|---|---|---|---|
| Variants | 30° C. | 35° C. | 37° C. | 40° C. | 45° C. | 50° C. | 55° C. |
| WT | 0.41 | 0.62 | 0.55 | 1.00 | 0.79 | 0.62 | 0.20 |
| AHB001 | 0.39 | 0.67 | 0.79 | 1.00 | 0.88 | 0.81 | 0.76 |
| AHB032 | 0.56 | 0.84 | 0.89 | 1.00 | 1.06 | 0.86 | 0.84 |
| AHB063 | 0.20 | 0.63 | 0.96 | 1.00 | 1.05 | 0.82 | 0.75 |
| AHB085 | 0.52 | 0.72 | 0.84 | 1.00 | 0.89 | 0.89 | 0.76 |
| AHB116 | 0.76 | 0.87 | 1.10 | 1.00 | 1.13 | 0.92 | 0.81 |
| AHB148 | 0.70 | 0.90 | 0.91 | 1.00 | 1.34 | 0.96 | 0.79 |
| AHB229 | 0.58 | 0.86 | 0.99 | 1.00 | 0.99 | 0.91 | 0.87 |
| AHB244 | 0.78 | 1.05 | 0.89 | 1.00 | 1.04 | 1.06 | 0.84 |
| AHB294 | 0.51 | 0.80 | 0.95 | 1.00 | 1.00 | 0.92 | 0.84 |
| AHB327 | 0.67 | 0.88 | 1.01 | 1.00 | 1.26 | 1.09 | 0.79 |
| AHB357 | 0.31 | 0.54 | 0.73 | 1.00 | 1.31 | 1.14 | 0.98 |
| AHB373 | 0.77 | 1.03 | 0.96 | 1.00 | 0.99 | 1.03 | 0.87 |

The results showed that compared with the wild type aspartase, the temperature spectrum of the obtained variants was significantly broadened, and the optimal temperature for catalyzing substrate of some variants increased to 45° C.-50° C.

X. Determination of Thermal Stability

After incubating 25 mg of crude enzyme protein of wild type aspartase or variants thereof at 40° C. for 4 hours, mixing with 1.0 mL of pH 8.0 and 400 mM substrate, and stirring at 40° C. for 1.0 h of reaction. Then, the activity of catalyzing the ammoniation of acrylic acid is measured. The experimental group is one or more (several) variants of aspartase, and the control group is wild type aspartase. The results are shown in Table 4.

TABLE 4

Measurement results of thermal stability of aspartase variants

| Variants | Enzyme activity retention |
|---|---|
| WT | 21.40% |
| AHB001 | 39.03% |
| AHB032 | 60.64% |
| AHB063 | 56.16% |
| AHB085 | 50.88% |
| AHB116 | 58.08% |
| AHB148 | 44.40% |
| AHB229 | 52.24% |
| AHB244 | 57.52% |
| AHB294 | 51.36% |
| AHB327 | 54.80% |
| AHB357 | 64.08% |
| AHB373 | 60.64% |

The results showed that the thermal stability of the obtained variant increased significantly compared with the wild-type aspartase. After incubating at 40° C. for 4 hours, the enzyme activity retention rate increased by about 2-3 times.

XI. Determination of Acrylic Acid Conversion

Mixing 25 mg of crude enzyme proteins of wild type aspartase or variants thereof was with 1.0 mL of substrate (with a concentration of 400 mM) at pH 8.5, and stirring at 45° C. for 0-5 h of reaction. Acrylic acid residues are detected by liquid chromatogram, to calculate the conversion ratio. The results are shown in Table 5.

TABLE 5

Determination of acrylic acid conversion ratio

| Variants | conversion ratio after different reaction time | | | | | | |
|---|---|---|---|---|---|---|---|
| | 0 h | 0.5 h | 1.0 h | 2.0 h | 3.0 h | 4.0 h | 5.0 h |
| WT | 0% | 0.54% | 0.86% | 0.90% | 1.03% | 1.26% | 1.34% |
| AHB-001 | 0% | 10.62% | 30.64% | 45.39% | 53.64% | 62.32% | 68.33% |
| AHB-063 | 0% | 19.44% | 51.15% | 69.54% | 84.21% | 88.43% | 91.12% |
| AHB-116 | 0% | 31.26% | 49.75% | 65.41% | 77.34% | 82.22% | 84.73% |
| AHB-357 | 0% | 26.41% | 59.72% | 74.49% | 87.32% | 92.25% | 93.67% |
| AHB-373 | 0% | 23.63% | 54.26% | 72.91% | 83.69% | 89.24% | 92.13% |

As shown in Table 5, after 5 hours of reaction, the conversion ratio of the wild type aspartase substrate was only 1.34%, the substrate conversion ratio of the AHB001 variant reached 68.33%, and the substrate conversion ratios of the other shown variants reached greater than 84%.

The invention described and claimed herein is not limited to the specific embodiments disclosed herein, as the above embodiments are intended to be illustrative of a particular aspect of the invention and any equivalent embodiments are intended to be included in the scope of the invention.

INDUSTRIAL APPLICATION

Compared with the wild type parent aspartase, the aspartase variant provided in the present invention has improved catalytic activity of the ammoniation of acrylic acid, and has better thermal stability and pH spectrum, and the conversion ratio of acrylic acid can be improved significantly in the reaction of the ammoniation of acrylic acid. The aspartase variant provided in the present invention has important application value for catalyzing the ammoniation of acrylic acid to generate β-alanine, and then meeting the needs of industrialization.

What is claimed is:

1. An aspartase variant, the amino acid sequence thereof is more than 96% identical to SEQ ID NO. 2 in the sequence listing, and has mutations of T187I and N326C at both positions 187 and 326 of SEQ ID NO. 2, and the aspartase variant has improved catalytic activity for the ammoniation of acrylic acid compared with that of aspartase shown in SEQ ID NO. 2.

2. The aspartase variant according to claim 1, wherein compared with the SEQ ID NO. 2 in the sequence listing, the amino acid sequence of the aspartase variant further having a mutation at sequence position 156.

3. The aspartase variant according to claim 2, wherein compared with the SEQ ID NO. 2 in the sequence listing, the amino acid sequence of the aspartase variant further having a mutation at position L156F.

4. A nucleic acid molecule encoding the aspartase variant according to claim 1;
   or, a recombinant vector, expression cassette, or an isolated recombinant cell containing the nucleic acid molecule encoding the aspartase variant according to claim 1.

5. The nucleic acid molecule according to claim 4, wherein the nucleic acid molecule is a gene encoding the aspartase variant, and compared with SEQ ID NO. 1 in the sequence listing, the nucleotide sequence of the gene has or just has the combined mutations shown in any one of 1) to 385) as follows:
   1) T224A/C560T/G561T/T772A/A774T/A976T/A977G/T978C/A1166T/A1167C;
   2) T224A/C560T/G561T/T772A/A774T/A976T/A977G/T978C/A1141C/A1142G/A11 43T;
   3) T224A/C560T/G561T/T772A/A774T/A971T/A972T/A976T/A977G/T978C/A1166T/A1167C/C1276T/T1278C/C1366T/C1367T/A1368G;
   4) T224A/C560T/G561T/T772A/A774T/A853C/A976T/A977G/T978C/A1216T/T1218G;
   5) T224A/C560T/G561T/T772A/A774T/A853C/A976T/A977G/T978C/A1166T/A1167C;
   6) T224A/C560T/G561T/G963T/A1216T/T1218G/A976T/A977G/T978C/C1276T/T1278C;
   7) T224A/C560T/G561T/A976T/A977G/T978C/A1141C/A1142G/A1143T/A1216T/T 1218G;
   8) T224A/C560T/G561T/A976T/A977G/T978C/A1141C/A1142G/A1143T/A1166T/A 1167C/A1216T/T1218G/C1276T/T1278C;
   9) T224A/C560T/G561T/A971T/A972T/A976T/A977G/T978C/A1166T/A1167C;

10) T224A/C560T/G561T/A853C/G963T/A971T/A972T/A976T/A977G/T978C/C1276T/T1278C;

11) T224A/C560T/G561T/A853C/A971T/A972T/A976T/A977G/T978C/C1276T/T1278C;

12) T224A/C560T/G561T/A853C/A971T/A972T/A976T/A977G/T978C/A1141C/A1142 G/A1143T/C1276T/T1278C;

13) T224A/C560T/G561T/A677T/C678T/T772A/A774T/A971T/A972T/A976T/A977G/T978C/A1141C/A1142G/A1143T/A1216T/T1218G;

14) T224A/C560T/G561T/A677T/C678T/G963T/A971T/A972T/A976T/A977G/T978C/C1366T/C1367T/A1368G;

15) T224A/C560T/G561T/A677T/C678T/A976T/A977G/T978C/A1141C/A1142G/A1143T;

16) T224A/C560T/G561T/A677T/C678T/A853C/A976T/A977G/T978C;

17) T224A/C560T/G561T/A611G/T612C/G963T/A976T/A977G/T978C;

18) T224A/C560T/G561T/A611G/T612C/A976T/A977G/T978C/A1216T/T1218G;

19) T224A/C560T/G561T/A611G/T612C/A853C/G963T/A976T/A977G/T978C/A1141C/A1142G/A1143T/A1216T/T1218G/C1366T/C1367T/A1368G;

20) T224A/C560T/G561T/A611G/T612C/A677T/C678T/T772A/A774T/A976T/A977G/T978C/A1216T/T1218G;

21) T224A/C560T/G561T/A611G/T612C/A677T/C678T/A971T/A972T/A976T/A977G/T978C/A1141C/A1142G/A1143T/A1216T/T1218G;

22) T224A/C560T/G561T/A611G/T612C/A677T/C678T/A853C/A971T/A972T/A976T/A977G/T978C/A1141C/A1142G/A1143T/C1276T/T1278C;

23) T224A/C491T/A492T/C560T/G561T/T772A/A774T/A976T/A977G/T978C/A1166T/A1167C;

24) T224A/C491T/A492T/C560T/G561T/T772A/A774T/A976T/A977G/T978C/A1141C/A1142G/A1143T/C1276T/T1278C;

25) T224A/C491T/A492T/C560T/G561T/T772A/A774T/A853C/G963T/A976T/A977G/T978C/A1141C/A1142G/A1143T/A1166T/A1167C/A1216T/T1218G/C1276T/T1278C;

26) T224A/C491T/A492T/C560T/G561T/T772A/A774T/A853C/G963T/A971T/A972T/A976T/A977G/T978C/A1216T/T1218G/C1276T/T1278C;

27) T224A/C491T/A492T/C560T/G561T/G963T/A976T/A977G/T978C/A1216T/T1218G;

28) T224A/C491T/A492T/C560T/G561T/G963T/A976T/A977G/T978C/A1141C/A1142G/A1143T/A1216T/T1218G;

29) T224A/C491T/A492T/C560T/G561T/G963T/A971T/A972T/A976T/A977G/T978C/A1166T/A1167C/C1276T/T1278C/C1366T/C1367T/A1368G;

30) T224A/C491T/A492T/C560T/G561T/A677T/C678T/T772A/A774T/A976T/A977G/T978C/A1166T/A1167C;

31) T224A/C491T/A492T/C560T/G561T/A677T/C678T/T772A/A774T/A853C/A976T/A977G/T978C/A1166T/A1167C/A1216T/T1218G;

32) T224A/C491T/A492T/C560T/G561T/A677T/C678T/T772A/A774T/A853C/A971T/A972T/A976T/A977G/T978C/A1166T/A1167C;

33) T224A/C491T/A492T/C560T/G561T/A677T/C678T/G963T/A976T/A977G/T978C/A1166T/A1167C;

34) T224A/C491T/A492T/C560T/G561T/A677T/C678T/A971T/A972T/A976T/A977G/T978C/A1216T/T1218G;

35) T224A/C491T/A492T/C560T/G561T/A677T/C678T/A853C/A971T/A972T/A976T/A977G/T978C/A1141C/A1142G/A1143T;

36) T224A/C491T/A492T/C560T/G561T/A611G/T612C/T772A/A774T/G963T/A976T/A977G/T978C/A1141C/A1142G/A1143T/A1166T/A1167C/A1216T/T1218G;

37) T224A/A468T/C560T/G561T/T772A/A774T/A971T/A972T/A976T/A977G/T978C;

38) T224A/A468T/C560T/G561T/A976T/A977G/T978C/C1276T/T1278C;

39) T224A/A468T/C560T/G561T/A976T/A977G/T978C/A1166T/A1167C/C1276T/T 1278C;

40) T224A/A468T/C560T/G561T/A853C/G963T/A976T/A977G/T978C/A1216T/T1218G/C1276T/T1278C;

41) T224A/A468T/C560T/G561T/A853C/G963T/A971T/A972T/A976T/A977G/T978C/A1141C/A1142G/A1143T/C1366T/C1367T/A1368G;

42) T224A/A468T/C560T/G561T/A853C/A976T/A977G/T978C/A1166T/A1167C;

43) T224A/A468T/C560T/G561T/A677T/C678T/T772A/A774T/A853C/A976T/A977G/T978C;

44) T224A/A468T/C560T/G561T/A677T/C678T/A971T/A972T/A976T/A977G/T978C/A1216T/T1218G/C1276T/T1278C;

45) T224A/A468T/C560T/G561T/A611G/T612C/T772A/A774T/G963T/A976T/A977G/T978C/A1141C/A1142G/A1143T/A1216T/T1218G/C1276T/T1278C;

46) T224A/A468T/C560T/G561T/A611G/T612C/T772A/A774T/G963T/A971T/A972T/A976T/A977G/T978C/A1141C/A1142G/A1143T/A1216T/T1218G/C1276T/T1278C;

47) T224A/A468T/C560T/G561T/A611G/T612C/G963T/A976T/A977G/T978C/A1166T/A1167C/C1276T/T1278C;

48) T224A/A468T/C491T/A492T/C560T/G561T/T772A/A774T/A976T/A977G/T978C;

49) T224A/A468T/C491T/A492T/C560T/G561T/T772A/A774T/A853C/G963T/A976T/A977G/T978C/A1141C/A1142G/A1143T/A1166T/A1167C/C1276T/T1278C;

50) T224A/A468T/C491T/A492T/C560T/G561T/T772A/A774T/A853C/A976T/A977G/T978C/A1141C/A1142G/A1143T/A1166T/A1167C/C1276T/T1278C;

51) T224A/A468T/C491T/A492T/C560T/G561T/G963T/A976T/A977G/T978C;

52) T224A/A468T/C491T/A492T/C560T/G561T/A611G/T612C/T772A/A774T/A976T/A977G/T978C/A1166T/A1167C/A1216T/T1218G;

53) T224A/A468T/C491T/A492T/C560T/G561T/A611G/T612C/T772A/A774T/A853C/G963T/A976T/A977G/T978C/A1166T/A1167C/A1216T/T1218G;

54) T224A/A468T/C491T/A492T/C560T/G561T/A611G/T612C/A853C/A976T/A977G/T978C;

55) T224A/A468T/C491T/A492T/C560T/G561T/A611G/T612C/A677T/C678T/T772A/A774T/A976T/A977G/T978C/A1216T/T1218G;

56) T224A/A468T/C491T/A492T/C560T/G561T/A611G/T612C/A677T/C678T/T772A/A774T/A853C/G963T/A971T/A972T/A976T/A977G/T978C;

57) T224A/A267T/C560T/G561T/T772A/A774T/G963T/A976T/A977G/T978C/A1216T/T1218G/C1276T/T1278C;
58) T224A/A267T/C560T/G561T/T772A/A774T/A976T/A977G/T978C/A1141C/A1142G/A1143T/A1166T/A1167C;
59) T224A/A267T/C560T/G561T/G963T/A976T/A977G/T978C/A1141C/A1142G/A1143T/A1166T/A1167C/A1216T/T1218G/C1366T/C1367T/A1368G;
60) T224A/A267T/C560T/G561T/G963T/A971T/A972T/A976T/A977G/T978C/A1216T/T1218G;
61) T224A/A267T/C560T/G561T/A976T/A977G/T978C/A1166T/A1167C/C1276T/T 1278C;
62) T224A/A267T/C560T/G561T/A677T/C678T/A976T/A977G/T978C/A1166T/A1167C;
63) T224A/A267T/C560T/G561T/A611G/T612C/T772A/A774T/G963T/A976T/A977G/T978C/A1141C/A1142G/A1143T/A1166T/A1167C/A1216T/T1218G/C1276T/T1278C;
64) T224A/A267T/C560T/G561T/A611G/T612C/T772A/A774T/A853C/G963T/A976T/A977G/T978C/A1216T/T1218G/C1276T/T1278C;
65) T224A/A267T/C560T/G561T/A611G/T612C/A971T/A972T/A976T/A977G/T978C/A1216T/T1218G;
66) T224A/A267T/C560T/G561T/A611G/T612C/A677T/C678T/T772A/A774T/A971T/A972T/A976T/A977G/T978C/A1141C/A1142G/A1143T;
67) T224A/A267T/C491T/A492T/C560T/G561T/T772A/A774T/A853C/G963T/A976T/A977G/T978C/A1166T/A1167C/C1276T/T1278C;
68) T224A/A267T/C491T/A492T/C560T/G561T/G963T/A976T/A977G/T978C/A1141C/A1142G/A1143T/A1166T/A1167C/C1276T/T1278C;
69) T224A/A267T/C491T/A492T/C560T/G561T/G963T/A971T/A972T/A976T/A977G/T978C/A1141C/A1142G/A1143T/A1216T/T1218G;
70) T224A/A267T/C491T/A492T/C560T/G561T/A976T/A977G/T978C/A1141C/A1142G/A1143T/A1166T/A1167C;
71) T224A/A267T/C491T/A492T/C560T/G561T/A976T/A977G/T978C;
72) T224A/A267T/C491T/A492T/C560T/G561T/A611G/T612C/T772A/A774T/G963T/A976T/A977G/T978C;
73) T224A/A267T/C491T/A492T/C560T/G561T/A611G/T612C/T772A/A774T/A976T/A977G/T978C/A1216T/T1218G;
74) T224A/A267T/C491T/A492T/C560T/G561T/A611G/T612C/A976T/A977G/T978C/A1166T/A1167C;
75) T224A/A267T/C491T/A492T/C560T/G561T/A611G/T612C/A853C/A976T/A977G/T978C/C1276T/T1278C;
76) T224A/A267T/C491T/A492T/C560T/G561T/A611G/T612C/A853C/A976T/A977G/T978C/A1166T/A1167C/C1276T/T1278C;
77) T224A/A267T/C491T/A492T/C560T/G561T/A611G/T612C/A677T/C678T/A853C/G963T/A976T/A977G/T978C/A1166T/A1167C/C1276T/T1278C;
78) T224A/A267T/A468T/C560T/G561T/T772A/A774T/G963T/A976T/A977G/T978C/A1216T/T1218G/C1276T/T1278C;
79) T224A/A267T/A468T/C560T/G561T/G963T/A976T/A977G/T978C/C1276T/T1278C;
80) T224A/A267T/A468T/C560T/G561T/G963T/A976T/A977G/T978C/A1216T/T1218G;
81) T224A/A267T/A468T/C560T/G561T/G963T/A971T/A972T/A976T/A977G/T978C;
82) T224A/A267T/A468T/C560T/G561T/A976T/A977G/T978C/A1141C/A1142G/A1143T/C1276T/T1278C;
83) T224A/A267T/A468T/C560T/G561T/A971T/A972T/A976T/A977G/T978C/A1166T/A1167C/C1276T/T1278C/C1366T/C1367T/A1368G
84) T224A/A267T/A468T/C560T/G561T/A677T/C678T/G963T/A971T/A972T/A976T/A977G/T978C/C1276T/T1278C;
85) T224A/A267T/A468T/C560T/G561T/A677T/C678T/A853C/A976T/A977G/T978C/A1141C/A1142G/A1143T/A1166T/A1167C;
86) T224A/A267T/A468T/C560T/G561T/A611G/T612C/A976T/A977G/T978C;
87) T224A/A267T/A468T/C491T/A492T/C560T/G561T/A853C/A976T/A977G/T978C/A1141C/A1142G/A1143T/A1166T/A1167C/C1276T/T1278C;
88) T224A/A267T/A468T/C491T/A492T/C560T/G561T/A677T/C678T/G963T/A976T/A977G/T978C/A1216T/T1218G;
89) T224A/A267T/A468T/C491T/A492T/C560T/G561T/A677T/C678T/A976T/A977G/T978C/A1216T/T1218G;
90) T224A/A267T/A468T/C491T/A492T/C560T/G561T/A677T/C678T/A976T/A977G/T978C/A1166T/A1167C/A1216T/T1218G;
91) T224A/A267T/A468T/C491T/A492T/C560T/G561T/A611G/T612C/T772A/A774T/A853C/G963T/A976T/A977G/T978C/A1166T/A1167C;
92) T224A/A267T/A468T/C491T/A492T/C560T/G561T/A611G/T612C/A853C/G963T/A976T/A977G/T978C/A1166T/A1167C;
93) T224A/A267T/A468T/C491T/A492T/C560T/G561T/A611G/T612C/A853C/A976T/A977G/T978C/A1141C/A1142G/A1143T/A1166T/A1167C/C1276T/T1278C;
94) T224A/A267T/A468T/C491T/A492T/C560T/G561T/A611G/T612C/A677T/C678T/A853C/A971T/A972T/A976T/A977G/T978C;
95) C560T/G561T/T772A/A774T/G963T/A976T/A977G/T978C/A1216T/T1218G;
96) C560T/G561T/T772A/A774T/A976T/A977G/T978C/A1216T/T1218G/C1276T/T 1278C;
97) C560T/G561T/T772A/A774T/A976T/A977G/T978C/A1166T/A1167C/A1216T/T 1218G/C1276T/T1278C;
98) C560T/G561T/T772A/A774T/A976T/A977G/T978C/A1141C/A1142G/A1143T/C 1276T/T1278C;
99) C560T/G561T/T772A/A774T/A976T/A977G/T978C/A1141C/A1142G/A1143T/A 1216T/T1218G/C1276T/T1278C;
100) C560T/G561T/T772A/A774T/A976T/A977G/T978C/A1141C/A1142G/A1143T/A1166T/A1167C/A1216T/T 1218G;
101) C560T/G561T/T772A/A774T/A971T/A972T/A976T/A977G/T978C/A1166T/A1167C/A1216T/T1218G;
102) C560T/G561T/T772A/A774T/A853C/G963T/A976T/A977G/T978C/A1141C/A1142G/A1143T;
103) C560T/G561T/T772A/A774T/A853C/G963T/A976T/A977G/T978C;
104) C560T/G561T/T772A/A774T/A853C/G963T/A971T/A972T/A976T/A977G/T978C/A1141C/A1142G/A1143T/A1216T/T1218G;

105) C560T/G561T/T772A/A774T/A853C/A976T/A977G/T978C/C1276T/T1278C;
106) C560T/G561T/T772A/A774T/A853C/A976T/A977G/T978C/A1166T/A1167C;
107) C560T/G561T/G963T/A976T/A977G/T978C/A1141C/A1142G/A1143T/A1166T/A1167C/C1276T/T1278C;
108) C560T/G561T/G963T/A971T/A972T/A976T/A977G/T978C/A1141C/A1142G/A1143T;
109) C560T/G561T/A976T/A977G/T978C/A1166T/A1167C/A1216T/T1218G/C1276T/T1278C/C1366T/C1367T/A1368G;
110) C560T/G561T/A976T/A977G/T978C/A1141C/A1142G/A1143T/A1166T/A1167C/C1366T/C1367T/A1368G;
111) C560T/G561T/A976T/A977G/T978C/A1141C/A1142G/A1143T/A1166T/A1167C/A1216T/T1218G/C1276T/T1278C;
112) C560T/G561T/A971T/A972T/A976T/A977G/T978C/A1216T/T1218G/C1276T/T1278C/C1366T/C1367T/A1368G;
113) C560T/G561T/A971T/A972T/A976T/A977G/T978C/A1166T/A1167C/C1276T/T1278C;
114) C560T/G561T/A971T/A972T/A976T/A977G/T978C/A1141C/A1142G/A1143T/A1166T/A1167C/A1216T/T1218G;
115) C560T/G561T/A853C/G963T/A976T/A977G/T978C/C1276T/T1278C;
116) C560T/G561T/A853C/G963T/A976T/A977G/T978C/A1216T/T1218G/C1276T/T1278C;
117) C560T/G561T/A853C/A976T/A977G/T978C/A1216T/T1218G/C1276T/T1278C/C1366T/C1367T/A1368G;
118) C560T/G561T/A853C/A976T/A977G/T978C/A1216T/T1218G/C1276T/T1278C;
119) C560T/G561T/A853C/A976T/A977G/T978C/A1141C/A1142G/A1143T/A1216T/T1218G/C1276T/T1278C;
120) C560T/G561T/A853C/A976T/A977G/T978C/A1141C/A1142G/A1143T/A1166T/A1167C/C1366T/C1367T/A1368G;
121) C560T/G561T/A677T/C678T/T772A/A774T/G963T/A976T/A977G/T978C/C1276T/T1278C;
122) C560T/G561T/A677T/C678T/T772A/A774T/A976T/A977G/T978C/C1366T/C1367T/A1368G;
123) C560T/G561T/A677T/C678T/T772A/A774T/A976T/A977G/T978C/A1216T/T1218G/C1366T/C1367T/A1368G;
124) C560T/G561T/A677T/C678T/T772A/A774T/A976T/A977G/T978C/A1216T/T1218G;
125) C560T/G561T/A677T/C678T/T772A/A774T/A976T/A977G/T978C/A1141C/A1142G/A1143T/C1276T/T1278C;
126) C560T/G561T/A677T/C678T/T772A/A774T/A853C/G963T/A976T/A977G/T978C/A1141C/A1142G/A1143T/A1216T/T1218G/C1276T/T1278C/C1366T/C1367T/A1368G;
127) C560T/G561T/A677T/C678T/T772A/A774T/A853C/G963T/A976T/A977G/T978C;
128) C560T/G561T/A677T/C678T/T772A/A774T/A853C/G963T/A971T/A972T/A976T/A977G/T978C/A1216T/T1218G/C1276T/T1278C/C1366T/C1367T/A1368G;
129) C560T/G561T/A677T/C678T/T772A/A774T/A853C/G963T/A971T/A972T/A976T/A977G/T978C/A1141C/A1142G/A1143T/A1166T/A1167C/C1366T/C1367T/A1368G;
130) C560T/G561T/A677T/C678T/T772A/A774T/A853C/G963T/A971T/A972T/A976T/A977G/T978C;
131) C560T/G561T/A677T/C678T/G963T/A976T/A977G/T978C/A1216T/T1218G/C1276T/T1278C;
132) C560T/G561T/A677T/C678T/G963T/A976T/A977G/T978C/A1166T/A1167C/A1216T/T1218G;
133) C560T/G561T/A677T/C678T/G963T/A971T/A972T/A976T/A977G/T978C;
134) C560T/G561T/A677T/C678T/A976T/A977G/T978C/A1216T/T1218G/C1366T/C1367T/A1368G;
135) C560T/G561T/A677T/C678T/A976T/A977G/T978C/A1141C/A1142G/A1143T/C1366T/C1367T/A1368G;
136) C560T/G561T/A677T/C678T/A976T/A977G/T978C/A1141C/A1142G/A1143T/A1216T/T1218G/C1276T/T1278C;
137) C560T/G561T/A677T/C678T/A853C/G963T/A976T/A977G/T978C/A1141C/A1142G/A1143T/A1166T/A1167C/A1216T/T1218G/C1276T/T1278C/C1366T/C1367T/A1368G;
138) C560T/G561T/A677T/C678T/A853C/G963T/A971T/A972T/A976T/A977G/T978C/A1141C/A1142G/A1143T/A1166T/A1167C/A1216T/T1218G/C1366T/C1367T/A1368G;
139) C560T/G561T/A677T/C678T/A853C/A976T/A977G/T978C/C1276T/T1278C;
140) C560T/G561T/A677T/C678T/A853C/A976T/A977G/T978C/A1166T/A1167C/C1276T/T1278C/C1366T/C1367T/A1368G;
141) C560T/G561T/A677T/C678T/A853C/A976T/A977G/T978C/A1141C/A1142G/A1143T/A1166T/A1167C;
142) C560T/G561T/A677T/C678T/A853C/A971T/A972T/A976T/A977G/T978C/C1276T/T1278C;
143) C560T/G561T/A677T/C678T/A853C/A971T/A972T/A976T/A977G/T978C;
144) C560T/G561T/A611G/T612C/T772A/A774T/G963T/A976T/A977G/T978C/C1276T/T1278C;
145) C560T/G561T/A611G/T612C/T772A/A774T/A976T/A977G/T978C/A1141C/A1142G/A1143T;
146) C560T/G561T/A611G/T612C/T772A/A774T/A971T/A972T/A976T/A977G/T978C;
147) C560T/G561T/A611G/T612C/T772A/A774T/A853C/G963T/A971T/A972T/A976T/A977G/T978C/A1141C/A1142G/A1143T/A1216T/T1218G/C1276T/T1278C;
148) C560T/G561T/A611G/T612C/T772A/A774T/A853C/G963T/A971T/A972T/A976T/A977G/T978C/A1141C/A1142G/A1143T/A1166T/A1167C/A1216T/T1218G;
149) C560T/G561T/A611G/T612C/T772A/A774T/A853C/A971T/A972T/A976T/A977G/T978C;
150) C560T/G561T/A611G/T612C/G963T/A976T/A977G/T978C/A1141C/A1142G/A1143T;
151) C560T/G561T/A611G/T612C/A976T/A977G/T978C/C1276T/T1278C/C1366T/C1367T/A1368G;
152) C560T/G561T/A611G/T612C/A976T/A977G/T978C/A1216T/T1218G/C1276T/T1278C;
153) C560T/G561T/A611G/T612C/A976T/A977G/T978C/A1216T/T1218G/C1366T/C1367T/A1368G;
154) C560T/G561T/A611G/T612C/A976T/A977G/T978C/A1141C/A1142G/A1143T/A1166T/A1167C;
155) C560T/G561T/A611G/T612C/A971T/A972T/A976T/A977G/T978C/A1216T/T1218G/C1276T/T1278C;
156) C560T/G561T/A611G/T612C/A853C/A976T/A977G/T978C/C1366T/C1367T/A1368G;

157) C560T/G561T/A611G/T612C/A853C/A976T/ A977G/T978C/A1141C/A1142G/A 1143T/C1276T/ T1278C;
158) C560T/G561T/A611G/T612C/A853C/A976T/ A977G/T978C/A1141C/A1142G/A 1143T;
159) C560T/G561T/A611G/T612C/A677T/C678T/ T772A/A774T/G963T/A976T/A977G/T978C/ A1216T/T1218G;
160) C560T/G561T/A611G/T612C/A677T/C678T/ T772A/A774T/G963T/A971T/A972T/A976T/A977G/ T978C/A1141C/A1142G/A1143T/A1166T/A1167C/ C1366T/C1367T/A1368G;
161) C560T/G561T/A611G/T612C/A677T/C678T/ T772A/A774T/A976T/A977G/T978C/C1276T/ T1278C;
162) C560T/G561T/A611G/T612C/A677T/C678T/ T772A/A774T/A976T/A977G/T978C;
163) C560T/G561T/A611G/T612C/A677T/C678T/ T772A/A774T/A853C/G963T/A976T/A977G/T978C/ A1166T/A1167C/A1216T/T1218G/C1276T/T1278C;
164) C560T/G561T/A611G/T612C/A677T/C678T/ A976T/A977G/T978C/A1141C/A1142G/A1143T;
165) C560T/G561T/A611G/T612C/A677T/C678T/ A971T/A972T/A976T/A977G/T978C/C1276T/ T1278C;
166) C560T/G561T/A611G/T612C/A677T/C678T/ A853C/G963T/A976T/A977G/T978C/A1141C/ A1142G/A1143T/A1166T/A1167C/A1216T/T1218G/ C1366T/C1367T/A1368G;
167) C560T/G561T/A611G/T612C/A677T/C678T/ A853C/A976T/A977G/T978C/C1276T/T1278C;
168) C491T/A492T/C560T/G561T/T772A/A774T/ A853C/G963T/A976T/A977G/T978C/A1141C/ A1142G/A1143T/A1166T/A1167C/A1216T/T1218G/ C1366T/C1367T/A1368G;
169) C491T/A492T/C560T/G561T/T772A/A774T/ A853C/G963T/A971T/A972T/A976T/A977G/T978C/ A1141C/A1142G/A1143T/A1166T/A1167C/C1366T/ C1367T/A1368G;
170) C491T/A492T/C560T/G561T/G963T/A976T/ A977G/T978C/A1216T/T1218G;
171) C491T/A492T/C560T/G561T/A976T/A977G/ T978C/A1141C/A1142G/A1143T/A1216T/T1218G;
172) C491T/A492T/C560T/G561T/A971T/A972T/ A976T/A977G/T978C/C1276T/T1278C;
173) C491T/A492T/C560T/G561T/A971T/A972T/ A976T/A977G/T978C/A1166T/A1167C/C1276T/ T1278C;
174) C491T/A492T/C560T/G561T/A853C/G963T/ A976T/A977G/T978C/A1141C/A1142G/A1143T;
175) C491T/A492T/C560T/G561T/A853C/A976T/ A977G/T978C/A1166T/A1167C;
176) C491T/A492T/C560T/G561T/A853C/A976T/ A977G/T978C/A1141C/A1142G/A 1143T/C1276T/ T1278C;
177) C491T/A492T/C560T/G561T/A677T/C678T/ T772A/A774T/A853C/G963T/A976T/A977G/T978C/ A1141C/A1142G/A1143T/C1276T/T1278C;
178) C491T/A492T/C560T/G561T/A677T/C678T/ T772A/A774T/A853C/G963T/A971T/A972T/A976T/ A977G/T978C/A1141C/A1142G/A1143T/A1166T/ A1167C/C1366T/C1367T/A1368G;
179) C491T/A492T/C560T/G561T/A677T/C678T/ G963T/A971T/A972T/A976T/A977G/T978C/ A1141C/A1142G/A1143T;
180) C491T/A492T/C560T/G561T/A677T/C678T/ A976T/A977G/T978C/C1276T/T1278C;
181) C491T/A492T/C560T/G561T/A677T/C678T/ A976T/A977G/T978C/A1141C/A1142G/A1143T;
182) C491T/A492T/C560T/G561T/A677T/C678T/ A971T/A972T/A976T/A977G/T978C/A1166T/ A1167C/C1366T/C1367T/A1368G;
183) C491T/A492T/C560T/G561T/A677T/C678T/ A853C/G963T/A971T/A972T/A976T/A977G/T978C/ A1141C/A1142G/A1143T/A1216T/T1218G/C1276T/ T1278C;
184) C491T/A492T/C560T/G561T/A677T/C678T/ A853C/A976T/A977G/T978C/C1276T/T1278C;
185) C491T/A492T/C560T/G561T/A611G/T612C/ T772A/A774T/G963T/A971T/A972T/A976T/A977G/ T978C/A1166T/A1167C;
186) C491T/A492T/C560T/G561T/A611G/T612C/ T772A/A774T/A971T/A972T/A976T/A977G/T978C/ A1166T/A1167C;
187) C491T/A492T/C560T/G561T/A611G/T612C/ A853C/A976T/A977G/T978C/C1276T/T1278C;
188) C491T/A492T/C560T/G561T/A611G/T612C/ A677T/C678T/T772A/A774T/G963T/A976T/A977G/ T978C/A1141C/A1142G/A1143T/A1166T/A1167C/ A1216T/T1218G/C1366T/C1367T/A1368G;
189) C491T/A492T/C560T/G561T/A611G/T612C/ A677T/C678T/T772A/A774T/G963T/A971T/A972T/ A976T/A977G/T978C/A1141C/A1142G/A1143T/ C1276T/T1278C;
190) C491T/A492T/C560T/G561T/A611G/T612C/ A677T/C678T/T772A/A774T/A853C/G963T/A971T/ A972T/A976T/A977G/T978C/A1216T/T1218G;
191) C491T/A492T/C560T/G561T/A611G/T612C/ A677T/C678T/T772A/A774T/A853C/A971T/A972T/ A976T/A977G/T978C/A1166T/A1167C;
192) C491T/A492T/C560T/G561T/A611G/T612C/ A677T/C678T/A971T/A972T/A976T/A977G/T978C/ A1166T/A1167C/A1216T/T1218G;
193) C491T/A492T/C560T/G561T/A468T/A971T/ A972T/A976T/A977G/T978C;
194) A59T/C60G/T224A/C560T/G561T/A677T/C678T/ T772A/A774T/A971T/A972T/A976T/A977G/T978C/ A1141C/A1142G/A1143T/A1166T/A1167C/C1366T/ C1367T/A1368G;
195) A59T/C60G/T224A/C560T/G561T/A677T/C678T/ T772A/A774T/A853C/A976T/A977G/T978C/ C1276T/T1278C;
196) A59T/C60G/T224A/C560T/G561T/A677T/C678T/ G963T/A971T/A972T/A976T/A977G/T978C;
197) A59T/C60G/T224A/C560T/G561T/A677T/C678T/ A971T/A972T/A976T/A977G/T978C/A1141C/ A1142G/A1143T/A1166T/A1167C/C1366T/C1367T/ A1368G;
198) A59T/C60G/T224A/C491T/A492T/C560T/G561T/ A853C/G963T/A976T/A977G/T978C/A1141C/ A1142G/A1143T/C1276T/T1278C;
199) A59T/C60G/T224A/C491T/A492T/C560T/G561T/ A611G/T612C/A976T/A977G/T978C;
200) A59T/C60G/T224A/C491T/A492T/C560T/G561T/ A611G/T612C/A853C/G963T/A976T/A977G/T978C/ A1141C/A1142G/A1143T/C1276T/T1278C;
201) A59T/C60G/T224A/A468T/C560T/G561T/G963T/ A971T/A972T/A976T/A977G/T978C/C1276T/ T1278C/C1366T/C1367T/A1368G;
202) A59T/C60G/T224A/A468T/C560T/G561T/A976T/ A977G/T978C/A1166T/A1167C/A1216T/T1218G/ C1276T/T1278C;

203) A59T/C60G/T224A/A468T/C560T/G561T/A976T/ A977G/T978C/A1141C/A1142G/A1143T/C1276T/ T1278C;
204) A59T/C60G/T224A/A468T/C560T/G561T/A677T/ C678T/G963T/A971T/A972T/A976T/A977G/T978C/ C1276T/T1278C/C1366T/C1367T/A1368G;
205) A59T/C60G/T224A/A468T/C560T/G561T/A611G/ T612C/A853C/A976T/A977G/T978C/A1141C/ A1142G/A1143T/A1166T/A1167C;
206) A59T/C60G/T224A/A468T/C491T/A492T/C560T/ G561T/T772A/A774T/G963T/A971T/A972T/A976T/ A977G/T978C/A1141C/A1142G/A1143T/A1216T/ T1218G;
207) A59T/C60G/T224A/A468T/C491T/A492T/C560T/ G561T/A611G/T612C/A853C/A976T/A977G/T978C/ A1141C/A1142G/A1143T/A1166T/A1167C;
208) A59T/C60G/T224A/A267T/C560T/G561T/T772A/ A774T/A853C/G963T/A976T/A977G/T978C/ A1166T/A1167C;
209) A59T/C60G/T224A/A267T/C560T/G561T/A611G/ T612C/G963T/A971T/A972T/A976T/A977G/T978C/ A1141C/A1142G/A1143T;
210) A59T/C60G/T224A/A267T/C491T/A492T/C560T/ G561T/A853C/G963T/A971T/A972T/A976T/A977G/ T978C/A1141C/A1142G/A1143T;
211) A59T/C60G/T224A/A267T/C491T/A492T/C560T/ G561T/A677T/C678T/A853C/G963T/A976T/A977G/ T978C/A1166T/A1167C/A1216T/T1218G;
212) A59T/C60G/T224A/A267T/C491T/A492T/C560T/ G561T/A611G/T612C/T772A/A774T/A853C/A971T/ A972T/A976T/A977G/T978C;
213) A59T/C60G/T224A/A267T/A468T/C560T/G561T/ T772A/A774T/A853C/A971T/A972T/A976T/A977G/ T978C;
214) A59T/C60G/T224A/A267T/A468T/C560T/G561T/ A611G/T612C/T772A/A774T/G963T/A976T/A977G/ T978C/A1166T/A1167C/A1216T/T1218G;
215) A59T/C60G/T224A/A267T/A468T/C560T/G561T/ A611G/T612C/A853C/G963T/A976T/A977G/T978C/ A1166T/A1167C;
216) A59T/C60G/T224A/A267T/A468T/C491T/A492T/ C560T/G561T/T772A/A774T/A976T/A977G/T978C/ A1141C/A1142G/A1143T/A1166T/A1167C/A1216T/ T1218G;
217) A59T/C60G/C560T/G561T/T772A/A774T/G963T/ A976T/A977G/T978C/C1276T/T1278C;
218) A59T/C60G/C560T/G561T/T772A/A774T/G963T/ A976T/A977G/T978C/A1141C/A1142G/A1143T/ A1166T/A1167C/C1276T/T1278C;
219) A59T/C60G/C560T/G561T/T772A/A774T/A971T/ A972T/A976T/A977G/T978C/C1276T/T1278C;
220) A59T/C60G/C560T/G561T/T772A/A774T/A971T/ A972T/A976T/A977G/T978C/A1216T/T1218G;
221) A59T/C60G/C560T/G561T/T772A/A774T/ A1216T/T1218G/A976T/A977G/T978C/C1276T/ T1278C;
222) A59T/C60G/C560T/G561T/G963T/A976T/A977G/ T978C/A1216T/T1218G;
223) A59T/C60G/C560T/G561T/G963T/A976T/A977G/ T978C/A1166T/A1167C;
224) A59T/C60G/C560T/G561T/G963T/A971T/A972T/ A976T/A977G/T978C/A1141C/A1142G/A1143T/ A1216T/T1218G/C1276T/T1278C;
225) A59T/C60G/C560T/G561T/A976T/A977G/T978C/ A1166T/A1167C/C1276T/T1278C;
226) A59T/C60G/C560T/G561T/A976T/A977G/T978C/ A1141C/A1142G/A1143T/C1276T/T1278C;
227) A59T/C60G/C560T/G561T/A976T/A977G/T978C/ A1141C/A1142G/A1143T/A1216T/T1218G;
228) A59T/C60G/C560T/G561T/A971T/A972T/A976T/ A977G/T978C/A1216T/T1218G;
229) A59T/C60G/C560T/G561T/A853C/G963T/A971T/ A972T/A976T/A977G/T978C/C1276T/T1278C;
230) A59T/C60G/C560T/G561T/A853C/G963T/A971T/ A972T/A976T/A977G/T978C/A1166T/A1167C;
231) A59T/C60G/C560T/G561T/A853C/A976T/A977G/ T978C/A1166T/A1167C/A1216T/T1218G/C1276T/ T1278C;
232) A59T/C60G/C560T/G561T/A853C/A976T/A977G/ T978C/A1141C/A1142G/A1143T;
233) A59T/C60G/C560T/G561T/A677T/C678T/T772A/ A774T/A976T/A977G/T978C/A1216T/T1218G/ C1276T/T1278C;
234) A59T/C60G/C560T/G561T/A677T/C678T/T772A/ A774T/A976T/A977G/T978C/A1216T/T1218G;
235) A59T/C60G/C560T/G561T/A677T/C678T/T772A/ A774T/A976T/A977G/T978C/A1166T/A1167C/ A1216T/T1218G;
236) A59T/C60G/C560T/G561T/A677T/C678T/A976T/ A977G/T978C/A1166T/A1167C;
237) A59T/C60G/C560T/G561T/A677T/C678T/A976T/ A977G/T978C/A1141C/A1142G/A1143T;
238) A59T/C60G/C560T/G561T/A677T/C678T/A853C/ A976T/A977G/T978C/C1276T/T1278C;
239) A59T/C60G/C560T/G561T/A677T/C678T/A853C/ A971T/A972T/A976T/A977G/T978C/A1141C/ A1142G/A1143T/C1276T/T1278C;
240) A59T/C60G/C560T/G561T/A611G/T612C/T772A/ A774T/A976T/A977G/T978C/A1141C/A1142G/ A1143T;
241) A59T/C60G/C560T/G561T/A611G/T612C/T772A/ A774T/A853C/G963T/A971T/A972T/A976T/A977G/ T978C/A1166T/A1167C/C1276T/T1278C;
242) A59T/C60G/C560T/G561T/A611G/T612C/A971T/ A972T/A976T/A977G/T978C;
243) A59T/C60G/C560T/G561T/A611G/T612C/A677T/ C678T/T772A/A774T/A976T/A977G/T978C/ A1216T/T1218G/C1276T/T1278C;
244) A59T/C60G/C560T/G561T/A611G/T612C/A677T/ C678T/G963T/A976T/A977G/T978C/A1216T/ T1218G/C1276T/T1278C;
245) A59T/C60G/C560T/G561T/A611G/T612C/A677T/ C678T/A976T/A977G/T978C/A1141C/A1142G/ A1143T/A1216T/T1218G/C1276T/T1278C;
246) A59T/C60G/C560T/G561T/A611G/T612C/A677T/ C678T/A971T/A972T/A976T/A977G/T978C/ A1141C/A1142G/A1143T/C1276T/T1278C;
247) A59T/C60G/C560T/G561T/A611G/T612C/A677T/ C678T/A853C/A971T/A972T/A976T/A977G/T978C/ C1276T/T1278C;
248) A59T/C60G/C491T/A492T/C560T/G561T/T772A/ A774T/G963T/A976T/A977G/T978C/A1166T/ A1167C;
249) A59T/C60G/C491T/A492T/C560T/G561T/T772A/ A774T/A971T/A972T/A976T/A977G/T978C/ A1141C/A1142G/A1143T/A1216T/T1218G;
250) A59T/C60G/C491T/A492T/C560T/G561T/T772A/ A774T/A971T/A972T/A976T/A977G/T978C;
251) A59T/C60G/C491T/A492T/C560T/G561T/T772A/ A774T/A853C/A971T/A972T/A976T/A977G/T978C/ A1216T/T1218G;
252) A59T/C60G/C491T/A492T/C560T/G561T/G963T/ A976T/A977G/T978C/A1166T/A1167C/C1366T/ C1367T/A1368G;

253) A59T/C60G/C491T/A492T/C560T/G561T/G963T/ A976T/A977G/T978C/A1141C/A1142G/A1143T/ C1276T/T1278C;
254) A59T/C60G/C491T/A492T/C560T/G561T/G963T/ A976T/A977G/T978C;
255) A59T/C60G/C491T/A492T/C560T/G561T/A853C/ G963T/A976T/A977G/T978C/A1141C/A1142G/ A1143T/A1166T/A1167C/A1216T/T1218G;
256) A59T/C60G/C491T/A492T/C560T/G561T/A853C/ G963T/A971T/A972T/A976T/A977G/T978C/ A1216T/T1218G;
257) A59T/C60G/C491T/A492T/C560T/G561T/A853C/ A976T/A977G/T978C;
258) A59T/C60G/C491T/A492T/C560T/G561T/A677T/ C678T/T772A/A774T/A976T/A977G/T978C/ C1276T/T1278C;
259) A59T/C60G/C491T/A492T/C560T/G561T/A677T/ C678T/T772A/A774T/A976T/A977G/T978C/ A1166T/A1167C;
260) A59T/C60G/C491T/A492T/C560T/G561T/A677T/ C678T/T772A/A774T/A976T/A977G/T978C/ A1141C/A1142G/A1143T/A1166T/A1167C;
261) A59T/C60G/C491T/A492T/C560T/G561T/A677T/ C678T/T772A/A774T/A853C/A971T/A972T/A976T/ A977G/T978C;
262) A59T/C60G/C491T/A492T/C560T/G561T/A677T/ C678T/A971T/A972T/A976T/A977G/T978C;
263) A59T/C60G/C491T/A492T/C560T/G561T/A611G/ T612C/A853C/A971T/A972T/A976T/A977G/T978C/ A1166T/A1167C/C1276T/T1278C;
264) A59T/C60G/C491T/A492T/C560T/G561T/A611G/ T612C/A677T/C678T/A976T/A977G/T978C/ A1166T/A1167C/A1216T/T1218G;
265) A59T/C60G/A468T/C560T/G561T/T772A/A774T/ G963T/A971T/A972T/A976T/A977G/T978C;
266) A59T/C60G/A468T/C560T/G561T/G963T/A976T/ A977G/T978C/A1216T/T1218G/C1276T/T1278C;
267) A59T/C60G/A468T/C560T/G561T/G963T/A971T/ A972T/A976T/A977G/T978C/A1166T/A1167C/ C1276T/T1278C/C1366T/C1367T/A1368G;
268) A59T/C60G/A468T/C560T/G561T/A853C/G963T/ A971T/A972T/A976T/A977G/T978C/C1276T/ T1278C;
269) A59T/C60G/A468T/C560T/G561T/A853C/G963T/ A971T/A972T/A976T/A977G/T978C/A1166T/ A1167C;
270) A59T/C60G/A468T/C560T/G561T/A853C/A976T/ A977G/T978C;
271) A59T/C60G/A468T/C560T/G561T/A853C/A971T/ A972T/A976T/A977G/T978C/A1141C/A1142G/ A1143T/A1166T/A1167C;
272) A59T/C60G/A468T/C560T/G561T/A677T/C678T/ A976T/A977G/T978C;
273) A59T/C60G/A468T/C560T/G561T/A677T/C678T/ A853C/A976T/A977G/T978C/A1141C/A1142G/ A1143T;
274) A59T/C60G/A468T/C560T/G561T/A611G/T612C/ A976T/A977G/T978C/A1166T/A1167C/A1216T/ T1218G/C1276T/T1278C;
275) A59T/C60G/A468T/C560T/G561T/A611G/T612C/ A971T/A972T/A976T/A977G/T978C;
276) A59T/C60G/A468T/C560T/G561T/A611G/T612C/ A677T/C678T/T772A/A774T/A971T/A972T/A976T/ A977G/T978C/A1141C/A1142G/A1143T/C1276T/ T1278C;
277) A59T/C60G/A468T/C491T/A492T/C560T/G561T/ T772A/A774T/G963T/A976T/A977G/T978C/ A1141C/A1142G/A1143T/A1166T/A1167C/A1216T/ T1218G/C1276T/T 1278C;
278) A59T/C60G/A468T/C491T/A492T/C560T/G561T/ T772A/A774T/A976T/A977G/T978C/A1141C/ A1142G/A1143T/A1166T/A1167C/A1216T/T1218G/ C1276T/T1278C;
279) A59T/C60G/A468T/C491T/A492T/C560T/G561T/ G963T/A971T/A972T/A976T/A977G/T978C;
280) A59T/C60G/A468T/C491T/A492T/C560T/G561T/ A677T/C678T/T772A/A774T/A853C/A976T/A977G/ T978C/A1216T/T1218G/C1276T/T1278C;
281) A59T/C60G/A468T/C491T/A492T/C560T/G561T/ A677T/C678T/A853C/G963T/A971T/A972T/A976T/ A977G/T978C/A1216T/T1218G/C1276T/T1278C;
282) A59T/C60G/A468T/C491T/A492T/C560T/G561T/ A611G/T612C/A677T/C678T/G963T/A971T/A972T/ A976T/A977G/T978C/A1166T/A1167C/C1276T/ T1278C;
283) A59T/C60G/A267T/C560T/G561T/T772A/A774T/ G963T/A971T/A972T/A976T/A977G/T978C/ A1166T/A1167C;
284) A59T/C60G/A267T/C560T/G561T/T772A/A774T/ A976T/A977G/T978C;
285) A59T/C60G/A267T/C560T/G561T/A611G/T612C/ T772A/A774T/A853C/A976T/A977G/T978C/ A1166T/A1167C;
286) A59T/C60G/A267T/C560T/G561T/A611G/T612C/ A853C/G963T/A976T/A977G/T978C/A1141C/ A1142G/A1143T/C1276T/T1278C;
287) A59T/C60G/A267T/C560T/G561T/A611G/T612C/ A853C/A976T/A977G/T978C/C1276T/T1278C;
288) A59T/C60G/A267T/C491T/A492T/C560T/G561T/ A853C/A976T/A977G/T978C/A1141C/A1142G/ A1143T;
289) A59T/C60G/A267T/C491T/A492T/C560T/G561T/ A677T/C678T/T772A/A774T/G963T/A971T/A972T/ A976T/A977G/T978C/A1141C/A1142G/A1143T/ C1366T/C1367T/A1368G;
290) A59T/C60G/A267T/C491T/A492T/C560T/G561T/ A677T/C678T/A976T/A977G/T978C/A1166T/ A1167C/A1216T/T1218G;
291) A59T/C60G/A267T/C491T/A492T/C560T/G561T/ A677T/C678T/A853C/G963T/A976T/A977G/T978C/ A1141C/A1142G/A1143T/C1366T/C1367T/A1368G;
292) A59T/C60G/A267T/C491T/A492T/C560T/G561T/ A611G/T612C/A677T/C678T/A971T/A972T/A976T/ A977G/T978C;
293) A59T/C60G/A267T/C491T/A492T/C560T/G561T/ A611G/T612C/A677T/C678T/A853C/A976T/A977G/ T978C/A1141C/A1142G/A1143T/A1166T/A1167C/ A1216T/T1218G;
294) A59T/C60G/A267T/A468T/C560T/G561T/T772A/ A774T/G963T/A976T/A977G/T978C/A1141C/ A1142G/A1143T/C1366T/C1367T/A1368G;
295) A59T/C60G/A267T/A468T/C560T/G561T/A971T/ A972T/A976T/A977G/T978C/A1141C/A1142G/ A1143T/C1276T/T1278C;
296) A59T/C60G/A267T/A468T/C560T/G561T/A853C/ A976T/A977G/T978C/A1141C/A1142G/A1143T/ A1166T/A1167C;
297) A59T/C60G/A267T/A468T/C560T/G561T/A853C/ A971T/A972T/A976T/A977G/T978C/A1166T/ A1167C;
298) A59T/C60G/A267T/A468T/C560T/G561T/A677T/ C678T/G963T/A976T/A977G/T978C/A1141C/ A1142G/A1143T/A1216T/T1218G;

299) A59T/C60G/A267T/A468T/C560T/G561T/A677T/C678T/A976T/A977G/T978C/A1141C/A1142G/A1143T/A1166T/A1167C;
300) A59T/C60G/A267T/A468T/C560T/G561T/A611G/T612C/A853C/A971T/A972T/A976T/A977G/T978C/A1141C/A1142G/A1143T/A1166T/A1167C;
301) A59T/C60G/A267T/A468T/C560T/G561T/A611G/T612C/A677T/C678T/A853C/A971T/A972T/A976T/A977G/T978C/A1141C/A1142G/A1143T/A1166T/A1167C;
302) A59T/C60G/A267T/A468T/C491T/A492T/C560T/G561T/T772A/A774T/A853C/A976T/A977G/T978C/A1141C/A1142G/A1143T/C1276T/T1278C;
303) A59T/C60G/A267T/A468T/C491T/A492T/C560T/G561T/A677T/C678T/G963T/A976T/A977G/T978C/A1166T/A1167C/A1216T/T1218G/C1276T/T1278C;
304) A59T/C60G/A267T/A468T/C491T/A492T/C560T/G561T/A611G/T612C/T772A/A774T/A853C/A976T/A977G/T978C/A1141C/A1142G/A1143T/C1276T/T1278C;
305) A59T/C60G/A267T/A468T/C491T/A492T/C560T/G561T/A611G/T612C/A853C/A971T/A972T/A976T/A977G/T978C/A1141C/A1142G/A1143T/C1276T/T1278C;
306) A468T/C560T/G561T/T772A/A774T/G963T/A976T/A977G/T978C;
307) A468T/C560T/G561T/T772A/A774T/A853C/G963T/A971T/A972T/A976T/A977G/T978C/A1141C/A1142G/A1143T/A1216T/T1218G/C1276T/T1278C;
308) A468T/C560T/G561T/G963T/A976T/A977G/T978C/A1216T/T1218G;
309) A468T/C560T/G561T/G963T/A976T/A977G/T978C/A1166T/A1167C/C1276T/T1278C;
310) A468T/C560T/G561T/A853C/A976T/A977G/T978C/C1276T/T1278C;
311) A468T/C560T/G561T/A853C/A976T/A977G/T978C/A1166T/A1167C;
312) A468T/C560T/G561T/A677T/C678T/T772A/A774T/A976T/A977G/T978C/A1216T/T1218G;
313) A468T/C560T/G561T/A677T/C678T/T772A/A774T/A853C/G963T/A976T/A977G/T978C/A1141C/A1142G/A1143T/A1166T/A1167C/A1216T/T1218G;
314) A468T/C560T/G561T/A677T/C678T/A976T/A977G/T978C/A1141C/A1142G/A1143T;
315) A468T/C560T/G561T/A611G/T612C/T772A/A774T/A853C/G963T/A976T/A977G/T978C/A1141C/A1142G/A1143T/A1166T/A1167C;
316) A468T/C560T/G561T/A611G/T612C/G963T/A976T/A977G/T978C/A1166T/A1167C/C1276T/T1278C;
317) A468T/C560T/G561T/A611G/T612C/G963T/A971T/A972T/A976T/A977G/T978C, 318) A468T/C560T/G561T/A611G/T612C/A976T/A977G/T978C/C1276T/T1278C;
319) A468T/C560T/G561T/A611G/T612C/A976T/A977G/T978C/A1141C/A1142G/A1143T/C1276T/T1278C;
320) A468T/C560T/G561T/A611G/T612C/A976T/A977G/T978C/A1141C/A1142G/A1143T;
321) A468T/C560T/G561T/A611G/T612C/A971T/A972T/A976T/A977G/T978C/A1166T/A1167C/A1216T/T1218G;
322) A468T/C560T/G561T/A611G/T612C/A971T/A972T/A976T/A977G/T978C/A1141C/A1142G/A1143T/C1276T/T1278C;
323) A468T/C560T/G561T/A611G/T612C/A677T/C678T/A853C/G963T/A976T/A977G/T978C/A1216T/T1218G/C1276T/T1278C/C1366T/C1367T/A1368G;
324) A468T/C560T/G561T/A611G/T612C/A677T/C678T/A853C/A971T/A972T/A976T/A977G/T978C/A1166T/A1167C/C1276T/T1278C/C1366T/C1367T/A1368G;
325) A468T/C560T/G561T/A611G/T612C/A1166T/A1167C/A976T/A977G/T978C/C1276T/T1278C;
326) A468T/C491T/A492T/C560T/G561T/T772A/A774T/A976T/A977G/T978C/A1216T/T1218G/C1276T/T1278C;
327) A468T/C491T/A492T/C560T/G561T/T772A/A774T/A971T/A972T/A976T/A977G/T978C/A1166T/A1167C;
328) A468T/C491T/A492T/C560T/G561T/T772A/A774T/A971T/A972T/A976T/A977G/T978C;
329) A468T/C491T/A492T/C560T/G561T/A976T/A977G/T978C/A1166T/A1167C;
330) A468T/C491T/A492T/C560T/G561T/A971T/A972T/A976T/A977G/T978C/C1276T/T1278C;
331) A468T/C491T/A492T/C560T/G561T/A971T/A972T/A976T/A977G/T978C/A1141C/A1142G/A1143T/A1216T/T1218G/C1276T/T1278C;
332) A468T/C491T/A492T/C560T/G561T/A971T/A972T/A976T/A977G/T978C/A1141C/A1142G/A1143T;
333) A468T/C491T/A492T/C560T/G561T/A677T/C678T/A976T/A977G/T978C/C1276T/T1278C;
334) A468T/C491T/A492T/C560T/G561T/A611G/T612C/A976T/A977G/T978C/A1141C/A1142G/A1143T/C1276T/T1278C;
335) A468T/C491T/A492T/C560T/G561T/A611G/T612C/A677T/C678T/T772A/A774T/G963T/A971T/A972T/A976T/A977G/T978C;
336) A267T/C560T/G561T/T772A/A774T/A976T/A977G/T978C/C1276T/T1278C;
337) A267T/C560T/G561T/T772A/A774T/A976T/A977G/T978C/C1366T/C1367T/A1368G;
338) A267T/C560T/G561T/T772A/A774T/A853C/A976T/A977G/T978C/A1166T/A1167C/A1216T/T1218G;
339) A267T/C560T/G561T/T772A/A774T/A853C/A971T/A972T/A976T/A977G/T978C/A1216T/T1218G;
340) A267T/C560T/G561T/A976T/A977G/T978C/C1276T/T1278C/C1366T/C1367T/A1368G;
341) A267T/C560T/G561T/A971T/A972T/A976T/A977G/T978C/A1166T/A1167C;
342) A267T/C560T/G561T/A853C/A976T/A977G/T978C/C1276T/T1278C;
343) A267T/C560T/G561T/A853C/A976T/A977G/T978C/A1141C/A1142G/A1143T;
344) A267T/C560T/G561T/A677T/C678T/T772A/A774T/G963T/A976T/A977G/T978C/A1141C/A1142G/A1143T/A1166T/A1167C/C1366T/C1367T/A1368G;
345) A267T/C560T/G561T/A677T/C678T/G963T/A976T/A977G/T978C;
346) A267T/C560T/G561T/A677T/C678T/A853C/G963T/A971T/A972T/A976T/A977G/T978C/A1166T/A1167C;
347) A267T/C560T/G561T/A677T/C678T/A853C/G963T/A971T/A972T/A976T/A977G/T978C;

348) A267T/C560T/G561T/A611G/T612C/T772A/A774T/G963T/A971T/A972T/A976T/A977G/T978C/A1141C/A1142G/A1143T/C1276T/T1278C;
349) A267T/C560T/G561T/A611G/T612C/A976T/A977G/T978C/C1366T/C1367T/A 1368G;
350) A267T/C560T/G561T/A611G/T612C/A976T/A977G/T978C/A1216T/T1218G;
351) A267T/C560T/G561T/A611G/T612C/A971T/A972T/A976T/A977G/T978C/A1166T/A1167C/A1216T/T1218G/C1276T/T1278C;
352) A267T/C560T/G561T/A611G/T612C/A677T/C678T/A976T/A977G/T978C/A1166T/A1167C/A1216T/T1218G/C1276T/T1278C;
353) A267T/C560T/G561T/A611G/T612C/A677T/C678T/A976T/A977G/T978C/A1166T/A1167C;
354) A267T/C491T/A492T/C560T/G561T/G963T/A976T/A977G/T978C/A1216T/T1218G;
355) A267T/C491T/A492T/C560T/G561T/A971T/A972T/A976T/A977G/T978C/A1166T/A1167C;
356) A267T/C491T/A492T/C560T/G561T/A853C/G963T/A976T/A977G/T978C/A1141C/A1142G/A1143T/A1166T/A1167C;
357) A267T/C491T/A492T/C560T/G561T/A853C/G963T/A971T/A972T/A976T/A977G/T978C/A1141C/A1142G/A1143T/A1166T/A1167C/A1216T/T1218G/C1366T/C1367T/A1368G;
358) A267T/C491T/A492T/C560T/G561T/A853C/A976T/A977G/T978C;
359) A267T/C491T/A492T/C560T/G561T/A611G/T612C/T772A/A774T/G963T/A971T/A972T/A976T/A977G/T978C/A1166T/A1167C/A1216T/T1218G/C1276T/T1278C;
360) A267T/C491T/A492T/C560T/G561T/A611G/T612C/T772A/A774T/A976T/A977G/T978C/A1141C/A1142G/A1143T;
361) A267T/C491T/A492T/C560T/G561T/A611G/T612C/T772A/A774T/A976T/A977G/T978C;
362) A267T/C491T/A492T/C560T/G561T/A611G/T612C/G963T/A971T/A972T/A976T/A977G/T978C/A1141C/A1142G/A1143T/A1216T/T1218G/C1276T/T1278C;
363) A267T/C491T/A492T/C560T/G561T/A611G/T612C/A677T/C678T/T772A/A774T/G963T/A976T/A977G/T978C/C1276T/T1278C;
364) A267T/C491T/A492T/C560T/G561T/A611G/T612C/A677T/C678T/A971T/A972T/A976T/A977G/T978C/A1141C/A1142G/A1143T/C1276T/T1278C;
365) A267T/A468T/C560T/G561T/T772A/A774T/G963T/A971T/A972T/A976T/A977G/T978C;
366) A267T/A468T/C560T/G561T/A976T/A977G/T978C/A1141C/A1142G/A1143T;
367) A267T/A468T/C560T/G561T/A677T/C678T/T772A/A774T/A853C/A976T/A977G/T978C/A1166T/A1167C/A1216T/T1218G/C1276T/T1278C;
368) A267T/A468T/C560T/G561T/A677T/C678T/A971T/A972T/A976T/A977G/T978C/A1166T/A1167C/A1216T/T1218G/C1276T/T1278C;
369) A267T/A468T/C560T/G561T/A611G/T612C/A976T/A977G/T978C/A1141C/A1142G/A1143T/A1216T/T1218G/C1276T/T1278C/C1366T/C1367T/A1368G;
370) A267T/A468T/C560T/G561T/A611G/T612C/A853C/G963T/A976T/A977G/T978C/C1276T/T1278C/C1366T/C1367T/A1368G;
371) A267T/A468T/C560T/G561T/A611G/T612C/A853C/G963T/A976T/A977G/T978C/A1166T/A1167C/A1216T/T1218G;
372) A267T/A468T/C560T/G561T/A611G/T612C/A677T/C678T/T772A/A774T/A976T/A977G/T978C/A1166T/A1167C/A1216T/T1218G/C1276T/T1278C;
373) A267T/A468T/C560T/G561T/A611G/T612C/A677T/C678T/T772A/A774T/A853C/G963T/A971T/A972T/A976T/A977G/T978C;
374) A267T/A468T/C560T/G561T/A611G/T612C/A677T/C678T/G963T/A971T/A972T/A976T/A977G/T978C/A1141C/A1142G/A1143T/A1216T/T1218G;
375) A267T/A468T/C560T/G561T/A611G/T612C/A677T/C678T/A853C/G963T/A976T/A977G/T978C/A1166T/A1167C/C1276T/T1278C;
376) A267T/A468T/C491T/A492T/C560T/G561T/T772A/A774T/A976T/A977G/T978C/A1166T/A1167C/A1216T/T1218G/C1276T/T1278C;
377) A267T/A468T/C491T/A492T/C560T/G561T/T772A/A774T/A976T/A977G/T978C/A1166T/A1167C;
378) A267T/A468T/C491T/A492T/C560T/G561T/A853C/A976T/A977G/T978C/A1166T/A1167C/A1216T/T1218G/C1276T/T1278C;
379) A267T/A468T/C491T/A492T/C560T/G561T/A677T/C678T/T772A/A774T/G963T/A971T/A972T/A976T/A977G/T978C;
380) A267T/A468T/C491T/A492T/C560T/G561T/A611G/T612C/A853C/G963T/A976T/A977G/T978C/A1166T/A1167C/A1216T/T1218G;
381) A267T/A468T/C491T/A492T/C560T/G561T/A611G/T612C/A853C/A971T/A972T/A976T/A977G/T978C/A1141C/A1142G/A1143T;
382) A267T/A468T/C491T/A492T/C560T/G561T/A611G/T612C/A677T/C678T/T772A/A774T/A853C/A976T/A977G/T978C/A1166T/A1167C/C1276T/T1278C;
383) A267T/A468T/C491T/A492T/C560T/G561T/A611G/T612C/A677T/C678T/T772A/A774T/A853C/A976T/A977G/T978C/A1166T/A1167C;
384) A267T/A468T/C491T/A492T/C560T/G561T/A611G/T612C/A677T/C678T/A971T/A972T/A976T/A977G/T978C/C1366T/C1367T/A1368G;
385) A267T/A468T/C491T/A492T/C560T/G561T/A611G/T612C/A677T/C678T/A853C/A971T/A972T/A976T/A977G/T978C/A1141C/A1142G/A1143T.

6. A method of producing a target product, comprising the steps of using acrylic acid and an ammonia-containing material to react under the catalysis of the aspartase variant according to claim 1 to obtain the target product; and the target product is selected from any one or more of the following: β-alanine, β-alanine salt, multimer of β-alanine.

7. The method according to claim 6, wherein the ammonia-containing material is ammonia water.

8. The method according to claim 6, wherein in the reaction system, the concentration of acrylic acid or acrylate is 20-400 mM, the pH value is 7.0-10.5, and the reaction temperature is 30-55° C., the reaction time is 0.5-5h.

9. The aspartase variant according to claim 3, wherein compared with the SEQ ID NO. 2 in the sequence listing, the amino acid sequence of the aspartase variant has or just has the combined mutations shown in any one of 1)-127) as follows:
1) D20V/Q89H/L156F/T164I/T187I/Y204C/L258I/M285L/N326C/K381R/R426C;
2) Q89H/L156F/T164I/T187I/L258I/N326C/K389I/I406L/R426C;
3) L156F/T164I/T187I/L258I/K324I/N326C/K389I;
4) D20V/L156F/T164I/T187I/Y204C/N226I/M321I/K324I/N326C/K389I/R426C;

5) L156F/T187I/Y204C/K324I/N326C/K389I/I406L;
6) D20V/Q89H/L156F/T187I/M285L/N326C/K381R/K389I;
7) L156F/T164I/T187I/L258I/N326C/I406L/R426C;
8) L156F/T187I/N226I/L258I/N326C/I406L;
9) D20V/L156F/T164I/T187I/N226I/M285L/M321I/K324I/N326C/I406L/R426C;
10) V75E/Q89H/L156F/T187I/N326C/K381R/R426C;
11) V75E/L156F/T187I/M285L/M321I/K324I/N326C/K381R/P456L;
12) Q89H/L156F/T164I/T187I/Y204C/N226I/M285L/K324I/N326C/K381R;
13) V75E/L156F/T187I/N226I/L258I/M285L/N326C;
14) V75E/Q89H/L156F/T164I/T187I/N226I/N326C/K389I/I406L;
15) D20V/Q89H/L156F/T187I/Y204C/M285L/K324I/N326C/K381R/K389I;
16) D20V/Q89H/L156F/T187I/N226I/N326C/K381R/K389I;
17) D20V/V75E/L156F/T187I/N226I/M321I/K324I/N326C/R426C/P456L;
18) V75E/L156F/T187I/Y204C/M321I/N326C/K389I/R426C;
19) D20V/L156F/T187I/L258I/M321I/K324I/N326C;
20) V75E/Q89H/L156F/T187I/M321I/N326C/R426C;
21) V75E/L156F/T164I/T187I/Y204C/N226I/L258I/N326C/I406L;
22) V75E/Q89H/L156F/T164I/T187I/Y204C/M285L/N326C/K381R/K389I/R426C;
23) D20V/V75E/L156F/T187I/N326C/K381R/R426C;
24) D20V/Q89H/L156F/T187I/N226I/M321I/N326C/K381R/I406L;
25) V75E/L156F/T164I/T187I/L258I/M285L/M321I/N326C/K381R/K389I/R426C;
26) D20V/V75E/Q89H/L156F/T187I/L258I/M285L/K324I/N326C;
27) L156F/T164I/T187I/K324I/N326C/R426C;
28) D20V/V75E/L156F/T164I/T187I/L258I/M321I/K324I/N326C/K381R/I406L;
29) V75E/Q89H/L156F/T187I/M321I/K324I/N326C;
30) L156F/T164I/T187I/K324I/N326C/K381R;
31) L156F/T164I/T187I/L258I/K324I/N326C;
32) D20V/V75E/Q89H/L156F/T187I/Y204C/L258I/M321I/N326C/K389I/I406L;
33) D20V/L156F/T187I/M285L/M321I/K324I/N326C/K389I;
34) D20V/L156F/T187I/Y204C/N326C/K389I/I406L/R426C;
35) D20V/V75E/L156F/T187I/N326C/K389I/I406L/R426C;
36) D20V/Q89H/L156F/T164I/T187I/L258I/M285L/N326C/K381R/R426C;
37) V75E/Q89H/L156F/T187I/M321I/N326C/I406L;
38) D20V/Q89H/L156F/T164I/T187I/N226I/M321I/N326C/K389I/I406L/R426C;
39) L156F/T187I/Y204C/M321I/K324I/N326C;
40) D20V/L156F/T164I/T187I/M321I/K324I/N326C;
41) L156F/T187I/Y204C/N226I/M285L/M321I/N326C/I406L/R426C/P456L;
42) V75E/Q89H/L156F/T187I/K324I/N326C/K389I/R426C/P456L;
43) L156F/T164I/T187I/K324I/N326C/K381R/I406L/R426C;
44) D20V/Q89H/L156F/T164I/T187I/Y204C/M285L/K324I/N326C/K381R/R426C;
45) L156F/T187I/Y204C/N326C/R426C;
46) V75E/Q89H/L156F/T187I/L258I/M321I/N326C/I406L/R426C;
47) L156F/T187I/N226I/N326C/K381R;
48) L156F/T187I/L258I/M285L/M321I/K324I/N326C/K381R/I406L/R426C;
49) D20V/L156F/T187I/N226I/M285L/N326C/K381R;
50) D20V/Q89H/L156F/T187I/M285L/K324I/N326C/K389I;
51) Q89H/L156F/T164I/T187I/Y204C/N226I/L258I/M285L/N326C/K389I/R426C;
52) L156F/T164I/T187I/N326C/K389I;
53) L156F/T164I/T187I/N226I/N326C/R426C;
54) V75E/L156F/T164I/T187I/L258I/M285L/N326C/K381R/K389I/R426C;
55) V75E/L156F/T164I/T187I/Y204C/L258I/N326C/K389I/I406L;
56) D20V/Q89H/L156F/T187I/K324I/N326C/K381R/R426C;
57) Q89H/L156F/T187I/Y204C/N226I/M285L/M321I/N326C/K389I/R426C;
58) Q89H/L156F/T164I/T187I/L258I/N326C/K389I;
59) Q89H/L156F/T164I/T187I/Y204C/N226I/K324I/N326C/P456L;
60) V75E/L156F/T164I/T187I/L258I/M285L/M321I/N326C/K389I/I406L;
61) Q89H/L156F/T164I/T187I/N226I/L258I/M321I/K324I/N326C;
62) D20V/L156F/T187I/M285L/M321I/K324I/N326C/R426C;
63) V75E/Q89H/L156F/T164I/T187I/Y204C/N226I/M285L/K324I/N326C;
64) V75E/L156F/T164I/T187I/Y204C/M285L/N326C;
65) V75E/Q89H/L156F/T187I/Y204C/N326C;
66) L156F/T187I/M321I/N326C/I406L;
67) V75E/Q89H/L156F/T164I/T187I/Y204C/L258I/M285L/M321I/N326C/K389I;
68) Q89H/L156F/T164I/T187I/Y204C/N226I/L258I/M285L/N326C/K389I;
69) Q89H/L156F/T187I/Y204C/N226I/M321I/K324I/N326C/K381R/I406L;
70) L156F/T187I/M285L/N326C/R426C;
71) V75E/L156F/T187I/Y204C/L258I/M285L/M321I/N326C/K381R/I406L/R426C;
72) D20V/L156F/T187I/M285L/K324I/N326C/K381R/K389I;
73) Q89H/L156F/T164I/T187I/Y204C/M285L/K324I/N326C/K381R;
74) V75E/L156F/T187I/N326C/K389I/R426C;
75) L156F/T187I/Y204C/K324I/N326C/K381R/R426C;
76) T164I/T187I/L156F/K324I/N326C;
77) Q89H/L156F/T187I/Y204C/N326C/K381R/I406L/R426C/P456L;
78) L156F/T187I/L258I/M321I/N326C;
79) D20V/L156F/T187I/N226I/N326C;
80) V75E/Q89H/L156F/T187I/N226I/M321I/K324I/N326C/R426C;
81) D20V/L156F/T187I/M285L/N326C;
82) V75E/Q89H/L156F/T164I/T187I/Y204C/M285L/M321I/N326C/K389I;
83) L156F/T187I/Y204C/N226I/M285L/K324I/N326C/K389I/R426C/P456L;
84) D20V/L156F/T187I/Y204C/N226I/L258I/K324I/N326C/K381R/R426C;
85) D20V/L156F/T187I/Y204C/K324I/N326C;
86) L156F/T187I/Y204C/L258I/M285L/M321I/N326C/K381R/K389I;

87) V75E/Q89H/L156F/T164I/T187I/M285L/N326C/K381R/K389I/R426C;
88) D20V/L156F/T187I/M321I/N326C/I406L/R426C;
89) V75E/Q89H/L156F/T187I/N226I/M285L/N326C/K381R/K389I;
90) D20V/L156F/T164I/T187I/L258I/N326C/K381R/K389I/I406L/R426C;
91) D20V/V75E/Q89H/L156F/T164I/T187I/L258I/N326C/K381R/K389I/I406L;
92) L156F/T187I/M321I/N326C/K389I/R426C;
93) Q89H/L156F/T187I/N226I/L258I/M285L/N326C/K389I/I406L/R426C;
94) Q89H/L156F/T187I/Y204C/M285L/M321I/N326C/R426C/P456L;
95) Q89H/L156F/T187I/N226I/K324I/N326C/K389I/I406L/R426C;
96) L156F/T164I/T187I/Y204C/N326C/K381R/R426C;
97) Q89H/L156F/T187I/Y204C/N226I/L258I/M285L/M321I/K324I/N326C;
98) V75E/L156F/T164I/T187I/L258I/N326C;
99) L156F/T187I/Y204C/N326C/K381R/R426C;
100) V75E/L156F/T187I/Y204C/L258I/M321I/N326C/K381R/I406L/R426C;
101) D20V/L156F/T164I/T187I/L258I/M321I/N326C/K381R/K389I/I406L/R426C;
102) D20V/L156F/T187I/M321I/K324I/N326C/K389I/R426C/P456L;
103) V75E/L156F/T187I/N226I/K324I/N326C/I406L/R426C;
104) Q89H/L156F/T187I/Y204C/M285L/M321I/N326C/K389I/I406L;
105) D20V/Q89H/L156F/T187I/L258I/M321I/N326C/K381R/P456L;
106) L156F/T187I/Y204C/M321I/N326C/K389I/R426C;
107) D20V/V75E/L156F/T187I/Y204C/M285L/N326C/K381R/K389I;
108) D20V/V75E/L156F/T187I/M321I/K324I/N326C/R426C/P456L;
109) V75E/Q89H/L156F/T164I/T187I/N226I/M321I/N326C/I406L;
110) L156F/T187I/Y204C/K389I/N326C/R426C;
111) Q89H/L156F/T164I/T187I/Y204C/M285L/M321I/N326C/K389I/I406L;
112) Q89H/L156F/T164I/T187I/M285L/N326C/K389I/I406L/R426C;
113) V75E/L156F/T164I/T187I/M321I/N326C;
114) D20V/Q89H/L156F/T187I/Y204C/N226I/M285L/K324I/N326C/K381R/K389I;
115) D20V/V75E/Q89H/L156F/T187I/Y204C/M285L/M321I/N326C/K389I;
116) L156F/T164I/T187I/Y204C/N226I/L258I/M321I/K324I/N326C;
117) L156F/T187I/N226I/L258I/M285L/M321I/N326C/K381R/K389I/I406L;
118) V75E/L156F/T187I/M285L/N326C/K389I;
119) Q89H/L156F/T187I/Y204C/N226I/L258I/N326C/K389I/I406L/R426C;
120) D20V/V75E/L156F/T164I/T187I/Y204C/M285L/N326C/K381R/K389I;
121) V75E/Q89H/L156F/T164I/T187I/N226I/N326C/I406L;
122) Q89H/L156F/T187I/L258I/M321I/K324I/N326C;
123) D20V/L156F/T164I/T187I/N226I/L258I/M285L/N326C/I406L/R426C;
124) L156F/T187I/Y204C/N326C/K381R;
125) V75E/L156F/T164I/T187I/Y204C/N226I/L258I/M285L/M321I/K324I/N326C;
126) Q89H/L156F/T187I/N326C/K381R; or
127) V75E/L156F/T187I/N326C/R426C.

\* \* \* \* \*